United States Patent
Grubb et al.

(10) Patent No.: US 6,759,408 B2
(45) Date of Patent: Jul. 6, 2004

(54) COMBINATION REGIMENS USING PROGESTERONE RECEPTOR MODULATORS

(75) Inventors: Gary S. Grubb, Newtown Square, PA (US); Puwen Zhang, Audubon, PA (US); Eugene A. Terefenko, Quakertown, PA (US); Andrew Fensome, Wayne, PA (US); Jay E. Wrobel, Lawrenceville, NJ (US); Horace Fletcher, III, Pottstown, PA (US); James P. Edwards, San Diego, CA (US); Todd K. Jones, Solana Beach, CA (US); Christopher M. Tegley, Thousand Oaks, CA (US); Lin Zhi, San Diego, CA (US)

(73) Assignees: Wyeth, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/141,792

(22) Filed: May 9, 2002

(65) Prior Publication Data

US 2003/0045511 A1 Mar. 6, 2003

Related U.S. Application Data

(62) Division of application No. 09/552,350, filed on Apr. 19, 2000, now Pat. No. 6,444,668
(60) Provisional application No. 60/229,346, filed on May 4, 1999, now abandoned.

(51) Int. Cl.[7] .................. A61K 31/535; A61K 31/56
(52) U.S. Cl. ............ 514/230.5; 514/178; 514/182; 514/230.08; 514/228.8; 514/247; 514/359; 514/843; 514/170; 514/171
(58) Field of Search .................. 514/230.5, 230.08, 514/182, 178, 228.8, 247, 359, 843, 170, 171

(56) References Cited

U.S. PATENT DOCUMENTS

| | | |
|---|---|---|
| 3,635,964 A | 1/1972 | Skorcz |
| 3,917,592 A | 11/1975 | Kobzina |
| 4,093,730 A | 6/1978 | Butti |
| 4,440,785 A | 4/1984 | Walsh |
| 4,666,913 A | 5/1987 | Kubla |
| 4,670,566 A | 6/1987 | Walsh |
| 4,721,721 A | 1/1988 | Kuhla |
| 4,822,794 A | 4/1989 | Spada |
| 4,831,027 A | 5/1989 | Narr |
| 4,853,473 A | 8/1989 | Fischer |
| 5,007,952 A | 4/1991 | Kume |
| 5,171,851 A | 12/1992 | Kim |
| 5,414,088 A | 5/1995 | von der Saal |
| 5,453,516 A | 9/1995 | Fischer |
| 5,475,020 A | 12/1995 | Johnson |
| 5,521,166 A | 5/1996 | Grubb |
| 5,681,817 A | 10/1997 | Hodgen |
| 5,688,808 A | 11/1997 | Jones |
| 5,688,810 A | 11/1997 | Jones |
| 5,693,646 A | 12/1997 | Jones |
| 5,693,647 A | 12/1997 | Jones |
| 5,696,127 A | 12/1997 | Jones |
| 5,696,130 A | 12/1997 | Jones |
| 5,696,133 A | 12/1997 | Jones |
| 5,719,136 A | 2/1998 | Chwalisz |
| 5,733,902 A | 3/1998 | Schneider |
| 5,808,139 A | 9/1998 | Pathirana |
| 5,874,430 A | 2/1999 | Christ |
| 6,077,840 A | 6/2000 | Kurihara |
| 6,306,851 B1 | 10/2001 | Santilli |
| 6,319,912 B1 | 11/2001 | Grubb |
| 6,329,416 B1 | 12/2001 | Grubb |

(List continued on next page.)

FOREIGN PATENT DOCUMENTS

| | | |
|---|---|---|
| DE | 3633861 | 4/1988 |
| DE | 4330234 | 3/1995 |
| DE | 4344463 | 6/1995 |
| EP | 022317 | 1/1981 |

(List continued on next page.)

OTHER PUBLICATIONS

R. Evans, "The Steroid and Thyroid Hormone Receptor Superfamily", Science, 240:889 (May 13, 1988).

(List continued on next page.)

Primary Examiner—Shengjun Wang
(74) Attorney, Agent, or Firm—Howson and Howson

(57) ABSTRACT

This invention relates to cyclic combination therapies and regimens utilizing substituted indoline derivative compounds which are antagonists of the progesterone receptor having the general structure:

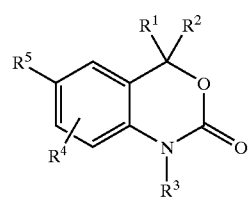

wherein $R^1$ and $R^2$ may be single substituents or fused; $R^3$ is H, OH, $NH_2$, $C_1$ to $C_6$ alkyl, $COR^C$, or optionally substituted $C_1$ to $C_6$ alkyl, $C_3$ to $C_6$ alkenyl, or alkynyl; $R^C$ is H, or optionally substituted $C_1$ to $C_3$ alkyl, aryl, $C_1$ to $C_3$ alkoxy, or $C_1$ to $C_3$ aminoalkyl; $R^4$ is H, halogen, CN, $NO_2$, or optionally substituted $C_1$ to $C_6$ alkyl, alkynyl, $C_1$ to $C_6$ alkoxy, amino, or $C_1$ to $C_6$ aminoalkyl; and $R^5$ is a benzene ring, a five or six membered heterocyclic ring; or pharmaceutically acceptable salt thereof. Methods of treatment include contraception, secondary amenorrhea, dysfunctional bleeding, uterine leiomyomata, endometriosis, polycystic ovary syndrome, carcinomas, adenocarcinomas minimization of side effects, or food intake stimulation.

27 Claims, No Drawings

U.S. PATENT DOCUMENTS

| | | |
|---|---|---|
| 6,339,098 B1 | 1/2002 | Collins |
| 6,355,648 B1 | 3/2002 | Fensome |
| 6,358,947 B1 | 3/2002 | Zhi |
| 6,358,948 B1 | 3/2002 | Zhang |
| 6,369,056 B1 | 4/2002 | Zhang |
| 6,380,178 B1 | 4/2002 | Grubb |
| 6,380,235 B1 | 4/2002 | Zhang |
| 6,391,907 B1 | 5/2002 | Fensome |
| 6,399,593 B1 | 6/2002 | Grubb |
| 6,407,101 B1 | 6/2002 | Collins |
| 6,417,214 B1 | 7/2002 | Ullrich |

FOREIGN PATENT DOCUMENTS

| | | |
|---|---|---|
| EP | 208510 | 1/1987 |
| EP | 311135 | 4/1989 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63112584 | 5/1988 |
| WO | WO86/03749 A1 | 7/1986 |
| WO | WO91/04974 A1 | 4/1991 |
| WO | WO91/06545 A1 | 5/1991 |
| WO | WO93/12085 A1 | 6/1993 |
| WO | WO94/14434 A1 | 7/1994 |
| WO | WO94/29272 A1 | 12/1994 |
| WO | WO95/11013 A1 | 4/1995 |
| WO | WO95/20389 A1 | 8/1995 |
| WO | WO95/20972 A1 | 8/1995 |
| WO | WO95/33746 A1 | 12/1995 |
| WO | WO96/15794 A1 | 5/1996 |
| WO | WO96/19458 A1 | 6/1996 |
| WO | WO96/19997 A1 | 7/1996 |
| WO | WO97/13767 A1 | 4/1997 |
| WO | WO97/49407 A1 | 12/1997 |
| WO | WO98/14436 A1 | 4/1998 |
| WO | WO98/27059 A1 | 6/1998 |
| WO | WO98/55116 A1 | 12/1998 |
| WO | WO99/10325 A1 | 3/1999 |
| WO | WO99/11264 A1 | 3/1999 |
| WO | WO99/15500 A1 | 4/1999 |
| WO | WO99/44608 A1 | 9/1999 |

OTHER PUBLICATIONS

A. Ulmann et al, "Clinical Uses of Mifepristone (MFP)", Ann. N.Y. Acad. Sci., 261:248 (Jun. 12, 1995).

R. Kekkonen et al, "Sequential Regiment of the Antiprogesterone RU486 and Synthetic Progestin for Contraception", Fertility and Sterility, 60(4):610 (Oct., 1993).

K. Horwitz et al, "Progestin, Progesterone Receptors, and Breast Cancer", Horm. Cancer, publisher: Birkhaeuser, Boston, Mass., ed. Vedeckis, pp. 283–306 (1996) (abstract only).

A. Murphy et al, "Regression of Uterine Leiomyomata in Response to the Antiprogesterone RU486", J. Clin. Endo. Metab., 76(2):513 (Feb., 1993).

L. Kettel et al, "Endocrine Responses to Long–Term Administration of the Antiprogesterone RU486 in Patients with Pelvic Endometriosis", Fertility and Sterility, 56(3):402 (Sep., 1991).

H. Michna et al, "Differentiation Therapy with Progesterone Antagonists", Ann. N.Y. Acad. Sci., 761:224 (Jun., 1995).

L. Zhi et al, "5–Aryl–1,2–Dihydrochromeno[3,4–f]quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High–Affinity Ligands with Selectivity for Bone Cell Progesterone Receptors", J. Med. Chem., 38:4880 (Dec. 8, 1995).

K. Perlman et al, "20–Oxopregnacalciferols: Vitamin D Compounds that Bind the Progesterone Receptor", Tet. Letters, 35(15)2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlzaepine Derivatives with Antiprogestin Activity", POI–37, $16^{th}$ Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effects of Brofoxine, A New Anxiolytic on Experimentally Induced Conflict in Rats", Proc. West. Pharmacol. Soc., 21:51–55 (1978).

B. Singh et al, "Novel cAMP PDE III Inhibitor Imidazo[4, 5–b]pyridin–2(3H)–ones and Thiazolo[4,5–b]pyridin–2(3H)–ones and their Analogs", J. Med. Chem., 37:248 (Jan. 21, 1994).

A. Andreani et al, "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7–Chlor–5–phenyl–2–thioxo–1H–2,3–dihydro–1,3,4–benzotriazepinen", Pharmazie, 37(10):714–717 (1982).

E. Barengolts et al, "Progesterone Antagonist RU486 has Bone–Sparing Effects in Ovariectomized Rats", Bone, 17(1):21 (Jul., 1995).

E. Gromachevskaya et al, "Studies of 4H–3, 1–Benzoxazines", Chem. Heterocycl. Cmpds., 33(10):1209–1214 (1997).

D. Chiarino et al, "2,1–Benzisothiazoline 2,2–Dioxide and Derivatives", J. Heterocycl. Chem., 23(6):1645–1649 (Nov.–Dec., 1986).

A. Turck et al, "On the Metabolism of 3–Substituted and 3,6–Disubstituted Pyridazines", Tetrahedron, 49(3):599–606 (1993).

V. Kumar et al, "Synthesis of 7–Azaindole and 7–Azaoxindole Derivatives through a Palladium–Catalyzed CrossCoupling Reaction", J. Org. Chem., 57(25):6995–6998 (1992).

P. Canonne et al, "Spirocyclization of 1–(o–Aminophenyl)cycloalkanols and 1–(2'–Amino–3'–pyridinyl)cycloalkanols", J Heterocyclic Chem., 26:113 (Jan.–Feb., 1989).

M–C. Forest et al, "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", J. Med. Chem., 35:163–172 (Jan., 1992).

D. Combs et al, "Heteroatom Analogues of Bemoradan: Chemistry and Cardiotonic Activity of 1,4–Benzothiazinylpyridazinones", J. Med. Chem., 35:172–176 (Jan., 1992).

Kurihari et al., "Synthesis of (±)–PF1092A, B, and C; New Nonsteroidal Progesterone Receptor Ligands", J. Antibiotics, 50(4):360 (Apr., 1997).

A. Kende et al., "Regioselective C–3 Alkylation of Oxindole Dianion", Synth. Commun. 12(1):1 (1982).

T. Tucker et al., "Synthesis of a Series of 4–(Arylethylnyl)–6–Chloro–4–Cyclopropyl–3,4–dihydroquinazolin–2(1H)–ones as Novel Non–Nucleoside HIV–1 Reverse Transcriptase Inhibitors", J. Med. Chem., 37:2347–2444 (Jul. 22, 1994).

J. Edwards et al., "5–Aryl–1,2–Dihydro–5H–Chromeno[3,4–f]Quinolines as Potent, Orally Active, Nonsteroidal Progesterone Receptor Agonists: The Effect of D–Ring Substituents", J. Med. Chem., 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850.

Derwent WPI abstract, F. Arndt et al., "New Heterocycle substituted Benzo–Fused Azine and Azole Derivatives—Useful as Selective Herbicides for Pre or Post–Emergence Application", EP 311135.

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

V. Mamaev et al., "Synthesis of 4H–Thieno [3,2–B] Pyrrol–5(6H)–One" Bulletin of the Academy of Sciences on the USSR. Division of Chemical Science, US, Consultants Bureau. New York. vol. 9, p. 1549–1553, (1996).

Derwent WPI Abstract, K. Chwalisz et al. "Female Contraceptive Method Comprises Gestation Treatment with Intermittent Progesterone Antagonist Administration.", DE 4,330,234.

Derwent WPI Abstract, K. Chwalisz et al. "Contraceptive Pack for Implantation Inhibition—Contains Competitive Progesterone Antagonist and Gestagen for Sequential Oral Administration.", DE 4,344,463.

K. Kolasa et al., "Preliminary Pharmacological Studies of the Central Action of Phenyl and Piperidinomethyl Derivatives of 2–Benzoxazolone", Chemical Abstracts, vol. 99, No. 1, Abst. No. 157a (Jul. 4, 1983).

N. Meanwell et al., "Regiospecific Functionalization of 1,3–dihydro–2H–Benzimidazol–2–One and Structurally Related Cyclic Urea Derivatives", J. Organic Chem., 60(6):1565–82 (Mar. 24, 1995).

B. Singh et al., "An Efficient and Novel Synthesis of Fused Thiazol–2(3H)–ones" Heterocycles, 36(1):133–134, p. 136, compounds 16a, 18a (Jan. 1993).

G. Vernin et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6– et furyl–6–ethyl–2–benzothiazoles, des sels quaternaires et des spiropyrannes correspondants", Helvetica Chimica Acta, 62(1/3):21–30 (Jan. 24, 1979).

P. Zhang et al, "Cyclocarbamate Derivatives as Progesterone Receptor Modulators", U.S. patent applcation No. 09/552,633, filed Apr. 19, 2000.

P. Zhang et al, "Cyclothiocarbamate Derivatives as Progesterone Receptor Modulators", U.S. patent application No. 09/552,354, filed Apr. 19, 2000.

G. Grubb et al, "Cyclic Regimens Using Quinazolinone and Benzoxazine Derivatives", U.S. patent application No. 09/552,357, filed Apr. 19, 2000.

G. Grubb et al, "Combination Regimens Using Progesterone Receptor Modulators", U.S. patent application No. 09/552,350, filed Apr. 19, 2000.

G. Grubb et al, "Combination Therapies Using Benzimidazolones", U.S. patent application No. 09/552,355, filed Apr. 19, 2000.

G. Grubb et al, "Cyclic Regimens Utilizing Indoline Derivatives", U.S. patent application No. 09/552,358, filed Apr. 19, 2000.

A. Fensome et al, "Thio–Oxindole Derivatives", U.S. patent application No. 10/022,467, filed Oct. 30, 2001 (division of (BBA) cited above).

A. Santilli et al, "Cyclocarbamate and Cyclic Amide Derivatives", U.S. patent application No. 09/906,875, filed Jul. 17, 2001 (division of (BH) cited above).

P. Zhang et al, "Cyclocarbamate Derivatives as Progesterone Receptor Modulators", U.S. patent application No. 09/948,309, filed Sep. 6, 2001 (division of (CW) cited above).

A. Fensome et al, "Indoline Derivatives", U.S. patent application No. 10/014,173, filed Dec. 11, 2001 (division of (BBE) cited above).

P. Zhang et al, "Quinazolinone and Benzoxazine Derivatives as Progesterone Receptor Modulators", U.S. patent application No. 10/023,063, filed Dec. 17, 2001 (division of (BBB) cited above).

P. Zhang et al, "Cyclic Urea and Cyclic Amide Derivatives", U.S. patent application No. 10/050,287, filed Jan. 16, 2002 (division of (BBD) cited above).

M. Collins et al, "Cyanopyrroles", U.S. patent application No. 10/043,513, filed Jan. 9, 2002 (division of (BBI) cited above).

G. Grubb et al, "Combination Regimens Using 3,3–Substituted Indoline Derivatives", U.S. patent application No. 09/977,790, filed Oct. 15, 2001 (division of (BI) cited above).

P. Zhang et al, "Benzimidazolones and Analogues", U.S. patent application No. 10/074,768, filed Feb. 12, 2002 (division of (BBF) cited above).

G. Grubb et al, "Contraceptive Methods Using Benzimidazolones", U.S. patent application No. 10/091,222, filed Mar. 1, 2002 (division of (CCR) cited above).

A. Fensome et al., "Thio–Oxindole Derivatives", U.S. patent application No. 10/117,156, filed Apr. 5, 2002 (continuation of (CCT) cited above).

J. Ullrich et al, "3,3–Substituted Indoline Derivatives", U.S. patent application No. 10/131,379, filed Apr. 24, 2002 (division of (BBJ) cited above).

P. Zhang et al, "Cyclothiocarbamate Derivatives as Progesterone Receptor Modulators", U.S. patent application No. 10/140,034, filed May 6, 2002 (continuation of (CX) cited above).

G. Grubb et al, "Combination Regimens Using Progesterone Receptor Modulators", U.S. patent application No. 10/141,792, filed May 9, 2002 (division of (CZ) cited above).

G. Grubb et al, "Cyclic Regimens Utilizing Indoline Derivatives", U.S. patent application No. 10/153,393, filed May 22, 2002 (division of (CCS) cited above).

COMBINATION REGIMENS USING PROGESTERONE RECEPTOR MODULATORS

CROSS-REFERENCE TO RELATED APPLICATIONS

This application is a divisional of U.S. patent application Ser. No. 09/552,350, filed Apr. 19, 2000, now U.S. Pat. No. 6,444,668, which claims the benefit of the priority of U.S. Provisional Patent Application No. 60/229,346, filed May 4, 1999, now abandoned.

BACKGROUND OF THE INVENTION

This invention relates to regimens of administering compounds, which are antagonists of the progesterone receptor in combination with a progestin, an estrogen, or both. Intracellular receptors (IR) form a class of structurally related gene regulators known as "ligand dependent transcription factors" (R. M. Evans, *Science*, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR antagonists may be used in contraception. In this context they may be administered alone (Ulmann, et al, *Ann. N.Y. Acad. Sci.*, 261, 248, 1995), in combination with a PR agonist (Kekkonen, et al, *Fertility and Sterility*, 60, 610, 1993) or in combination with a partial ER antagonist such as tamoxifen (WO 96/19997 A1 Jul. 4, 1996). PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, *J. Clin. Endo. Metab.*, 76, 513, 1993) and endometriosis (Kettel, et al, *Fertility and Sterility*, 56, 402, 1991). PR antagonists may also be useful in hormone replacement therapy for post menopausal patients in combination with a partial ER antagonist such as tamoxifen (U.S. Pat. No. 5,719,136). PR antagonists, such as mifepristone and onapristone, have been shown to be effective in a model of hormone dependent prostate cancer, which may indicate their utility in the treatment of this condition in men (Michna, et al, *Ann. N.Y. Acad. Sci.*, 761, 224, 1995).

Jones, et al, (U.S. Pat. No. 5,688,810) describe PR antagonist dihydroquinoline 1.

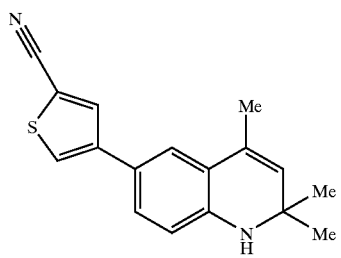

Jones, et al, described the enol ether 2 (U.S. Pat. No. 5,693,646) as a PR ligand.

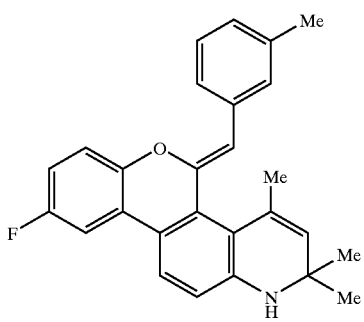

Jones, et al, described compound 3 (U.S. Pat. No. 5,696,127) as a PR ligand.

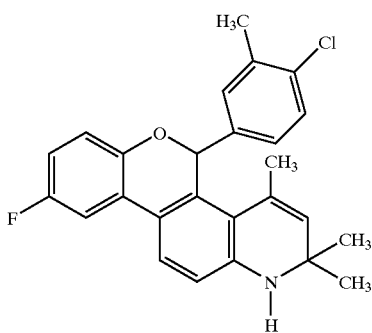

Zhi, et al, described lactones 4, 5 and 6 as PR antagonists (J. Med. Chem., 41, 291, 1998).

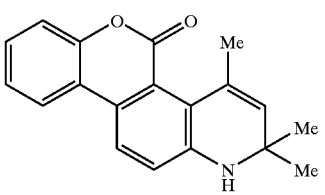

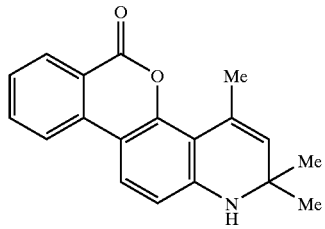

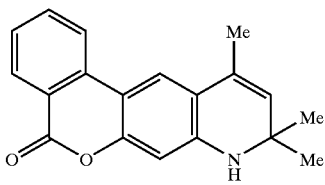

Zhi, et al, described the ether 7 as a PR antagonist (*J. Med. Chem.*, 41, 291, 1998).

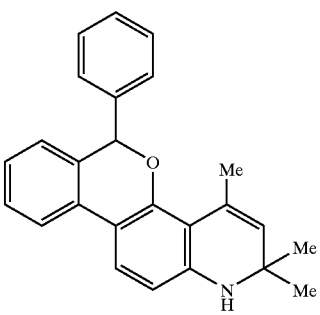

Combs, et al., disclosed the amide 8 as a ligand for the PR (*J. Med. Chem.*, 38, 4880, 1995).

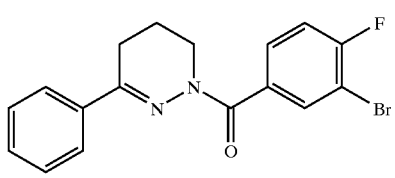

Perlman, et. al., described the vitamin D analog 9 as a PR ligand (*Tet. Letters*, 35, 2295, 1994).

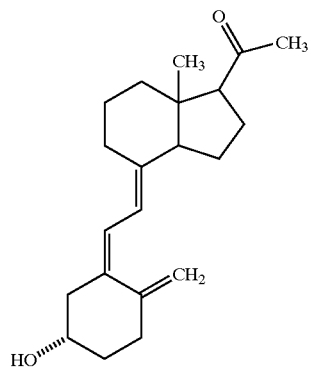

Hamann, et al, described the PR antagonist 10 (*Ann. N.Y. Acad. Sci.*, 761, 383, 1995).

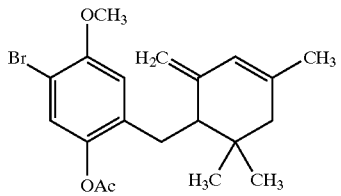

Chen, et al, described the PR antagonist 11 (Chen, et al, POI-37, 16th Int. Cong. Het. Chem, Montana, 1997).

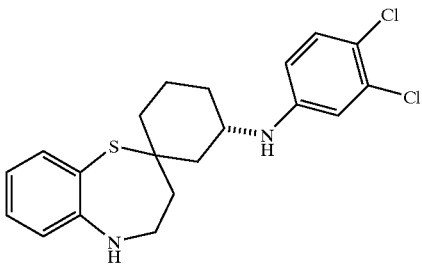

Kurihari, et. al., described the PR ligand 12 (*J. Antibiotics*, 50, 360, 1997).

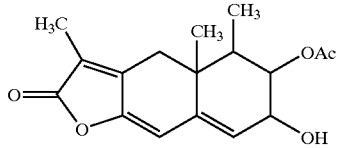

Narr et al. (German Patent, DE 3633861, CA 109:22973) claimed that imidazobenzoxazinones, e.g. A, as cardotonics; Benzoxazin-2-ones, such as brofoxine (B), being active as an anxiolytic was reported by Hartmann et al. (*Proc. West.*

Pharmacol. Soc. 21, 51–55 (1978)); More recently, a number of patents (e.g. Young et al. WO95/20389; Christ et al. WO98/14436) claimed quinazolin-2-ones and benzoxazin-2-ones such as compound C1 and C2 as inhibitors of HIV reverse transcriptase.

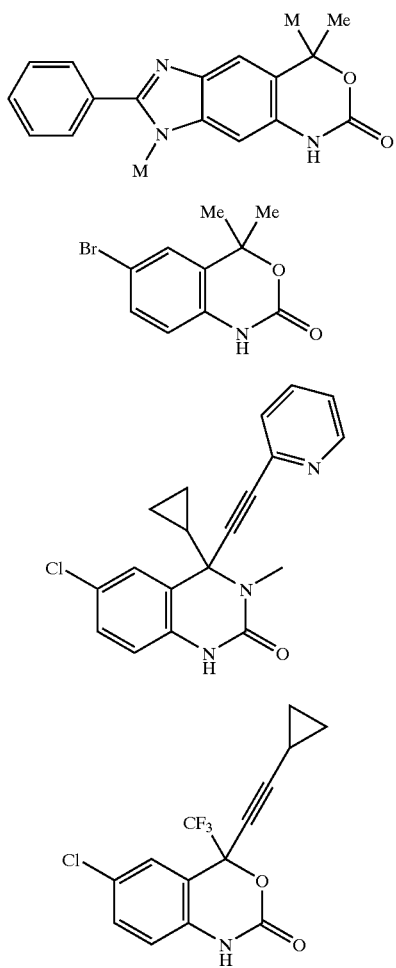

U.S. Pat. No. 5,521,166 (Grubb) teaches cyclophasic hormonal regimens comprising an antiprogestin and a progestin wherein the progestin is administered in the alternating presence and absence of an antiprogestin. The disclosed regimens also provide for use of an estrogen for a period of from 2–4 days to prevent breakthrough bleeding.

DESCRIPTION OF THE INVENTION

This invention provides combination therapies and dosing regimens utilizing antiprogestational agents in combination with one or more progestational agents. This invention further provides methods of treatment and dosing regimens further utilizing in combination with these antiprogestins and progestins, an estrogen, such as ethinyl estradiol.

These regimens and combinations may be administered to a mammal to induce contraception or for the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake. The uses herein for the treatment and/or prevention of the conditions or diseases described above includes the continuous administration or periodic discontinuation of administration of the invention to allow for minimization of effect dose or minimization of side effects or cyclic menstrual bleeding.

The use of this invention for contraception includes administration, preferably orally, to a female of child bearing age an antiprogestin in combination with an estrogen or progestin or both. These administration regimens are preferably carried out over 28 consecutive days, with a terminal portion of the cycle containing administration of no progestins, estrogens or anti-progestins.

The progestins of these combinations may be administered alone or in combination with an estrogen for the first 14–24 days of the cycle, the progestins being administered at a dosage range equal in progestational activity to about 35 µg to about 150 µg levonorgestrel per day, preferably equal in activity to from about 35 µg to about 100 µg levonorgestrel per day. An antiprogestin may then be administered alone or in combination with an estrogen for a period of 1 to 11 days to begin on any cycle day between day 14 and 24. The anti-progestin in these combinations may be administered at a dose of from about 2 µg to about 50 µg per day and the estrogen may be administered at a dose of from about 10 µg to about 35 µg per day. In an oral administration, a package or kit containing 28 tablets will include a placebo tablet on those days when the antiprogestin or progestin or estrogen is not administered.

In a preferred embodiment of this invention, the progestins of this invention may be administered alone or in combination with estrogen for the initial 18 to 21 days of a 28-day cycle, followed by administration of an antiprogestin, alone or in combination with an estrogen, for from 1 to 7 days.

The estrogen to be used in the combinations and formulations of this invention is preferably ethinyl estradiol.

Progestational agents useful with this invention include, but are not limited to, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the preferred progestins for use in the combinations of this invention are levonorgestrel, gestodene and trimegestone.

Examples of orally administered regimens of this invention over a 28 day cycle include administration of a progestational agent solely for the first 21 days at a daily dose equal in progestational activity to from about 35 to about 100 µg of levonorgestrel. An antiprogestin compound of this invention may then be administered at a daily dose of from about 2 to 50 mg from day 22 to day 24, followed by no administration or administration of a placebo for days 25 to 28. It is most preferred that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 µg levonorgestrel, preferably equal in activity to from about 35 to about 100 µg levonorgestrel, with an estrogen, such as ethinyl estradiol, at a daily dose range of from about 10 to about 35 µg. This may be followed as described above with an antiprogestin administered at a daily dose of from about 2 to 50 mg from day 22 to day 24, followed by no administration or administration of a placebo for days 25 to 28.

Still another regimen within the scope of this invention will include coadministration from days 1 to 21 of a progestational agent, the progestational agent, preferably levonorgestrel, being administered at a daily dose equal in progestational activity to from about 35 to about 100 μg levonorgestrel, and an estrogen, such as ethinyl estradiol, at a daily dose range of from about 10 to about 35 μg. This will be followed on days 22 to 24 by coadministration of an antiprogestin (2 to 50 mg/day) and an estrogen, such as ethinyl estradiol, at a daily dose of from about 10 to about 35 μg. From day 25 to day 28, this regimen may be followed by no administration or administration of a placebo.

This invention also kits or packages of pharmaceutical formulations designed for use in the regimens described herein. These kits are preferably designed for daily oral administration over a 28-day cycle, preferably for one oral administration per day, and organized so as to indicate a single oral formulation or combination of oral formulations to be taken on each day of the 28-day cycle. Preferably each kit will include oral tablets to be taken on each the days specified, preferably one oral tablet will contain each of the combined daily dosages indicated.

According to the regimens described above, one 28-day kit may comprise:

a) an initial phase of from 14 to 21 daily dosage units of a progestational agent equal in progestational activity to about 35 to about 150 μg levonorgestrel, preferably equal in progestational activity to about 35 to about 100 μg levonorgestrel;

b) a second phase of from 1 to 11 daily dosage units of an antiprogestin compound of this invention, each daily dosage unit containing an antiprogestin compound at a daily dosage of from about 2 to 50 mg; and c) optionally, a third phase of an orally and pharmaceutically acceptable placebo for the remaining days of the cycle in which no antiprogestin, progestin or estrogen is administered.

A preferred embodiment of this kit may comprise:

a) an initial phase of 21 daily dosage units of a progestational agent equal in progestational activity to about 35 to about 150 μg levonorgestrel, preferably equal in progestational activity to about 35 to about 100 μg levonorgestrel;

b) a second phase of 3 daily dosage units for days 22 to 24 of an antiprogestin compound of this invention, each daily dosage unit containing an antiprogestin compound at a daily dosage of from about 2 to 50 mg; and c) optionally, a third phase of 4 daily units of an orally and pharmaceutically acceptable placebo for each of days 25 to 28.

Another 28-day cycle packaging regimen or kit of this invention comprises:

a) a first phase of from 18 to 21 daily dosage units of a progestational agent equal in progestational activity to about 35 to about 150 μg levonorgestrel, preferably equal in activity to from about 35 to about 100 μg levonorgestrel, and, as an estrogen, ethinyl estradiol at a daily dose range of from about 10 to about 35 μg; and b) a second phase of from 1 to 7 daily dosage units of an antiprogestin of this invention at a daily dose of from about 2 to 50 mg; and c) optionally, an orally and pharmaceutically acceptable placebo for each of the remaining 0–9 days in the 28-day cycle in which no progestational agent, estrogen or antiprogestin is administered.

A preferred embodiment of the kit described above may comprise:

a) a first phase of 21 daily dosage units of a progestational agent equal in progestational activity to about 35 to about 150 μg levonorgestrel, preferably equal in activity to from about 35 to about 100 μg levonorgestrel, and, as an estrogen, ethinyl estradiol at a daily dose range of from about 10 to about 35 μg; and b) a second phase of 3 daily dosage units for days 22 to 24 of an antiprogestin administered at a daily dose of from about 2 to 50 mg; and c) optionally, a third phase of 4 daily dose units of an orally and pharmaceutically acceptable placebo for each of days 25 to 28.

A further 28-day packaged regimen or kit of this invention comprises:

a) a first phase of from 18 to 21 daily dosage units, each containing a progestational agent of this invention at a daily dose equal in progestational activity to about 35 to about 150 μg levonorgestrel, preferably equal in activity to from about 35 to about 100 μg levonorgestrel, and ethinyl estradiol at a daily dose range of from about 10 to about 35 μg;

b) a second phase of from 1 to 7 daily dose units, each daily dose unit containing an antiprogestin of this invention at a concentration of from 2 to 50 mg; and ethinyl estradiol at a concentration of from about 10 to about 35 μg; and c) optionally, an orally and pharmaceutically acceptable placebo for each of the remaining 0–9 days in the 28-day cycle in which no progestational agent, estrogen or antiprogestin is administered.

A preferred embodiment of the package or kit just described comprises:

a) a first phase of 21 daily dosage units, each containing a progestational agent of this invention at a daily dose equal in progestational activity to about 35 to about 150 μg levonorgestrel, preferably from about 35 to about 100 μg levonorgestrel, and ethinyl estradiol at a daily dose range of from about 10 to about 35 μg;

b) a second phase of 3 daily dose units for days 22 to 24, each dose unit containing an antiprogestin of this invention at a concentration of from 2 to 50 mg; and ethinyl estradiol at a concentration of from about 10 to about 35 μg; and c) optionally, a third phase of 4 daily units of an orally and pharmaceutically acceptable placebo for each of days 25 to 28.

In each of the regimens and kits just described, it is preferred that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also preferred that the kits contain the placebo described for the final days of the cycle. It is further preferred that each package or kit comprise a pharmaceutically acceptable package having indicators for each day of the 28-day cycle, such as a labeled blister package or dial dispenser packages known in the art.

In this disclosure, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

Compounds of this invention which may be used as the anti-progestational agents in the kits, methods and regimens herein include those of the Formula I:

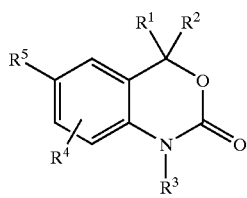

I wherein:
- $R^1$ and $R^2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;
- or $R^1$ and $R^2$ are fused to form:
  a) an optionally substituted 3 to 8 membered spirocyclic alkyl ring;
  b) an optionally substituted 3 to 8 membered spirocyclic alkenyl; or
  c) an optionally substituted 3 to 8 membered heterocyclic ring containing one to three heteroatoms from the group including O, S and N; the spirocyclic rings of a), b) and c) being optionally substituted by from 1 to 4 groups selected from fluorine, $C_1$ to $C_6$ alkyl $C_1$ to $C_6$ alkoxy, $C_1$ to $C_6$ thioalkyl, —$CF_3$, —OH, —CN, $NH_2$, —NH($C_1$ to $C_6$ alkyl), or —N($C_1$ to $C_6$ alkyl)$_2$;
- $R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
- $R^B$ is H, $C_1$ to $C_3$ alkyl or substituted $C_1$ to $C_3$ alkyl;
- $R^3$ is H, OH, $NH_2$, $C_1$ to $C_6$ alkyl substituted $C_1$ to $C_6$ alkyl, $C_3$ to $C_6$ alkenyl, substituted $C_1$ to $C_6$ alkenyl, alkynyl, or substituted alkynyl, $COR^C$;
- $R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ a aminoalkyl, or substituted $C_1$ to $C_3$ aminoalkyl;
- $R^4$ is H, halogen, CN, $NO_2$, $C_1$ to $C_6$ alkyl substituted $C_1$ to $C_6$ alkyl alkynyl, or substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;
- $R^5$ is selected from a) or b)
  a) $R^5$ is a trisubstituted benzene ring containing the substituents X, Y and Z as shown below:

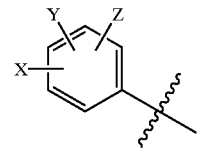

wherein:
- X is taken from the group including halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^D$, $OCOR^D$, or $NR^ECOR^D$;
- $R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
- $R^E$ is H, $C_1$ to $C_3$ alkyl, or substituted $C_1$ to $C_3$ alkyl;
- Y and Z are independent substituents taken from the group including H, halogen, CN, $NO_2$, amino, aminoalkyl, $C_1$ to $C_3$ alkoxy, $C_1$ to $C_3$ alkyl, or $C_1$ to $C_3$ thioalkoxy; or
  b) $R^5$ is a five or six membered ring with 1, 2, or 3 heteroatoms from the group including O, S, SO, $SO_2$ or $NR^6$ and containing one or two independent substituents from the group including H, halogen, CN, $NO_2$, amino, and $C_1$ to $C_3$ alkyl, $C_1$ to $C_3$ alkoxy, $C_1$ to $C_3$ aminoalkyl, $COR^F$, or $NR^GCOR^F$;
- $R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
- $R^G$ is H, $C_1$ to $C_3$ alkyl, or substituted $C_1$ to $C_3$ alkyl;
- $R^6$ is H or $C_1$ to $C_3$ alkyl;
- or pharmaceutically acceptable salt thereof.

Preferred anti-progestin compounds of this invention include those of Formula I:

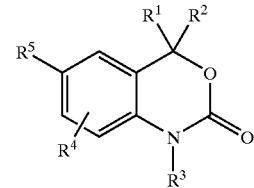

I wherein:
- $R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;
- $R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$; or
- $R^1$ and $R^2$ are fused to form spirocyclic alkyl as a 3 to 8 membered spirocyclic ring, substituted spirocyclic alkyl constructed by fusing $R^1$ and $R^2$ to form a 3 to 8 membered spirocyclic ring, spirocyclic alkenyl constructed by fusing $R^1$ and $R^2$ to form a 3 to 8 membered spirocyclic ring, substituted spirocyclic alkenyl constructed by fusing $R^1$ and $R^2$ to form a 3 to 8 membered spirocyclic ring, spirocyclic alkyl constructed by fusing $R^1$ and $R^2$ to form a 3 to 8 membered spirocyclic ring and containing one to three heteroatoms from the group including O, S and N; substituted spirocyclic alkyl constructed by fusing $R^1$ and $R^2$ to form a 3 to 8 membered spirocyclic ring and containing one to three heteroatoms from the group including O, S and N; the spirocyclic rings made by fusing $R^1$ and $R^2$ being optionally substituted by from 1 to 4 groups selected from fluorine, $C_1$ to $C_6$ alkyl, $C_1$ to $C_6$ alkoxy, $C_1$ to $C_6$ thioalkyl, —$CF_3$, —OH, —CN, $NH_2$, —$NH(C_2$ to $C_6$ alkyl), or —$N(C_1$ to $C_6$ alkyl$)_2$;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is a trisubstituted benzene ring containing the substituents X, Y and Z as shown below:

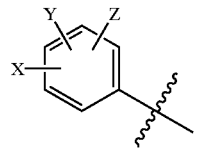

X is taken from the group including halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents taken from the group including H, halogen, CN, $NO_2$, $C_1$ to $C_3$ alkoxy, $C_1$ to $C_3$ alkyl, or $C_1$ to $C_3$ thioalkoxy; or $R^5$ is a five or six membered ring with 1, 2, or 3 heteroatoms from the group including O, S, SO, $SO_2$ or $NR^6$ and containing one or two independent substituents from the group including H, halogen, CN, $NO_2$, amino, and $C_1$ to $C_3$ alkyl, or $C_1$ to $C_3$ alkoxy;

$R^6$ is H, or $C_1$ to $C_3$ alkyl;

or pharmaceutically acceptable salt thereof.

Other preferred progesterone receptor antagonist compounds are those of Formula I

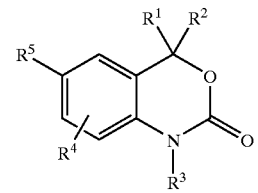

wherein:

$R^1=R^2$ and are selected from the group which includes $C_1$ to $C_3$ alkyl, substituted $C_1$ to $C_3$ alkyl, spirocyclic alkyl constructed by fusing $R^1$ and $R^2$ to form a 3 to 6 membered spirocyclic ring;

$R^3$ is H, OH, $NH_2$, $C_1$ to $C_6$ alkyl, or substituted $C_1$ to $C_6$ alkyl, $COR^C$;

$R^C$ is H, $C_1$ to $C_4$ alkyl, or $C_1$ to $C_4$ alkoxy;

$R^4$ is H, halogen, CN, $NO_2$, $C_1$ to $C_3$ alkyl, substituted $C_1$ to $C_3$ alkyl, $C_1$ to $C_3$ alkoxy, or substituted $C_1$ to $C_3$ alkoxy;

$R^5$ is a disubstituted benzene ring containing the substituents X, and Y as shown below:

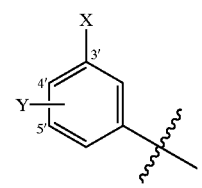

X is taken from the group including halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, $C_1$ to $C_3$ thioalkoxy;

Y is a substituent from the group including H, halogen, CN, $NO_2$, $C_1$ to $C_3$ alkoxy, $C_1$ to $C_4$ alkyl, $C_1$ to $C_3$ thioalkoxy; or $R^5$ is a five membered ring with the structure:

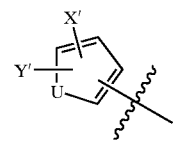

U is O, S, or $NR^6$, $R^6$ is H, or $C_1$ to $C_3$ alkyl, or $C_1$ to $C_4$ $CO_2$alkyl;

X' is from the group including halogen, CN, $NO_2$, or $C_1$ to $C_3$ alkyl and $C_1$ to $C_3$ alkoxy, provided that then U is $NR^6$, then X' is not CN;

Y' is from the group including H and $C_1$ to $C_4$ alkyl; or $R^5$ is a six membered ring with the structure:

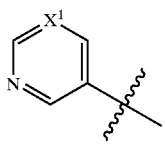

$X^1$ is N or $CX^2$;
$X^2$ is halogen, CN, alkoxy, or $NO_2$;
or pharmaceutically acceptable salt thereof.

Further preferred compounds are those of Formula I:

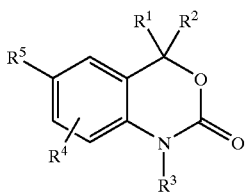

I wherein:
$R^1=R^2$ and are selected from the group which includes $CH_3$ and spirocyclic alkyl constructed by fusing $R^1$ and $R^2$ to form a 6 membered spirocyclic ring
$R^3$ is H, OH, $NH_2$, $CH_3$, substituted methyl, or $COR^C$;
$R^C$ is H, $C_1$ to $C_3$ alkyl, or $C_1$ to $C_4$ alkoxy;
$R^4$ is H, halogen, $NO_2$, CN, or $C_1$ to $C_3$ alkyl;
$R^5$ is a disubstituted benzene ring containing the substituents X and Y as shown below:

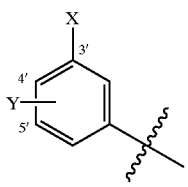

X is taken from the group including halogen, CN, methoxy, $NO_2$, or 2-thiazole;
Y is H or F; or
$R^5$ is a five membered ring with the structure:

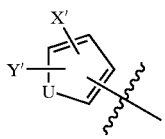

U is O, S, or NH,
X' is halogen, CN, or $NO_2$, provided that when U is $NR^6$, X is not CN;
Y' is H or $C_1$ to $C_4$ alkyl
and pharmaceutically acceptable salts.

The antiprogestin compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having one to eight carbon atoms, preferably one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl group with at least one carbon-carbon triple bond and two to eight carbon atoms, preferably two to six carbon atoms.

The terms "substituted alkyl", "substituted alkenyl", and "substituted alkynyl" refer to alkyl, alkenyl, and alkynyl as just described having from one to three substituents selected from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but not limited to phenyl, naphthyl, biphenyl, anthryl, tetrahydronaphthyl, and phenanthryl.

The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one to four substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom. The term "halogen" refers to Cl, Br, F, or I.

The antiprogestin compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

This invention includes pharmaceutical compositions and regimens comprising one or more pharmacologically active ingredients of this invention and a pharmaceutically acceptable carrier or excipient.

When the active compounds of the regimens are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium Such pharmaceutical preparations may contain, for example, from about 25 to about 90% of the active ingredient in combination with the carrier, more usually between about 5% and 60% by weight.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The antiprogestin compounds of this invention can be prepared following the Schemes illustrated below:

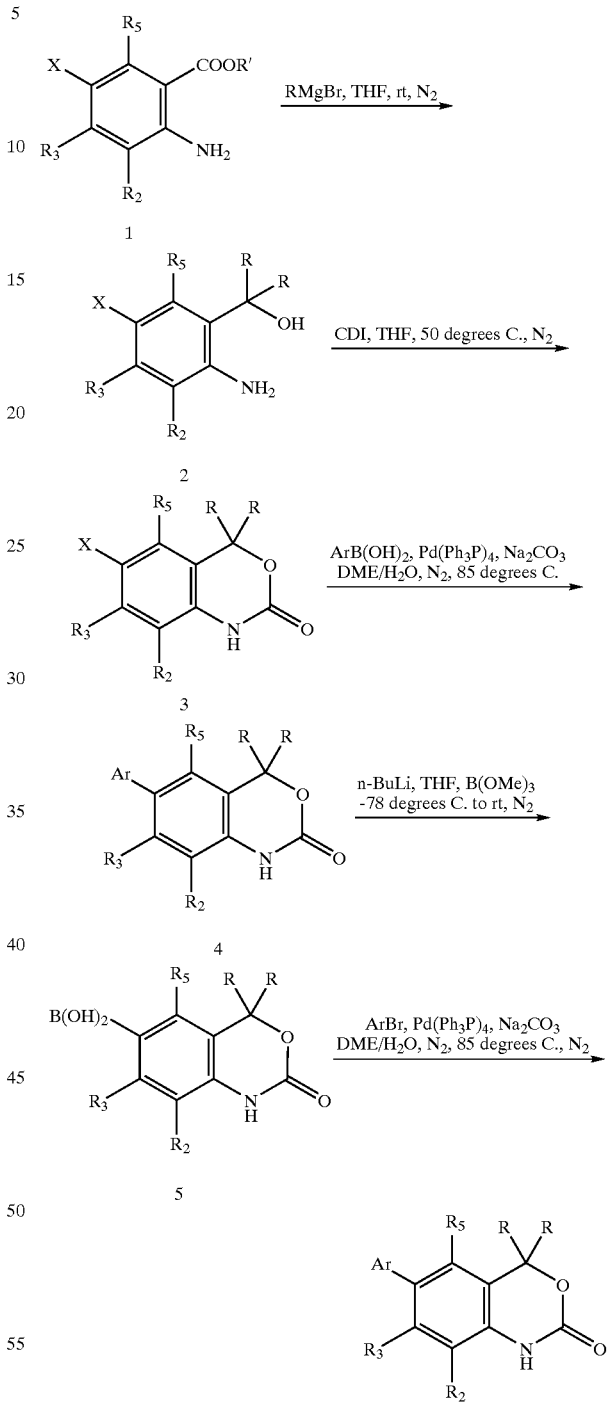

As demonstrated in Scheme I, the antiprogestin compounds of this invention are generally prepared by employing the suitable coupling reaction as a final step. An appropriately substituted ortho-amino benzoic acid or its derivatives such as ethyl ester (X=Br, I,, Cl, or a latent coupling precursor such as alkoxy group which can be converted into OTf group suitable in the coupling reaction)

was treated with a suitable organo metallic reagent, e.g. Grignard reagent, in appropriate nonprotic solvents which include but are not limited to THF or ether to give ortho-amino carbinol 2 under an inert atmosphere such as argon or nitrogen at −78° C. to room temperature. Ring closure of carbinol 2 to yield benzoxazin-2-ones 3 is commonly effected by a condensing agent such as carbonyldiimidazole, phosgene, dimethylcarbonate, or diethylcarbonate in a suitable nonprotic solvent such as THF at temperatures ranging from room temperature to 65° C. The arylation of benzoxazin-2-ones 3 to yield 4 can be effected by various coupling reactions including Suzuki, Stille reactions. These reactions are commonly performed in the presence of transition metallic catalyst, e.g., palladium or nickel complex often with phosphino ligands, e.g., $Ph_3P$, 1,1'-bis(diphenylphosphino)ferrocene, 1,2-bis(diphenylphosphino)ethane or palladium salt such as palladium acetate. Under this catalytic condition, an appropriately substituted nucleophilic reagent, e.g., aryl boronic acid, arylstannane, or aryl zinc compound, is coupled with benzoxazinones 3 to give 4. If a base is needed in the reaction, the commonly used bases include but not limited to sodium bicarbonate, sodium carbonate, potassium phosphate, barium carbonate, potassium acetate, or cesium fluoride. The most commonly used solvents in these reactions include benzene, DMF, isopropanol, toluene, ethanol, DME, ether, acetone or a mixture of any one of these solvents and water. The coupling reaction is generally executed under an inert atmosphere such as nitrogen or argon at temperatures ranging from room temperature to the boiling point of the solvent or solvent system or mixture.

Benzoxazinones 3 can be converted into a nucleophile such as boronic acid which can be coupled with an appropriate electrophile, e.g., aryl bromide or aryl iodide, to yield 4 employing the coupling reaction condition as described above. The transformation of 3 into 5 can be effected by treating 3 with an organo metallic reagent, e.g., n-BuLi, in a nonprotic solvent such as THF or ether followed by quenching the reaction solution with a suitable electrophile such as trimethyl borate, triisopropyl borate, bishexalkyl tin reagent, or zinc chloride at temperatures ranging from −78° C. to reflux temperature under an inert atmosphere such as argon or nitrogen.

Scheme Ia

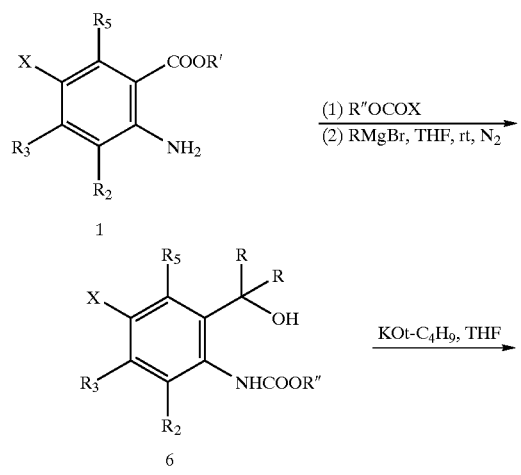

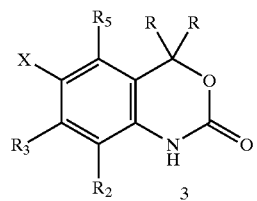

Scheme Ia illustrates an alternative approach leading to the benzoxazinones 3. Thus, an appropriate aniline 1 is protected with a suitable alkoxy carbonyl protective group including but not limited to allyloxy carbonyl, t-butoxy carbonyl, benzoxy carbonyl, ethoxy carbonyl, or methoxy carbonyl in a suitable solvent such as THF, acetonitrile, with or without presence of a base either as a catalyst or as an acid scavenger. The protected aniline is then treated with a suitable organo metallic reagent such as organo lithium agent or Grignard reagent in the same fashion as to prepare compound 2 to give the carbinol 6. The treatment of 6 with a suitable base such as potassium t-butoxide, n-butyl lithium, potassium hydroxide in an appropriate solvent such as toluene, THF, alcohol under an inert atmosphere such as nitrogen or argon at the temperature ranging from room temperature to the boiling point of the relevant solvent to afford benzoxazinones 3.

Scheme II describes the procedures to prepare benzoxazinones bearing two different substituents at position-4. The Weinreb amide 8 can be prepared from an appropriately substituted isatoic anhydride 7 when treated with N-, O-dimethylhydroxyl-amine hydrochloride salt in a protic solvent such as ethanol, isopropanol at reflux under an inert atmosphere such as argon or nitrogen. Coupling of amide 8 with an aryl electrophile such as aryl boronic acid or arylstannane to give 9 can be effected by employing a typical coupling reaction such as Suzuki, Stille coupling procedure in a similar fashion as described for the preparation of benzoxazinones 4. Treatment of Weinreb amide 9 with organo metallic compounds, e.g., alkyllithium, alkynyllithium, aryllithium, or their Grignard counterpart in a nonprotic solvent such as THF or ether under an inert atmosphere such as argon or nitrogen at −78° C. to room temperature affords amino ketone 10. Conversion of ketone 10 to carbinol 11 can be effected by treatment of 10 with an organo metallic reagent such as alkyl, alkynyl, or aryl Grignard compound in a nonprotic solvent such as THF or ether under an inert atmosphere such as argon or nitrogen at −78° C. to room temperature. Conversion of ketone 10 to carbinol 11 can also be effected by reduction of the ketone group of 10 to the carbinol moiety of 11 using an appropriate reducing reagent such as lithium aluminum hydride, sodium borohydride in a suitable solvent such as THF, ether, or anhydrous alcohol under an inert atmosphere in the temperature ranging from 0° C. to the boiling point of the solvent. Ring closure of carbinol 11 to produce the compounds of this invention can be accomplished with condensing agents such as carbonyldiimidazole, phosgene, dimethylcarbonate, or diethylcarbonate in a suitable nonprotic solvent such as THF at temperatures ranging from room temperature to 65° C.

Scheme II

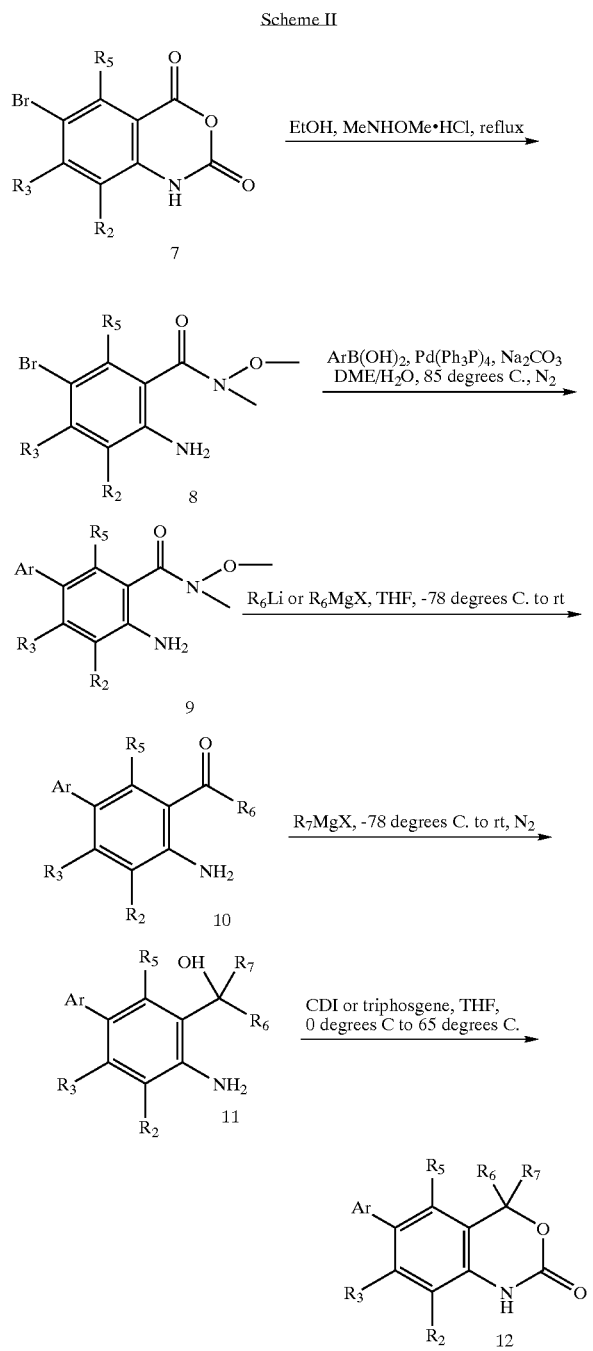

Alternatively, ortho-amino ketone 10 can be prepared by treatment of ortho-amino benzonitrile 14 with an organo metallic compound such as organo lithium reagent or Gringard reagent in a suitable solvent such as THF or ether under an inert atmosphere such as argon or nitrogen at temperatures ranging from −78° C. to room temperature as illustrated in Scheme III. Benzonitrile 14 can be readily prepared from an appropriately substituted benzonitrile such as bromobenzonitrile 13 using a suitable coupling reaction such as Stille or Suzuki protocol carried out in a similar fashion as described for the preparation of the Weinreb amide 9.

Scheme III

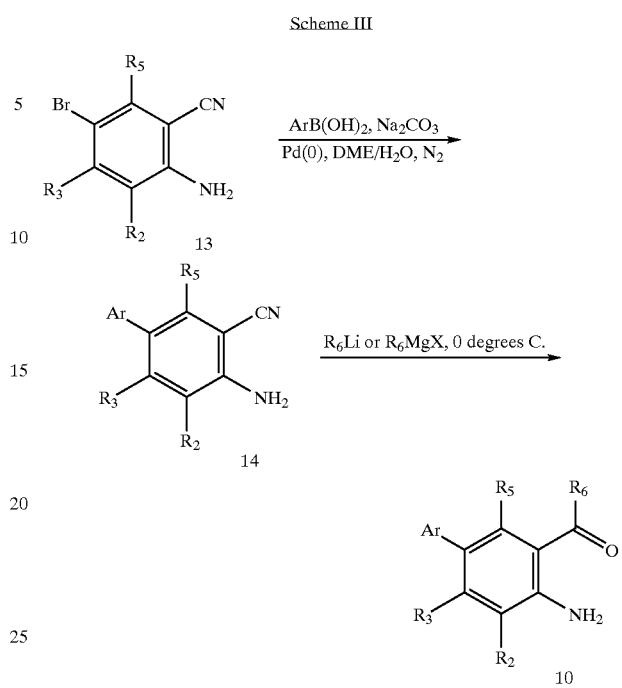

Scheme IV depicts an approach to prepare benzoxazinones with a low perfluoroalkyl substituent at position-4, e.g. $R_6$ is trifluororrmethyl group. An appropriately substituted chloroaniline 15 was protected with a suitable protective reagent such as pivaloyl chloride or di-tert-butyl pyrocarbonate to give protected aniline 16 in a suitable solvent such as acetonitrile, acetone, THF, methylene chloride, or a mixture of solvent such as methylene chloride and water under an inert atmosphere such as argon or nitrogen at temperatures ranging from 0° C. to 70° C. A suitable base such as sodium carbonate, sodium bicarbonate, or potassium carbonate may be needed when the reaction produces an acid as a side-product such as hydrochloride. Treatment of 16 with an appropriate alkyllithium such as n-butyllithium or s-butyllithium followed by reaction with a low perfluorocarboxy derivatives, e.g., trifluoroacetyl chloride, 1-(trifluoroacetyl)-imidazole, or ethyl trifluoroacetate in a nonprotic solvent such as ether or THF under an inert atmosphere such as argon or nitrogen at −78° C. to ambient temperature gives the protective ortho-amino ketones. Subsequent removal of the protecting group can be effected by reaction of protected amino ketones with a suitable acid such as TFA, 3N aqueous hydrochloride solution in a suitable solvent such as methylene chloride or water at 0° C. to boiling point of the solvent to afford ortho-amino ketone 17. The preparation of 6-chlorobenzoxazinones 19 from 17 can be accomplished in the same fashion as described for the synthesis of benzoxazinone 12 from ketone 10. Coupling of 19 with an aryl group to yield the compounds of this invention, 12 as shown in scheme IV can be effected by a nickel complex catalyzed coupling reaction. The palladium catalysts proved not to be an efficient catalyst in this coupling process. The coupling reaction of 19 with an appropriate aryl boronic acid can be accomplished in the presence of a suitable base such as potassium phosphate and a catalyst of nickel (0 or II) complex, e.g. a nickel complex of dppe, dppf, or triphenylphosphine. The most commonly used solvents in the reaction include dioxane or THF. The coupling reaction is generally executed under an inert atmosphere such as nitrogen or argon at temperatures ranging from ambient temperature to 95° C.

Scheme IV

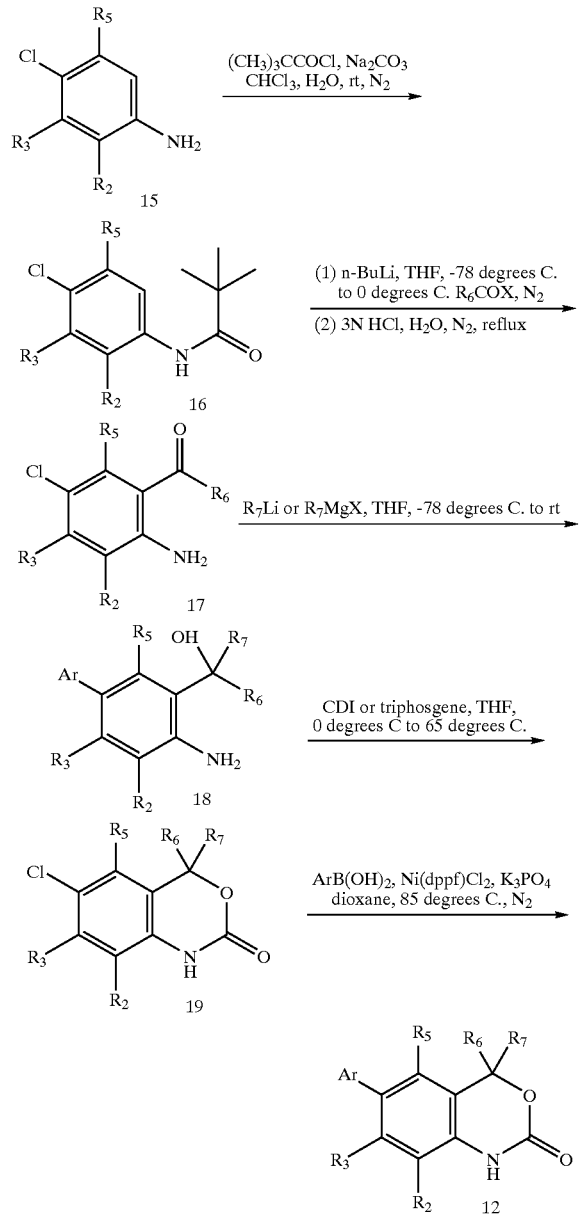

As illustrated in scheme V, the antiprogestin compounds 6 or 12 can be further derivatized at position-1 via numerous approaches leading to a variety of novel cyclocarbamate derivatives including 1-alkyl, 1-substituted alkyl, 1-carbonyl, 1-substituted carbonyl, 1-carboxy, and substituted 1-carboxy derivatives. For example, alkyl or substituted alkyl derivatives 20 can be effected by treatment of carbamate 12 or 6 with a suitable base such as sodium hydride in suitable solvent such as DMF under an inert atmosphere such as argon or nitrogen followed by addition of an appropriate electrophile such as alkyl or substituted alkyl bromide, iodide, or triflate. Such transformation of 12 or 6 at position-1 can also be effected using biphasic condition as indicated in scheme V in which alkylation is executed using a biphasic catalyst such as tributylammonium bromide in a suitable solvent such as acetonitrile. A further example of such modification includes but is not limited to the one depicted in scheme V in that heating of 12 or 6 with triethyl orthoformate affords 1-substituted derivatives of compound 12 or 6.

Scheme V

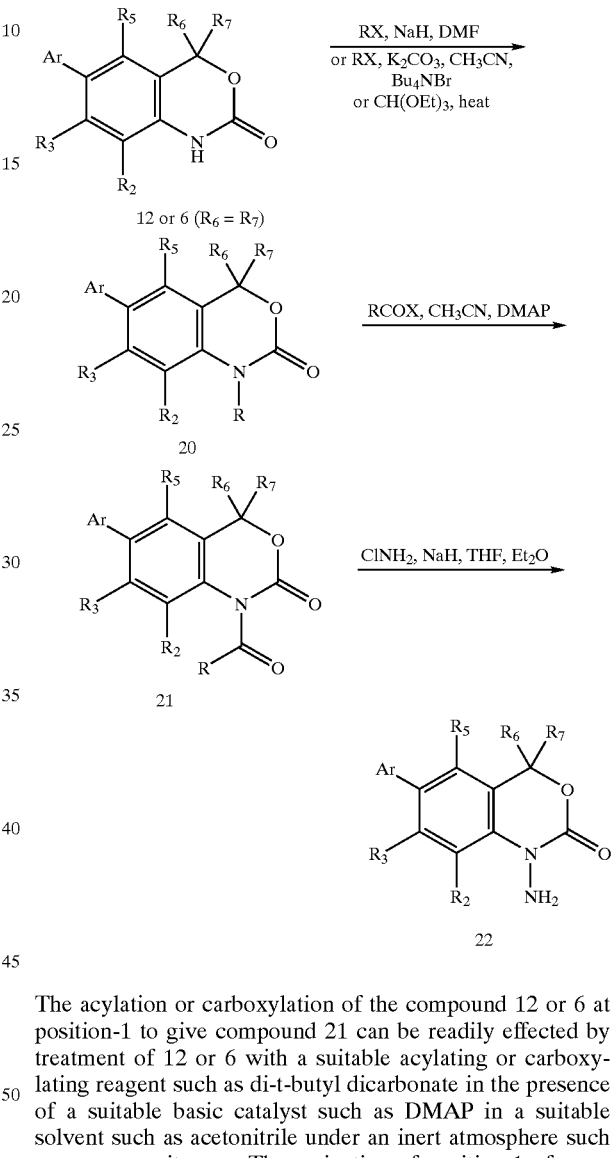

The acylation or carboxylation of the compound 12 or 6 at position-1 to give compound 21 can be readily effected by treatment of 12 or 6 with a suitable acylating or carboxylating reagent such as di-t-butyl dicarbonate in the presence of a suitable basic catalyst such as DMAP in a suitable solvent such as acetonitrile under an inert atmosphere such as argon or nitrogen. The amination of position-1 of compound 12 or 6 can be furnished using a suitable aminating reagent such as chloroamine in the presence of a suitable base such as sodium hydride in a suitable solvent such as THF or diethyl ether following the literature procedure (Metlesics et al. *J. Org. Chem.* 30, 1311(1965)).

EXAMPLE 1

2-(2-Amino-5-bromophenyl)propan-2-ol

A solution of 2-amino-5-bromobenzoic acid (10 g, 46 mmol) in dry THF (200 mL) was treated at −78° C. under nitrogen with a solution of methylmagnesium bromide in ether (3.0 M, 90 mL, 270 mmol). The reaction mixture was slowly warmed to ambient temperature, kept stirring for 48 hours under nitrogen and then poured into a cold 0.5 N aqueous hydrochloride solution (300 mL). The mixture was neutralized with aqueous 1 N sodium hydroxide solution and ethyl acetate (300 mL) was added. The organic layer was separated and aqueous layer was extracted with ethyl acetate (3×100 mL). The combined organic layers were washed with brine and dried (MgSO$_4$). After removal of solvent in vacuo, the residue was purified by a silica gel flash chromatography (hexane:ethyl acetate/3:2) to give 2-(2-amino-5-bromophenyl)propan-2-ol as off-white solid (6 g, 57%): mp 62–63° C.; $^1$H-NMR (CDCl$_3$) δ7.19 (d, 1H, J=2.3 Hz), 7.12 (dd, 1H, J=8.4, 2.3 Hz), 6.51 (d, 1H, J=8.4 Hz), 4.70 (s, 2H), 1.82 (s, 1H), 1.65 (s, 6H).

EXAMPLE 2

6-Bromo-4,4-dimethyl-1,4-dihydro-benzo[d][1,3]oxazin-2-one

To a solution of 2-(2-amino-5-bromophenyl)propan-2-ol (18 g, 78 mmol) in dry THF (150 mL) was added 1,1'-carbonyldiimidazole (15.5 g, 94 mmol) under nitrogen. The reaction solution was heated at 50° C. overnight. The solvent was removed in vacuo and the residue was dissolved in ethyl acetate (100 mL). The solution was washed with 1N aqueous hydrochloride solution (2×40 mL), brine (20 mL), and dried with MgSO$_4$. After removal of solvent in vacuo, 6-bromo-4,4-dimethyl-1,4-dihydro-benzo[d][1,3]oxazin-2-one was obtained as a white solid (20 g, 100%): mp 199–200° C.; $^1$H-NMR (DMSO-d$_6$) δ10.32 (s, 1H, D$_2$O exchangeable), 7.48 (d, 1H, J=2.1 Hz), 7.43 (dd, 1H, J=8.5, 2.1 Hz), 6.84 (d, 1H, J=8.4 Hz), 1.61 (s, 6H).

EXAMPLE 3

6-Iodo-4,4-dimethyl-1,4-dihydro-benzo[d][1,3]oxazin-2-one

Prepared from 2-amino-5-iodobenzoic acid following the procedure of Example 1 and 2. White solid: mp 196–197° C.; $^1$H-NMR (DMSO-d$_6$) δ10.30 (s, 1H, D$_2$O exchangeable), 7.58 (m, 2H), 6.71 (d, 1H, J=8.4 Hz), 1.58 (s, 6H). MS (EI) m/z 326 ([M+Na]$^+$, 100%). Anal. Calc. For C$_{10}$H$_{10}$INO$_2$: C, 39.63; H, 3.33; N, 4.62. Found: C, 39.25; H, 3.24; N, 4.49.

EXAMPLE 4

(1,4-Dihydro-4,4-dimethyl-2-oxo-2H-3,1-benzoxazin-6-yl)boronic acid

To a solution of 6-bromo-4,4-dimethyl-1,4-dihydro-benzo[d][1,3]oxazin-2-one (2 g, 7.8 mmol) in anhydrous THF (60 mL) was added a solution of n-BuLi in hexane (10 M, 2.4 mL, 24 mmol) at −78° C. under nitrogen. After stirring at −78° C. for 30 minutes, a slurry was obtained and treated with trisopropyl borate (6.5 mL, 28 mmol). The reaction medium was slowly warmed to ambient temperature and quenched with 1N aqueous hydrochloric acid solution (60 mL). Ethyl acetate (100 mL) was added and organic layer was separated, and aqueous layer was extracted with ethyl acetate (3×60 mL). The combined organic layer was washed with brine and dried with MgSO$_4$. The solvent was removed in vacuo and the residue was purified by a silica gel flash chromatography (ethyl acetate:hexane/2:1) to afford (1,4-dihydro-4,4-dimethyl-2-oxo-2H-3,1-benzoxazin-6-yl)boronic acid as a white solid (1.4 g, 81%): mp 249–250° C.; $^1$H-NMR (DMSO-d$_6$) δ10.21 (s, 1H, D$_2$O exchangeable), 7.90–7.95 (br s, 2H, D$_2$O exchangeable), 7.67 (m, 2H), 6.79 (d, 1H, J=7.8 Hz), 1.61 (s, 6H); MS (ESI) m/z 222 ([M+H]$^+$, 87%).

EXAMPLE 5

6-(3-Chlorophenyl)-4,4-dimethyl-1,4-dihydrobenzo[d][1,3]oxazin-2-one (Procedure A)

A mixture of 6-bromo-4,4-dimethyl-1,4-dihydro-benzo[d][1,3]oxazin-2-one (1.5 g, 5.9 mmol), 3-chlorophenyl boronic acid (1.83 g, 11.7 mmol), tetrakis(triphenylphosphine)-palladium (0) (0.35 g, 0.3 mmol), and sodium carbonate (2.48 g, 23.4 mmol) in a mixture of DME and water (40 mL/10 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (50 mL) was added and organic layer was separated. The aqueous layer was extracted with ethyl acetate (3×15 mL). The combined organic layers were washed with brine and dried with MgSO$_4$. The solvent was removed in vacuo and the residue was purified by a silica gel flash chromatography (hexane:ethyl acetate/2:1) to afford 6-(3-chlorophenyl)-4,4-dimethyl-1,4-dihydrobenzo[d][1,3]oxazin-2-one as a yellowish solid (1.4 g, 82%): mp 158–159° C.; $^1$H-NMR (DMSO-d$_6$) δ10.31 (s, 1H, D$_2$O exchangeable), 7.75 (s, 1H), 7.61 (m, 3H), 7.46 (t, 1H, J=7.9 Hz), 7.39 (dd, 1H, J=7.0, 1.1 Hz), 6.96 (d, 1H, J=8.6 Hz), 1.68 (s, 6H); Anal. Calc. For C$_{16}$H$_{14}$ClNO$_2$.0.1 H$_2$O: C, 66.37; H, 4.94; N, 4.84. Found: C, 66.14; H, 4.61; N, 4.71.

EXAMPLE 6

6-(3-Methoxy-phenyl)-4,4-dimethyl-1,4-dihydro-benzo[d][1,3]-oxazin-2-one

Prepared according to Procedure A from 6-bromo-4,4-dimethyl-1,4-dihydro-benzo[d][1,3]oxazin-2-one and 3-methoxyphenyl boronic acid. Yellow solid: mp 164–165° C.; $^1$H-NMR (DMSO-d$_6$) δ10.3 (s, 1H), 7.56 (m, 2H), 7.36 (t, 1H, J=7.89 Hz), 7.20 (m, 2H), 6.96 (d, 1H, J=8.88 Hz), 6.91 (dd, 1H, J=8.13, 2.35 Hz), 3.8 (s, 3H), 1.7 (s, 6H); MS (ESI) m/z 284 ([M+H]$^+$, 30%); Anal. Calc. For C$_{17}$H$_{17}$NO$_3$: C, 72.07; H, 6.05; N, 4.94. Found: C, 70.58; H, 5.73; N, 4.67

EXAMPLE 7

6-(2-Chloro-phenyl)-4,4-dimethyl-1,4-dihydro-benzo[d][1,3]oxazin-2-one

Prepared according to Procedure A from 6-bromo-4,4-dimethyl-1,4-dihydro-benzo[d][1,3]oxazin-2-one and 2-chlorophenyl boronic acid. White solid: mp 181–182° C.; MS (ESI) m/z 288 ([M+H]$^+$, 70%); Anal. Calc. For C$_{16}$H$_{14}$ClNO$_2$: C, 66.79, H, 4.90; N, 4.87. Found: C, 66.78; H, 4,82; N, 4.55

EXAMPLE 8

6-(4-Chloro-phenyl)-4,4-dimethyl-1,4-dihydro-benzo[d][1,3]-oxazin-2-one

Prepared according to Procedure A from 6-bromo-4,4-dimethyl-1,4-dihydro-benzo[d][1,3]oxazin-2-one and 4-chlorophenyl boronic acid. White solid: mp 255–257° C.; $^1$H-NMR (DMSO-d$_6$) δ10.3 (s, 1H), 7.7 (d, 2H, J=8.52 Hz), 7.55 (m, 2H), 7.5 (d, 2H, J=8.52 Hz), 6.96 (d, 1H, J=8.52 Hz), 1.7 (s, 6H); MS (ESI) m/z 288 ([M+H]$^+$, 70%); Anal. Calc. For C$_{16}$H$_{14}$ClNO$_2$: C, 66.79; H, 4.90; N, 4.87. Found: C, 66.34; H, 4.76; N, 4.75

EXAMPLE 9

6-(3-Chloro-phenyl)-4-methyl-1,4-dihydro-benzo[d][1,3]oxazin-2-one

To a solution of 1-(4-amino-3'-chloro-biphenyl-3-yl)-ethanone (see example 35, 0.15 g, 0.61 mmol) in anhydrous methanol was added sodium borohydride (0.07 g, 1.03 mmol) at room temperature (rt) under nitrogen. After 15 minutes, the reaction mixture was treated with ice-water. Ethyl acetate (30 mL) was added, organic layer was separated, and aqueous layer was extracted with ethyl acetate (3×20 mL). The combined organic layers were washed with brine (10 mL) and dried over $MgSO_4$. After removal of solvent, the residue obtained was crystallized from toluene to afford 1-(4-amino-3'-chloro-biphenyl-3-yl)-ethanol as white solid (0.087 g, 58%): $^1$H-NMR (DMSO-$d_6$) δ7.55 (t, 1H, J=1.4 Hz), 7.50 (d, 1H, J=7.8 Hz), 7.44 (d, 1H, J=2.1 Hz), 7.39 (t, 1H, J=8.2 Hz), 7.31–7.21 (m, 2H), 6.68 (d, 1H, J=8.1 Hz), 5.25 (s, 2H), 5.20 (m, 1H), 4.83 (m, 1H), 1.35 (d, 3H, J=8.8 Hz); MS (EI) m/z 247 (M$^+$).

A mixture of 1-(4-amino-3'-chloro-biphenyl-3-yl)-ethanol (0.03 g, 0.13 mmol) and triphosgene (0.01 g, 0.04 mmol) in dry THF (3 mL) was stirred under a blanket of nitrogen for 10 minutes. The solvent was removed to give 6-(3-chloro-phenyl)-4-methyl-1,4-dihydro-benzo[d][1,3]oxazin-2-one as a white solid (0.031 g, 91%): mp 155–156° C.; $^1$H-NMR (DMSO-$d_6$) δ10.3 (s, 1H), 7.72 (m, 1H), 7.62 (m, 2H), 7.56 (m, 1H), 7.47 (t, 1H, J=8.00 Hz), 7.39 (d, 1H, J=8.0 Hz), 6.98 (d, 1H, J=8.0 Hz), 5.50 (q, 1H, J=6.82 Hz), 1.6 (d, 3H, J=6.82 Hz); MS (APCI) m/z 274 ([M+H]$^+$, 100%)

EXAMPLE 10

6-(3-Chloro-phenyl)-4-ethyl-1,4-dihydro-benzo[d][1,3]oxazin-2-one

Prepared according to the procedure of Example 9 from 1-(4-amino-3'-chloro-biphenyl-3-yl)-propanol and triphosgene. White solid: mp 146–148° C.; $^1$H-NMR (DMSO-$d_6$) δ10.3 (s, 1H), 7.70 (m, 1H), 7.60 (m, 3H), 7.47 (t, 1H, J=8.22 Hz), 7.39 (d, 1H, J=8.28 Hz), 6.97 (d, 1H, J=8.22 Hz), 5.4 (t, 1H, J=10.9 Hz), 1.9 (m, 2H), 0.97 (t, 3H, J=7.68 Hz); MS (ESI) m/z 286 ([M–H]$^-$, 100%)

EXAMPLE 11

6-(3-Chloro-phenyl)-4-phenyl-1,4-dihydro-benzo[d][1,3]oxazin-2-one

Prepared from 1-(4-amino-3'-chloro-biphenyl-3-yl)-benzyl alcohol and triphosgene according to the procedure of Example 9. Off-white solid: mp 177–178° C.; $^1$H-NMR (DMSO-$d_6$) δ10.5 (s, 1H), 7.68 (dd, 1H, J=8.7, 1.7 Hz), 7.62 (t, 1H, J=1.74 Hz), 7.54–7.5 (m, 1H), 7.48–7.34 (m, 8H), 7.04 (d, 1H, J=8.7 Hz), 6.6 (s, 1H); MS (ESI) m/z 336 ([M+H]$^+$, 30%)

EXAMPLE 12

3-(4,4-Dimethyl-2-oxo-1,4-dihydro-2H-benzo[d][1,3]oxazin-6-yl)-benzonitrile (Procedure B)

A mixture of (1,4-dihydro-4,4-dimethyl-2-oxo-2H-3,1-benzoxazin-6-yl)boronic acid (2.22 g, 10 mmol), 3-bromobenzonitrile (2.18 g, 12 mmol), tetrakis(triphenylphosphine)palladium (0) (0.6 g, 0.52 mmol), and sodium carbonate (2.2 g, 21 mmol) in a mixture of DME and water (70 mL/15 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (100 mL) was added and organic layer was separated. The aqueous layer was extracted with ethyl acetate (3×30 mL). The combined organic layers were washed with brine and dried with $MgSO_4$. The solvent was removed in vacuo and the residue was purified by a silica gel flash chromatography (hexane:ethyl acetate/1:1) to give 3-(4,4-dimethyl-2-oxo-1,4-dihydro-2H-benzo[d][1,3]oxazin-6-yl)-benzonitrile as an off-white solid (0.7 g, 25%): mp 236–237° C.; $^1$H-NMR (DMSO-$d_6$) δ10.34 (s, 1H, $D_2O$ exchangeable), 8.21 (s, 1H), 8.02 (d, 1H, J=8.1 Hz), 7.79 (d, 1H, J=7.7 Hz), 7.60–7.70 (m, 3H), 6.98 (d, 1H, J=8.2 Hz), 1.71 (s, 6H); Anal. Calc. For $C_{17}H_{14}N_2O_2 \cdot 0.1 H_2O$: C, 72.89; H, 5.11; N, 10.00. Found: C, 72.75; H, 5.05; N, 9.65.

EXAMPLE 13

4,4-Dimethyl-6-(3-nitrophenyl)-1,4-dihydrobenzo[d][1,3]oxazin-2-one

Prepared from 6-iodo-4,4-dimethyl-1,4-dihydro-benzo[d][1,3]oxazin-2-one and 3-nitrophenyl boronic acid according to Procedure A. Yellowish solid: mp 244–245° C.; $^1$H-NMR (DMSO-$d_6$) δ10.38 (s, 1H, $D_2O$ exchangeable), 8.47 (s, 1H), 8.14–8.20 (m, 2H), 7.70–7.76 (m, 3H), 7.01 (d, 1H, J=8.1 Hz), 1.68 (s, 6H); MS (EI) m/z 297 ([M–H]$^-$, 100%). Anal. Calc. For $C_{16}H_{14}N_2O_4$: C, 64.42; H, 4.73; N, 9.39. Found: C, 63.93; H, 4.91; N, 8.71

EXAMPLE 14

6-(3-Bromo-5-fluorophenyl)-4,4-dimethyl-1,4-dihydrobenzo[d][1,3]oxazin-2-one Prepared from (1,4-dihydro-4,4-dimethyl-2-oxo-2H-3,1-benzoxazin-6-yl)boronic acid and 1,3-dibromo-5-fluorobenzene following Procedure B. White solid: mp 182–183° C.; $^1$H-NMR (DMSO-$d_6$) δ10.36 (s, 1H, $D_2O$ exchangeable), 7.78 (s, 1H), 7.58–7.65 (m, 3H), 7.49 (dd, 1H, J=8.3, 1.8 Hz), 6.96 (d, 1H, J=8.5 Hz), 1.69 (s, 6H); $^{19}$F-NMR (DMSO-$d_6$) δ–112.46 (m, 1F); MS (CI) m/z 352 ([M+H]$^+$, 78%), 350 ([M+H]$^+$, 75%). Anal. Calc. For $C_{16}H_{13}BrFNO_2$: C, 54.88; H, 3.74; N, 4.00. Found: C, 54.83; H, 3.82; N, 3.95

EXAMPLE 15

3-(4,4-Dimethyl-2-oxo-1,4-dihydro-2H-benzo[d][1,3]oxazin-6-yl)-5-fluorobenzonitrile A mixture of 6-(3-bromo-5-fluorophenyl)-4,4-dimethyl-2H-benz[d][1,3]oxazin-2-one (1 g, 2.8 mmol), zinc cyanide (0.2 g, 1.7 mmol), and tetrakis(triphenylphosphine)-palladium (0) (0.2 g, 0.17 mmol) in dry DMF (20 mL) was degassed to remove oxygen and then was heated at 85° C. under a blanket of nitrogen for 6.5 hours. The reaction solution was cooled to room temperature and poured onto a cold saturated aqueous ammonium chloride solution (100 mL). The white precipitate appeared and was collected on a filter. The white solid was washed with the distilled water (3×20 mL) and dissolved in a mixture of ethyl acetate (10 mL) and methanol (10 mL). The solution was applied on a pad of silica gel and eluted with a mixture of ethyl acetate and hexane (1:1). After evaporation, 3-(4,4-dimethyl-2-oxo-1,4-dihydro-2H-benzo[d][1,3]oxazin-6-yl)-5- fluorobenzonitrile was obtained as a white solid (0.7 g, 84%): mp 253–254° C.; $^1$H-NMR (DMSO-d$_6$) δ10.4 (s, 1H, D$_2$O exchangeable), 8.13 (s, 1H), 7.92 (m, 1H), 7.82 (m, 1H), 7.73 (m, 2H), 6.98 (d, 1H, J=8.2 Hz), 1.68 (s, 6H); $^{19}$F-NMR (DMSO-d$_6$) δ–112.25 (m, 1F); MS (EI) m/z 296 (M$^+$, 65%); Anal. Calc. For C$_{17}$H$_{13}$FN$_2$O$_2$: C, 68.91; H, 4.42; N, 9.45. Found: C, 68.85; H, 4.58; N, 9.14.

EXAMPLE 16

5-(4,4-Dimethyl-2-oxo-1,4-dihydro-2H-benzo[d][1,3]oxazin-6-yl)-nicotinonitrile

Prepared from (1,4-dihydro-4,4-dimethyl-2-oxo-2H-3,1-benzoxazin-6-yl) boronic acid and 3-bromo-5-cyanopyridine according to Procedure B. Off-white solid: mp 290–291° C.; $^1$H-NMR (DMSO-d$_6$) δ10.41 (s, 1H, D$_2$O exchangeable), 9.21 (d, 1H, J=2.2 Hz), 8.97 (d, 1H, J=1.7 Hz), 8.68 (t, 1H, J=2.1 Hz), 7.76 (m, 2H), 7.01 (d, 1H, J=8.2 Hz), 1.70 (s, 6H); MS (ESI) m/z 278 (M–H, 96%). Anal. Calc. For C$_{16}$H$_{13}$N$_3$O$_2$.0.2 H$_2$O: C, 67.94; H, 4.77; N, 14.85. Found: C, 68.04; H, 4.70; N, 14.58.

EXAMPLE 17

4-(4,4-Dimethyl-2-oxo-1,4-dihydro-2H-benzo[d][1,3]oxazin-6-yl)-thiophene-2-carbonitrile Prepared from (1,4-dihydro-4,4-dimethyl-2-oxo-2H-3,1-benzoxazin-6-yl)boronic acid and 4-bromo-2-thiophenecarbonitrile according to Procedure B. Yellowish solid: mp 230–231° C. (decomposed); $^1$H-NMR (CDCl$_3$) δ8.32 (s, 1H, D$_2$O exchangeable), 7.83 (d, 1H, J=1.5 Hz), 7.61 (d, 1H, J=1.4 Hz), 7.43 (dd, 1H, J=8.2, 1.9 Hz), 7.29 (d, 1H, J=1.8 Hz), 6.85 (d, 1H, J=8.2 Hz), 1.78 (s, 6H); MS (EI) m/z 283(M–H, 100%). Anal. Calc. For C$_{15}$H$_{12}$N$_2$O$_2$S.0.2 H$_2$O: C, 62.57; H, 4.34, N, 9.73. Found: C, 62.48; H, 4.31; N, 9.64.

EXAMPLE 18

5-Bromo-2-thiophenecarbonitrile

A mixture of 5-bromo-2-thiophenecarboxaldehyde (96.0 g, 500 mmol), hydroxylamine hydrochloride (111.9 g, 500 mmol), pyridine (500 mL), and ethanol (500 mL) was heated under nitrogen at reflux for two hours. The reaction mixture was cooled to ambient temperature and concentrated in vacuo to give an oil. The crude product was triturated twice with ice water and the solid obtained was collected on a filter. A mixture of a portion of the above solid (44.31 g, 215 mmol), copper (II) acetate monohydrate (4.2 g, 21 mmol) in acetonitrile (1.4 L) was heated at reflux for three hours. The solvent was removed in vacuo and the residue was dissolved in ethyl acetate. The solution was washed with 5% aqueous sulfuric acid (2×30 mL), water (2×30 mL), brine (20 mL), and dried (MgSO$_4$). The solvent was removed in vacuo and the residue was dissolved in a minimum amount of chloroform (1 L) and allowed to crystallize. The crystal obtained was collected on a filter and the filtrate was concentrated and purified by a chromatography (silica gel, chloroform) to give the title compound as an off-white solid (31.5 g combined, 58%). IR (film) cm$^{-1}$ 2200. $^1$H-NMR (CDCl$_3$) δ7.39–7.38 (d, 1H, J=4.1 Hz), 7.10 (d, 1H, J=4.0 Hz); MS (EI) m/z 187 (M$^+$, 98%) 189(M$^+$, 100%).

EXAMPLE 19

5-Bromo-4-methyl-2-thiophene carboxaldehyde

To a solution of diethylamine (28 g, 0.383 mol) in anhydrous THF (400 mL) was added at –40° C. under nitrogen a solution of n-BuLi (2.5 M, 153 mL, 0.383 mol) in hexane. After addition, the solution was stirred at –40° C. under nitrogen for 30 minutes, cooled to –78° C. and treated dropwise with a solution of 2-bromo-3-methylthiophene (45 g, 0.254 mol) in anhydrous THF (450 mL). The reaction solution was stirred at –78° C. for 30 minutes and treated with anhydrous DMF (100 mL). The mixture was allowed to warm to ambient temperature and was quenched with 1N aqueous hydrochloride solution (1 L). The solution was extracted with ethyl acetate(3×450 mL). The extracts were washed with water, brine and dried (MgSO$_4$). After removal of solvent in vacuo, the title compound was obtained as a white solid (46 g, 88.3%). A sample of the product was crystallized from hexane: mp 63–65° C.; IR (KBr) 1654 cm$^{-1}$. $^1$H-NMR (CDCl$_3$) δ9.75 (s, 1H), 7.45 (s, 1H), 2.26 (s, 3H); MS (EI) m/z 204/206 (M$^+$). Anal. Calc. For C$_6$H$_5$BrOS: C, 35.14; H, 2.46. Found: C, 35.00; H, 2.44.

EXAMPLE 20

5-Bromo-4-methyl-2-thiophenecarbonitrile

Prepared from 5-bromo-4-methyl-2-thiophene carboxaldehyde using the procedure of Example 18. White solid: mp 40–42° C.; IR (KBr) 2200 cm$^{-1}$; $^1$H-NMR (CDCl$_3$) δ7.29 (s, 1H), 2.21 (s, 3H). MS (EI) m/z 201/203 (M$^+$, 98%/100%); Anal. Calc. For C$_6$H$_4$BrNS: C, 35.66; H, 1.99; N, 6.93. Found: C, 36.00; H, 2.14; N, 6.76.

EXAMPLE 21

5-(4,4-Dimethyl-2-oxo-1,4-dihydro-2H-benzo[d][1,3]oxazin-6-yl)-thiophene-2-carbonitrile Prepared according to Procedure B from 5-bromo-2-thiophenecarbonitrile and (1,4-dihydro-4,4-dimethyl-2-oxo-2H-3,1-benzoxazin-6-yl)boronic acid. Off-white solid: mp 264–266° C. $^1$H-NMR (DMSO-d$_6$) δ10.3 (s, 1H), 7.97 (d, 1H, J=7.9 Hz), 7.60–7.66 (m, 3H). 6.96 (d, 1H, J=8.1 Hz), 1.65 (S, 6H). MS (APCI) m/z 285 (M+H)$^+$, 302 (M+NH$_4$)$^+$. Anal. Calc. For C$_{15}$H$_{12}$N$_2$O$_2$S: C, 63.36; H, 4.25; N, 9.85. Found: C, 63.01; H, 4.36; N, 9.39.

EXAMPLE 22

5-(4,4-Dimethyl-2-oxo-1,4-dihydro-2H-benzo[d][1,3]oxazin-6-yl)-4-methyl-thiophene-2-carbonitrile Prepared according to Procedure B from (1,4-dihydro-4,4-dimethyl-2-oxo-2H-3,1-benzoxazin-6-yl)boronic acid and 5-bromo-4-methyl-2-thiophenecarbonitrile. Off-white solid: mp 195–200° C. $^1$H-NMR (DMSO-d$_6$) δ10.2 (s, 1H), 8.32 (s, 1H), 7.41–7.44 (m, 2H), 7.01 (d, 1H, J=8.8 Hz), 2.28 (s, 3H), 1.64 (s, 6H); MS (APCI) m/z 299 [M+H]$^+$. Anal. Calc. For C$_{16}$H$_{14}$N$_2$O$_2$S; C, 64.41; H, 4.75; N, 8.89. Found: C, 64.64; H, 4.62; N, 9.39.

EXAMPLE 23

4-(4,4-Dimethyl-2-oxo-1,4-dihydro-2H-benzo[d][1,3]oxazin-6-yl)-furan-2-carbonitrile Prepared from (1,4-dihydro-4,4-dimethyl-2-oxo-2H-3,1-benzoxazin-6-yl)boronic acid and 4-bromo-2-furancarbonitrile according to Procedure B. Off-white solid: mp 255–256° C. $^1$H-NMR (DMSO-d$_6$) δ10.32 (s, 1H, D$_2$O exchangeable), 8.57 (s, 1H), 8.15 (s, 1H), 7.61 (s, 1H), 7.55 (dd, 1H, J=8.3, 1.5 Hz), 6.92 (d, 1H, J=8.2 Hz), 1.65 (s, 6H); MS (ESI) m/z 269(M+H, 72%). Anal. Calc. For C$_{15}$H$_{12}$N$_2$O$_3$: C, 67.16; H, 4.51; N, 10.44. Found: C, 67.14; H, 4.59; N, 10.07.

EXAMPLE 24

4,4-Diethyl-6-(3-nitrophenyl)-1,4-dihydrobenzo[d][1,3]oxazin-2-one

Prepared from 4,4-diethyl-6-iodo-1,4-dihydrobenzo[d][1,3]oxazin-2-one and 3-nitrophenyl boronic acid according to Procedure A. Off-white solid: mp 193–194° C. $^1$H-NMR (CDCl$_3$) δ9.19 (s, 1H, D$_2$O exchangeable), 8.38 (t, 1H, J=1.9 Hz), 8.20 (m, 1H), 7.83 (m, 1H), 7.61 (t, 1H, J=8.0 Hz), 7.50 (dd, 1H, J=8.2, 2.0 Hz), 7.23 (d, 1H, J=1.7 Hz), 6.99 (d, 1H, J=8.3 Hz), 2.09 (q, 4H, J=7.4 Hz), 0.96 (t, 6H, J=8.3 Hz); MS (EI) m/z 325 ([M−H]$^-$, 100%). Anal. Calc. For C$_{18}$H$_{18}$N$_2$O$_4$·0.3 H$_2$O: C, 65.17; H, 5.65; N, 8.44. Found: C, 65.31; H, 5.60; N, 8.10.

EXAMPLE 25

6-(3-Chlorophenyl)-4,4-diethyl-1,4-dihydrobenzo[d][1,3]oxazin-2-one

Prepared from 4,4-diethyl-6-iodo-1,4-dihydrobenzo[d][1,3]oxazin-2-one and 3-chlorophenyl boronic acid according to Procedure A. White solid: mp 150–151° C. $^1$H-NMR (CDCl$_3$) δ8.52 (s, 1H, D$_2$O exchangeable), 7.50 (s, 1H), 7.31–7.44 (m, 4H), 7.16 (d, 1H, J=1.5 Hz), 6.89 (d, 1H, J=8.2 Hz), 2.03 (m, 4H), 0.94 (t, 6H, J=7.4 Hz); MS (EI) m/z 315(M$^+$, 53%). Anal. Calc. For C$_{18}$H$_{18}$ClNO$_2$: C, 68.46; H, 5.75; N, 4.44. Found: C, 68.16; H, 5.81; N, 4.32.

EXAMPLE 26

1-(2-Amino-5-bromo-phenyl)cyclohexanol

Prepared according to the procedure of Example 1 from 2-amino-5-bromobenzoic acid and the Grignard reagent prepared from 1,5-dibromopentane. A clear oil: $^1$H-NMR (DMSO-d$_6$) δ7.07 (d, 1H, J=2.3 Hz), 7.03 (dd, 1H, J=8.4, 2.4 Hz), 6.55 (d, 1H, J=8.6 Hz), 5.49 (s, 2H, D$_2$O exchangeable), 5.00 (s, 1H, D$_2$O exchangeable), 2.01 (d, 2H, J=1.8 Hz), 1.66–1.77 (m, 2H), 1.44–1.61 (m, 4H), 1.16–1.34 (m, 2H). MS (ESI) m/z 270/272 ([M+H]$^+$, 98%/100%).

EXAMPLE 27

6-Bromo-spiro[4H-3,1-benzoxazine-4,1'-cyclohexane]-2-(1H)-one

Prepared from 1-(2-amino-5-bromo-phenyl)cyclohexanol and carbonyl diimidazole according to the procedure of Example 2. Off-white solid: mp 208–210° C. $^1$H-NMR (DMSO-d$_6$) δ10.26 (s, 1H), 7.45 (d, 1H, J=2.2 Hz), 7.39 (dd, 1H, J=8.2, 2.2 Hz), 6.81 (d, 1H, J=8.3 Hz), 1.90–1.97 (m, 2H), 1.80–1.85 (m, 5H), 1.25–1.35 (m, 3H); MS (APCI) m/z 296 ([M+H]$^+$, 68%)

EXAMPLE 28

Spiro-(4,1'-cyclohexane-1,4-dihydro-2-oxo-2H-3,1-benzoxazin-6-yl)boronic acid Prepared according to the procedure of Example 4 from 6-bromo-spiro[4H-3,1-benzoxazine-4,1'-cyclohexane]-2-(1H)-one. Off-white solid: mp 223–225° C. $^1$H-NMR (DMSO-d$_6$) δ10.17 (s, 1H, D$_2$O exchangeable), 7.92 (s, 2H, D$_2$O exchangeable), 7.67 (s, 1H), 7.63 (dd, 1H, J=8.0, 1.1 Hz), 6.81 (d, 1H, J=7.9 Hz), 1.96 (s, 1H), 1.93 (s, 1H), 1.57–1.88 (m, 7H), 1.24–1.34 (m, 1H); MS (ESI) m/z 262 (M+H)$^+$.

EXAMPLE 29

6-(3-Chlorophenyl)-spiro[4H-3,1-benzoxazine-4,1'-cyclohexane]-2-(1H)-one

Prepared according to Procedure A from 6-bromo-spiro[4H-3,1-benzoxazine-4,1'-cyclohexane]-2(1H)-one and 3-chlorophenyl boronic acid. Off-white solid: mp 165–168° C. $^1$H-NMR (DMSO-d$_6$) δ10.25 (s, 1H), 7.74 (t, 1H, J=1.9 Hz), 7.50–7.67 (m, 3H), 7.42–7.49 (m 1H), 7.35–7.38 (m, 1H), 6.93–6.95 (d, 1H, J=4.2 Hz), 1.91–1.98 (m, 4H), 1.64–1.76 (m, 3H), 1.60 (m, 2H), 1.29–1.39 (m, 1H); MS (APCI) m/z 328 ([M+H]$^+$, 80%)

EXAMPLE 30

6-Bromo-spiro-[4H-3,1-benzoxazine-4,1'-cyclopentane]-2-(1H)-one

Prepared according to the procedure of Example 26 and 27 from 2-amino-5-bromobenzoic acid and the Grignard reagent prepared from 1,4-dibromobutane. Off-white solid: mp 180–185° C. $^1$H-NMR (DMSO-d$_6$) δ10.29 (s, 1H, D$_2$O exchangeable), 7.45 (d, 1H, J=2.2 Hz), 7.41 (dd, 1H, J=8.1, 2.1 Hz), 6.82 (d, 1H, J=8.0 Hz), 1.96–2.09 (m, 4H), 1.76–1.87 (m, 4H); MS (EI) m/z 281 (M$^+$, 98%). Anal. Calc. For C$_{12}$H$_{12}$BrNO$_2$: C, 51.08; H, 4.29; N, 4.96. Found: C, 50.53; H, 4.21; N, 4.85

EXAMPLE 31

6-(3-Chlorophenyl)-spiro-[4H-3,1-benzoxazine-4,1'-cyclopentane]-2(1H)-one

Prepared from 6-bromo-spiro-[4H-3,1-benzoxazine-4,1'-cyclopentane]-2-(1H)-one and 3-chlorophenyl boronic acid according to Procedure A. Off-white solid: mp 140–145° C. $^1$H-NMR (DMSO-d$_6$) δ10.27 (s, 1H), 7.75 (t, 1H, J=1.8 Hz), 7.53–7.63 (m, 3H), 7.44 (t, 1H, J=7.9 Hz), 7.36 (m, 1H), 6.95 (d, 1H, J=8.6 Hz), 2.09–2.15 (m, 4H), 1.81–1.89 (m, 4H). MS (ESI) m/z 314 [M+H]$^+$. Anal. Calc. For C$_{18}$H$_{16}$ClNO$_2$: C, 68.90; H, 5.14; N, 4.46. Found: C, 60.94; H, 4.94; N, 3.78.

EXAMPLE 32

6-(3-Nitrophenyl)-spiro[4H-3,1-benzoxazine-4,1'-cyclohexan]-2(1H)-one

Prepared from 6-bromo-spiro[4H-3,1-benzoxazine-4,1'-cyclohexane]-2(1H)-one and 3-nitrophenyl boronic acid according to Procedure A. Off-white solid: mp 245–246° C. $^1$H-NMR (CDCl$_3$) δ8.39 (t, 1H, J=1.9 Hz), 8.20 (dd, 1H, J=8.2, 1.4 Hz), 8.11 (s, 1H, D$_2$O exchangeable), 7.86 (d, 1H, J=8.0 Hz), 7.62 (t, 1H, J=8.1 Hz), 7.50 (dd, 1H, J=8.2, 1.9 Hz), 7.39 (d, 1H, J=1.8 Hz), 6.93 (d, 1H, J=8.2 Hz), 2.25 (d, 2H, J=12.7 Hz), 1.60–1.99 (m, 7H), 1.31–1.42 (m, 1H); MS (EI) m/z 337 ([M–H]⁻, 100%). Anal. Calc. For $C_{19}H_{18}N_2O_4 \cdot 0.35H_2O$: C, 66.21; H, 5.47; N, 8.13. Found: C, 66.22; H, 5.43; N, 7.86.

EXAMPLE 33

2-Amino-5-bromo-N-methoxy-N-methylbenzamide

To a mixture of N, O-dimethylhydroxylamine hydrochloride (9.42 g, 96 mmol) and triethyl amine (13.5 mL, 96 mmol) in ethanol and water (100 mL/10 mL) was added a solution of 5-bromoisatoic anhydride (20 g, 74 mmol) in ethanol and water (100 mL/10 mL) at ambient temperature under nitrogen. The reaction mixture was heated at reflux for 3 hours. The solvent was removed in vacuo and the residue was dissolved in ethyl acetate (100 mL), washed with 1N aqueous sodium hydroxide solution (2×20 mL), brine (30 mL), and dried with $MgSO_4$. After removal of solvent, the residue was purified by a silica gel flash chromatography (hexane:ethyl acetate/3:2) to give 2-amino-5-bromo-N-methoxy-N-methylbenzamide as an off-white solid (13 g, 68%): mp 80–81° C.; ¹H-NMR (CDCl₃) δ7.49 (d, 1H, J=2.1 Hz), 7.26 (dd, 1H, J=8.3, 2.0 Hz), 6.59 (d, 1H, J=8.4 Hz), 4.69 (br, 2H), 3.58 (s, 3H), 3.34 (s, 3H); Anal. Calc. For $C_9H_{11}BrN_2O_2$: C, 41.72; H, 4.28; N, 10.81. Found: C, 41.99; H, 4.16; N, 10.82.

EXAMPLE 34

4-Amino-3'-chloro-biphenyl-3-carbonitrile

Prepared from 2-amino-5-bromobenzonitrile and 3-chlorophenyl boronic acid according to procedure A. Off-white solid: mp 118–119° C.; ¹H-NMR (DMSO-d₆) δ7.80 (d, 1H, J=2.3 Hz), 7.65–7.72 (m, 2H), 7.57 (d, 1H, J=8.0 Hz), 7.42 (t, 1H, J=7.9 Hz), 7.31 (m, 1H), 6.87 (d, 1H, J=8.7 Hz), 6.29 (br, 2H); Anal. Calc. For $C_{13}H_9ClN_2$: C, 68.28; H, 3.97; N, 12.25. Found: C, 67.68; H, 4.06; N, 11.89.

EXAMPLE 35

1-(4-Amino-3'-chloro-biphenyl-3-yl)-ethanone

A mixture of 2-amino-5-bromo-N-methoxy-N-methylbenzamide (7.78 g, 30 mmol), 3-chlorophenyl boronic acid (5.63 g, 36 mmol), tetrakis(triphenylphosphine) palladium (0) (1.73 g, 1.5 mmol), and sodium carbonate (7.63 g, 72 mmol) in a mixture of DME and water (150 mL/30 mL) was degassed to remove the oxygen and heated at 85° C. under nitrogen for 3 hours. The reaction mixture was cooled to room temperature and treated with brine (30 mL) and ethyl acetate (100 mL). The organic layer was separated and aqueous layer was extracted with ethyl acetate (3×40 mL). The combined organic layers were washed with brine and dried with $MgSO_4$. After removal of solvent, the residue was purified by a flash chromatography (silica gel, hexane:ethyl acetate/1:1) to give 5-(3-chlorophenyl)-N-methoxy-N-methylbenzamide as a brown oil (5 g, 57%). To a solution of this benzamide (5 g, 17.2 mmol) in anhydrous THF was added in a dropwise fashion a solution of methyllithium in ether (1.4M, 28.6 mL, 40 mL) at –78° C. under nitrogen. After stirred for 30 minutes, the reaction mixture was treated with a saturated aqueous ammonium chloride solution (50 mL) at –78° C. Ethyl acetate (100 mL) was added, organic layer was separated, and aqueous layer was extracted with ethyl acetate (3×20 mL). The combined organic layers were washed (brine) and dried (MgSO₄). After removal of solvent, the residue was purified by a flash chromatography (silica gel, hexane:ethyl acetate/2:1) to afford 1-(4-amino-3'-chloro-biphenyl-3-yl)-ethanone as a yellow solid (2 g, 47%): mp 89–90° C.; ¹H-NMR (CDCl₃) δ7.89 (d, 1H, J=2.0 Hz), 7.51 (m, 2H), 7.25–7.40 (m, 3H), 6.73 (d, 1H, J=8.6 Hz), 6.38 (br, 2H), 2.65 (s, 3H); MS (EI) m/z 268([M+Na]⁺, 60%); Anal. Calc. For $C_{14}H_{12}ClNO$: C, 68.44; H, 4.92; N, 5.70. Found: C, 68.40; H, 4.89; N, 5.61.

EXAMPLE 36

4-Allyl-6-(3-chlorophenyl)-4-methyl-1,4-dihydro-benzo[d][1,3]oxazin-2-one (Procedure C)

To a solution of 1-(4-amino-3'-chloro-biphenyl-3-yl)-ethanone (0.2 g, 0.82 mmol) in anhydrous THF (10 mL) was added a solution of allylmagnesium bromide in ether (1.0 M, 3 mL, 3 mmol) at 0° C. under nitrogen. The reaction solution was slowly warmed to ambient temperature and stirred under nitrogen for 1 hour. A saturated aqueous ammonium chloride solution (10 mL) was added, followed by addition of ethyl acetate (50 mL). The organic layer was separated and aqueous layer was extracted with ethyl acetate (3×10 mL). The combined organic layers were washed with brine and dried with $MgSO_4$. After removal of solvent, the residue was purified by flash chromatography (silica gel, hexane:ethyl acetate/3:1) to afford amino carbinol intermediate which was used in next step without further purification. To a solution of above amino carbinol in anhydrous THF was added CDI (0.38 g, 2.3 mmol) at ambient temperature under nitrogen. The reaction solution was heated at 55° C. for 12 hours and then cooled to room temperature. The solvent was removed in vacuo and the residue was purified by flash chromatography (silica gel, hexane:ethyl acetate/2:1) to yield 4-allyl-6-(3-chlorophenyl)-4-methyl-1,4-dihydro-benzo[d][1,3]oxazin-2-one as a white solid (130 mg from two steps, 52%): mp 128–129° C.; ¹H-NMR (CDCl₃) δ8.68 (s, 1H, D₂O exchangeable), 7.50 (s, 1H), 7.44 (dd, 1H, J=8.2, 1.9 Hz), 7.31–7.40 (m, 3H), 7.25 (d, 1H, J=1.6 Hz), 6.92 (d, 1H, J=8.2 Hz), 5.70–5.85 (m, 1H), 5.17 (m, 2H), 2.76 (m, 2H), 1.79 (s, 3H); MS (ESI) m/z 314 ([M+H]⁺, 40%); Anal. Calc. For $C_{18}H_{16}ClNO_2$: C, 68.90; H, 5.14; N, 4.46. Found: C, 68.90; H, 5.18; N, 4.43.

EXAMPLE 37

6-(3-Chlorophenyl)-4-methyl-4-propyn-1-yl-1,4-dihydro-benzo[d][1,3]oxazin-2-one

Prepared from 1-(4-amino-3'-chloro-biphenyl-3-yl)-ethanone and propynyl-magnesium bromide followed by treatment with CDI according to Procedure C. White solid: mp 184–185° C.; ¹H-NMR (CDCl₃) δ8.18 (s, 1H, D₂O exchangeable), 7.53 (t, 1H, J=1.7 Hz), 7.49 (s, 1H), 7.31–7.48 (m, 4H), 6.92 (d, 1H, J=8.1 Hz), 2.02 (s, 3H), 1.87 (s, 3H); MS (ESI) m/z 304 ([M–H]⁻, 100%); Anal. Calc. For $C_{18}H_{14}ClNO_2$: C, 69.35; H, 4.53; N, 4.49. Found: C, 69.19; H, 4.37; N, 4.41.

EXAMPLE 38

6-(3-Chlorophenyl)-4-ethynyl-4-methyl-1,4-dihydro-benzo[d][1,3]oxazin-2-one

Prepared from 1-(4-amino-3'-chloro-biphenyl-3-yl)-ethanone (0.2 g, 0.82 mmol) and ethynylmagnesium bromide followed by treatment with CDI according to procedure C. Off-white solid: mp 185–186° C.; ¹H-NMR (CDCl₃)

δ 8.18 (s, 1H, D$_2$O exchangeable), 7.53 (t, 1H, J=1.7 Hz), 7.49 (s, 1H), 7.31–7.48 (m, 4H), 6.92 (d, 1H, J=8.1 Hz), 2.81 (s, 1H), 1.87 (s, 3H); MS (ESI) m/z 304 ([M–H]$^-$, 100%); Anal. Calc. For C$_{17}$H$_{12}$ClNO$_2$: C, 68.58; H, 4.06; N, 4.70. Found: C, 68.24; H, 3.94; N, 4.65.

EXAMPLE 39

6-(3-Chlorophenyl)-4-methyl-4-phenyl-1,4-dihydro-benzo[d][1,3]oxazin-2-one

Prepared from 1-(4-amino-3'-chloro-biphenyl-3-yl)-ethanone (0.2 g, 0.82 mmol) and phenylmagnesium bromide followed by treatment with CDI according to Procedure C. White solid: mp 179–180° C.; $^1$H-NMR (CDCl$_3$) δ 8.27 (s, 1H, D$_2$O exchangeable), 7.51–7.57 (m, 2H), 7.28–7.45 (m, 9H), 6.92 (d, 1H, J=8.4 Hz), 2.12 (s, 3H); MS (ESI) m/z 348 ([M–H]$^-$, 100%); Anal. Calc. For C$_{21}$H$_{16}$ClNO$_2$: C, 72.10; H, 4.61; N, 4.00. Found: C, 71.72; H, 4.86; N, 3.91.

EXAMPLE 40

4-Benzyl-6-(3-chloro-phenyl)-4-methyl-1,4-dihydro-benzo[d][1,3]oxazin-2-one

A mixture of 1-(4-amino-3'-chloro-biphenyl-3-yl)-1-benzyl-ethanol (prepared from 1-(4-amino-3'-chloro-biphenyl-3-yl)-ethanone and benzylmagnesium bromide according to Procedure C, 0.14 g, 0.42 mmol) and triphosgene (0.04 g, 0.14 mmol) in dry THF (10 mL) was stirred under a blanket of nitrogen for 10 minutes. Upon completion of the reaction, the THF was removed and the residue purified via flash chromatography (silica gel, 35% ethyl acetate/hexane) to give 4-benzyl-6-(3-chloro-phenyl)-4-methyl-1,4-dihydro-benzo[d][1,3]oxazin-2-one (0.045 g, 30%) as an off-white solid: mp 187–188° C.; $^1$H-NMR (DMSO-d$_6$) δ 10.1 (s, 1H), 7.70 (t, 1H, J=2.3 Hz), 7.6 (d, 1H, J=8.0 Hz), 7.58–7.53 (m, 2H), 7.46 (t, 1H, J=8.0 Hz), 7.38 (d, 1H, J=8.0 Hz), 7.22–7.17 (m, 3H), 7.06–7.0 (m, 2H), 6.84 (d, 1H, J=9.14 Hz), 3.24 (d, 1H, J=14.3 Hz), 3.06 (d, 1H, J=14.3 Hz), 1.68 (s, 3H); MS (ESI) m/z 364 ([M+H]$^+$, 100%); Anal. Calc. For C$_{22}$H$_{18}$ClNO$_2$: C, 72.63; H, 4.99; N, 3.85. Found: C, 71.82; H, 5.09; N, 3.58.

EXAMPLE 41

6-(3-Chloro-phenyl)-4-cyclopropyl-4-methyl-1,4-dihydro-benzo[d][1,3]oxazin-2-one To a solution of cyclopropylmagnesium bromide in anhydrous THF (prepared from cyclopropyl bromide and magnesium metal, 70 mmol) at 52° C. was added under nitrogen 4-amino-3'-chloro-biphenyl-3-carbonitrile (5.2 g, 22.7 mmol). The reaction mixture was stirred at 52° C. for 1 hour, cooled to rt, and quenched with 1N aqueous HCl solution (100 mL). Ethyl acetate (100 mL) was added and the aqueous layer extracted with ethyl acetate (3×40 mL). The combined organic layers were washed with brine and dried over MgSO$_4$. The solvent was removed and the residue was purified via silica gel column (hexane:ethyl acetate/20:1) to give the (4-amino-3'-chloro-biphenyl-3-yl)-cyclopropyl-methanone: $^1$H-NMR (hydrogen chloride salt, DMSO-d$_6$) δ 8.30 (d, 1H, J=2.1 Hz), 7.76 (t, 1H, J=1.7 Hz), 7.68–7.63 (m, 2H), 7.43 (t, 1H, J=7.9 Hz), 7.32 (m, 1H), 6.88 (d, 1H, J=8.7 Hz), 4.50 (bs, 3H), 3.07 (m, 1H), 0.98 (m, 4H); MS ((+)ESI) m/z 272/274 (M$^+$).

To a solution of (4-amino-3'-chloro-biphenyl-3-yl)-cyclopropyl-methanone (0.67 g, 2.5 mmol) in anhydrous THF (10 mL) at −78° C. was added a solution of methyl-magnesium bromide (3.0 M in diethyl ether, 2.5 mL, 7.5 mmol) under nitrogen. The reaction mixture was slowly warmed to rt, stirred under nitrogen for 12 hours, and quenched with a saturated aqueous ammonium chloride solution (40 mL). Ethyl acetate (50 mL) was added, organic layer was separated, and dried (MgSO$_4$). After removal of solvent, the residue was purified via silica gel column (hexane:ethyl acetate/7:1) to afford 1-(4-amino-3-chloro-biphenyl-3-yl)-1-cyclopropyl-ethanol as yellow oil: MS (EI) m/z 287/289 (M$^+$).

The title compound was prepared from 1-(4-amino-3'-chloro-biphenyl-3-yl)-1-cyclopropyl-ethanol and 1,1'carbonyldiimidazole according to Procedure C. Off-white solid: mp 158–159° C.; $^1$H-NMR (DMSO-d$_6$) δ 10.3 (s, 1H), 7.74 (t, 1H, J=1.71 Hz), 7.67–7.57 (m, 3H), 7.47 (t, 1H, J=7.88 Hz), 7.39 (d, 1H, J=8.1 Hz), 6.95 (d, 1H, J=8.12 Hz), 1.7 (s, 3H), 1.45 (m, 1H), 0.48 (m, 2H), 0.28 (m, 2H); MS (APCI) m/z 314 ([M+H]$^+$, 100%); Anal. Calc. For C$_{18}$H$_{16}$ClNO$_2$: C, 68.9; H, 5.14; N, 4.46. Found: C, 68.13; H, 5.01; N, 4.36.

EXAMPLE 42

6-(3-Chloro-phenyl)-4-cyclopropyl-4-propyn-1-yl-1,4-dihydro-benzo[d][1,3]oxazin-2-one 1-(4-Amino-3'-chloro-biphenyl-3-yl)-1-cyclopropyl-1-propynyl-methanol was prepared from (4-amino-3'-chloro-biphenyl-3-yl)-cyclopropyl-methanone and propynylmagnesium bromide according to Example 41.

A mixture of 1-(4-amino-3-chloro-biphenyl-3-yl)-1-cyclopropyl-1-propynyl-methanol (0.02 g, 0.064 mmol) and 1,1'-carbonyldiimidazole (0.016 g, 0.096 mmol) in dry THF (10 mL) was stirred under a blanket of nitrogen for 10 minutes. Upon completion of the reaction, the THF was removed and the residue purified via flash chromatography (silica gel, 40% ethyl acetate/hexane) to give 6-(3-chlorophenyl)-4-cyclopropyl-4-prop-1-ynyl-1,4-dihydro-benzo[d][1,3]oxazin-2-one (0.014 g, 56%) as a light yellow solid: mp 178–179° C.; $^1$H-NMR (DMSO-d$_6$) δ 10.6 (s, 1H), 7.68 (m, 2H), 7.64 (bs, 1H), 7.59 (d, 1H, J=7.72 Hz), 7.49 (t, 1H, J=7.82 Hz), 7.42 (d, 1H, J=7.95 Hz), 7.02 (d, 1H, J=8.0 Hz), 1.86 (s, 3H), 1.66 (m, 1H), 0.82 (m, 1H), 0.66 (m, 3H); MS (ESI) m/z 336 ([M–H]$^-$, 100%).

EXAMPLE 43

6-(3-Chloro-phenyl)-4,4-dicyclopropyl-1,4-dihydro-benzo[d][1,3]oxazin-2-one (4-Amino-3'-chloro-biphenyl-3-yl)-dicylopropyl-methanol (mp 90–92° C.; MS ((+)ESI) m/z 314 (M+H)$^+$.) was prepared from (4-amino-3'-chloro-biphenyl-3-yl)-cyclopropyl-methanone and cyclopropylmagnesium bromide according to Example 41.

The title compound was prepared according to Example 41 from (4-amino-3'-chloro-biphenyl-3-yl)-dicylopropyl-methanol and 1,1'-carbonyldiimidazole. Yellow solid: mp 198–200° C.; $^1$H-NMR (DMSO-d$_6$) δ 10.3 (s, 1H), 7.72 (bs, 1H), 7.67 (bs, 1H), 7.62 (m, 2H), 7.48 (t, 1H, J=7.88 Hz), 7.40 (d, 1H, J=8.04 Hz), 6.94 (d, 1H, J=8.27 Hz), 1.55 (m, 2H), 0.5 (m, 6H), 0.28 (m, 2H); MS (EI) m/z 339 (M$^+$, 40%); Anal. Calc. For C$_{20}$H$_{18}$ClNO$_2$: C, 70.69; H, 5.34 N, 4.12. Found: C, 69.38; H, 5.07; N, 4.02.

EXAMPLE 44

6-(3-Chloro-phenyl)-4,4-dipropyn-1-yl-1,4-dihydrobenzo[d][1,3]oxazin-2-one

Following the procedure of Example 41, (4-amino-3'-chloro-biphenyl-3-yl)-propynyl-methanone (mp 112–114° C.; MS ((+) ESI) m/z 270/272 (M+H)+) was treated with propynylmagnesium bromide to give (4-amino-3-chloro-biphenyl-3-yl)-dipropynyl-methanol which was reacted with 1,1'-carbonyldiimidazole to afford the title compound. Yellow solid: mp 151° C. (decomposed); $^1$H-NMR (DMSO-$d_6$) δ10.8 (s, 1H), 7.71 (dd, 1H, J=8.52, 1.94 Hz), 7.69 (m, 2H), 7.61 (d, 1H, J=7.64 Hz), 7.50 (t, 1H, J=7.85 Hz), 7.43 (d, 1H, J=7.99 Hz), 7.06 (d, 1H, J=8.23 Hz), 2.0 (s, 6H); MS (APCI) m/z 336 ([M+H]+, 20%).

EXAMPLE 45

6-(3-Bromo-5-fluorophenyl)-1,4,4-trimethyl-1,4-dihydrobenzo[d][1,3]oxazin-2-one To a solution of 6-(3-bromo-5-fluorophenyl)-4,4-dimethyl-1,4-dihydrobenzo[d][1,3]oxazin-2-one (0.34 g, 0.99 mmol) in dry DMF (10 mL) was added under nitrogen at room temperature sodium hydride (80 mg, 2.0 mmol) in one portion. The mixture was stirred at ambient temperature for 30 minutes, treated with iodomethane (1 mL, excess), and stirred for 2 hours. To the reaction mixture was added a cold saturated ammonium chloride solution (30 mL) and the white precipitate obtained was collected on a filter, washed with the distilled water to afford the title compound as a white solid (0.31 g, 87%): mp 157–158° C.; $^1$H-NMR (DMSO-$d_6$) δ7.83 (s, 1H), 7.76 (dd, 1H, J=8.5, 2.0 Hz), 7.67 (m, 2H), 7.53 (dt, 1H, J=8.3, 1.9 Hz), 7.18 (d, 1H, J=8.5 Hz), 3.33 (s, 3H), 1.67 (s, 6H); $^{19}$F-NMR (DMSO-$d_6$) δ–111.01 (m, 1F); MS (APCI) m/z 364 ([M+H]+, 96%), 366 ([M+H]+, 100%).

EXAMPLE 46

1-(2-Amino-5-chloro-phenyl)-2,2,2-tifluoro-ethanone

To a solution of N-(4-chlorophenyl)-2,2-dimethylpropanamide (6.7 g, 30 mmol) in anhydrous THF (100 mL) under nitrogen at 0° C. was added a solution of n-BuLi (2.5M, 30 mL, 70 mmol) in hexane in a dropwise fashion. After addition, the solution was kept stirring at 0° C. for 40 minutes and treated with a solution of 1-(trifluoroacetyl)imidazole (9 mL, 78 mmol) in anhydrous THF (10 mL). The reaction mixture was warmed to ambient temperature and kept for 18 hours. To the reaction solution was added a saturated aqueous ammonium chloride solution (50 mL) followed by addition of ethyl acetate (100 mL). The organic layer was separated and the solvent was removed in vacuo. The residue obtained was suspended in 3N aqueous hydrochloride solution (50 mL) and heated at reflux overnight. The reaction solution was cooled to room temperature and treated with a cold ammonium hydroxide solution to pH>8. The aqueous mixture was extracted with ethyl acetate (3×50 mL) and organic layers were washed with brine and dried (MgSO$_4$). After removal of solvent, the residue was purified by a flash chromatography (silica gel, hexane:ethylacetate/4:1) to afford the title compound as a yellow solid (1 g, 15%): mp 93–94° C.; $^1$H-NMR (CDCl$_3$) δ7.70 (m, 1H), 7.33 (dd, 1H, J=9.0, 2.3 Hz), 6.70 (d, 1H, J=9.1 Hz), 6.45 (bs, 2H); MS (ESI) m/z 222 (M–H, 100%), 224 (M–H, 33%).

EXAMPLE 47

6-Chloro-4-methyl-4-trifluoromethyl-1,4-dihydro-benzo[d][1,3]oxazin-2-one

Prepared from 1-(2-amino-5-chloro-phenyl)-2, 2,2-trifluoro-ethanone by addition of methylmagnesium bromide followed by treatment of the resultant carbinol with 1,1'-carbonyldiimidazole according to the procedure of Example 2. White solid: mp 216–216° C.; $^1$H-NMR (DMSO-$d_6$) δ10.91 (bs, 1H, D$_2$O exchangeable), 7.64 (d, 1H, J=1.6 Hz), 7.49 (dd, 1H, J=8.6, 2.3 Hz), 6.95 (d, 1H, J=8.6 Hz), 1.91 (s, 3H); $^{19}$F-NMR (DMSO-$d_6$) δ–82.0 (s, 1F); MS (EI) m/z 264 ([M–H]−, 100%), 266 ([M–H]−, 33%). Anal. Calc. For C$_{10}$H$_7$ClF$_3$NO$_2$: C, 45.22; H, 2.66; N, 5.27. Found: C, 45.32, H, 2.77; N, 4.83.

EXAMPLE 48

6-(3-Methoxyphenyl)-4-methyl-4-trifluoromethyl-1,4-dihydro-benzo[d][1,3]oxazin-2-one A mixture of 6-chloro-4-methyl-4-trifluoromethyl-1,4-dihydro-benzo[d][1,3]-oxazin-2-one (0.2 g, 0.75 mmol), 3-methoxyphenyl boronic acid (0.13 g, 0.9 mmol), potassium phosphate (0.23 g, 1.1 mmol), and nickel (II) (diphenylphosphino)ferrocenyl dichloride (52 mg, 0.076 mmol) in anhydrous dioxane was subject to a blanket of nitrogen to remove oxygen and heated at 95° C. under nitrogen for 48 hours. Another portion of 3-methoxyphenyl boronic acid (0.13 g, 0.9 mmol) and Nickel (II) (diphenylphosphino)ferrocenyl dichloride (52 mg, 0.076 mmol) was added and the reaction solution was heated at 95° C. under nitrogen for a further 48 hours. The reaction solution was cooled to room temperature. Saturated aqueous ammonium chloride solution (30 mL) and ethyl acetate (50 mL) was added. The organic layer was separated and the aqueous layer was extracted with ethyl acetate (3×20 mL). The combined organic layer was washed with brine and dried (MgSO$_4$). After removal of solvent, the residue was purified by a flash chromatography (silica gel, hexane:ethyl acetate/4:1) to afford the title compound as a white solid (50 mg, 20%): mp 178–179° C.; $^1$H-NMR (DMSO-$d_6$) δ10.85 (bs, 1H, D$_2$O exchangeable), 7.73 (m, 2H), 7.38 (t, 1H, J=7.9 Hz), 7.23 (d, 1H, J=7.7 Hz), 7.19 (d, 1H, J=1.9 Hz), 7.02 (d, 1H, J=8.2 Hz), 6.94 (dd, 1H, J=8.2, 2.4 Hz), 3.88 (s, 3H), 1.98 (s, 3H); $^{19}$F-NMR (DMSO-$d_6$) δ–81.88 (s, 1F); Anal. Calc. For C$_{17}$H$_{14}$F$_3$NO$_3$: C, 60.54; H, 4.18; N, 4.15. Found: C, 60.58; H, 4.44; N, 4.19.

EXAMPLE 49

7-(3-Methoxy-phenyl)-4,4-dimethyl-1,4-dihydro-benzo[d][1,3]-oxazin-2-one

A mixture of 7-chloro-4,4'-dimethylbenzoxazin-2-one (0.197 g, 0.93 mmol), 3-methoxyphenyl boronic acid (0.21 g, 1.4 mmol), Ni(dppf)Cl$_2$ (0.095 g, 0.14 mmol), and potassium phosphate (0.59 g, 2.79 mmol) in dioxane (10 mL) was subject to a blanket of nitrogen for 15 minutes at 50° C. and then was heated at 95° C. for 48 hours. The reaction mixture was cooled to room temperature and ethyl acetate (100 mL) was added. The organics were washed twice with aqueous ammonium chloride (30 mL), once with brine (30 mL), and dried over magnesium sulfate. The residue was purified via flash chromatography (silica gel, 40% ethyl acetate/hexane) to give 7-(3-methoxy-phenyl)-4,4-dimethyl-1,4-dihydro-benzo[d][1,3]oxazin-2-one (0.090 g, 35%) as a clear oil. The oil was triturated with ether (25 ml) to furnish a white solid:

mp 167–168° C.; $^1$H-NMR (DMSO-d$_6$) δ10.3 (s, 1H), 7.42–7.28 (m, 3H), 7.14 (d, 1H, J=8.11 Hz), 7.11 (bs, 2H), 6.96 (dd, 1H, J=8.11 Hz), 3.56 (s, 3H), 1.52 (s, 6H); MS (EI) m/z 283 ([M+H]$^+$, 90%); Anal. Calc. For C$_{17}$H$_{17}$NO$_3$: C, 72.07; H, 6.05; N, 4.94. Found: C, 71.59; H, 6.08; N, 4.79.

EXAMPLE 50

6-(3-Acetyl-phenyl)-4,4-dimethyl-1,4-dihydro-benzo[d][1,3]-oxazin-2-one 3-(4,4-Dimethyl-2-oxo-1,4-dihydro-2H-benzo[d][1,3]oxazin-6-yl)benzonitrile (0.25 g, 0.9 mmol) was dissolved in THF (10 mL) and cooled to 0° C. To this solution, methylmagnesium bromide (3.0 M in ether, 1.8 mL, 5.4 mmol) was added and the reaction mixture was heated to reflux under nitrogen. Upon completion of the reaction, the reaction mixture was quenched with 1 N aqueous HCl solution after cooling to rt. The mixture was extracted with ethyl acetate (100 mL), dried over MgSO$_4$ and concentrated. Purification of the residue obtained via chromatography (silica gel, 50% ethyl acetate/hexane) gave 6-(3-acetyl-phenyl)-4,4-dimethyl-1,4-dihydro-benzo[d][1,3]oxazin-2-one as a white solid (0.031 g, 12%): mp 178–179° C.; $^1$H-NMR (CDCl$_3$) δ8.15 (t, 1H, J=1.71 Hz), 8.04 (s, 1H), 7.95 (dt, 1H, J=8.85, 1.13 Hz), 7.76 (dt, 1H, J=7.90, 1.43 Hz), 7.57 (t, 1H, J=7.72 Hz), 7.52 (dd, 1H, J=8.28, 2.11 Hz), 7.39 (d, 1H, J=1.81 Hz), 6.93 (d, 1H, J=8.19 Hz), 2.69 (s, 3H), 1.81 (s, 6H); MS (EI) m/z 295 ([M+H]$^+$, 40%)

EXAMPLE 51

6-(3-Benzoyl-phenyl)-4,4-dimethyl-1,4-dihydro-benzo[d][1,3]-oxazin-2-one

Prepared from 3-(4,4-dimethyl-2-oxo-1,4-dihydro-2H-benzo[d][1,3]oxazin-6-yl)benzonitrile and phenylmagnesium bromide according to the procedure of Example 50. A white solid: mp 156–157° C.; $^1$H-NMR (DMSO-d$_6$) δ10.33 (s, 1H), 8.0–7.96 (m, 2H), 7.80 (m, 2H), 7.73–7.56 (m, 7H), 6.99 (d, 1H, J=8.06 Hz), 1.67 (s, 6H); MS (EI) m/z 357 ([M+H]$^+$, 40%); Anal. Calc. For C$_{23}$H$_{19}$NO$_3$: C, 77.29; H, 5.36; N, 3.92 Found: C, 75.7; H, 5.28; N, 3.86

EXAMPLE 52

4,4-Dimethyl-6-[3-(1H-tetrazol-5-yl)-phenyl]-1,4-dihydrobenzo[d][1,3]oxazin-2-one A mixture of 3-(4,4-dimethyl-2-oxo-1,4-dihydro-2H-benzo [d][1,3]oxazin-6-yl)benzonitrile (0.77 g, 2.8 mmol), trimethylsilyl azide (0.68 g, 5.6 mmol), and dibutyl tin oxide (0.071 g, 0.28 mmol) in dioxane (20 mL) was heated at reflux under a blanket of nitrogen. Upon completion of the reaction, the dioxane was removed, the organics taken up in ethyl acetate (100 mL), and washed with NaHCO$_3$ (100 mL). The aqueous layer was acidified with 1 N aqueous HCl and extracted with ethyl acetate (100 mL). The organic layer was dried over MgSO$_4$, and concentrated. Crystallization from ether (20 mL) gave 4,4-dimethyl-6-[3-(1H-tetrazol-5-yl)-phenyl]-1,4-dihydrobenzo[d][1,3]-oxazin-2-one as a light yellow solid (0.23 g, 26%): mp 238–240° C.; $^1$H-NMR (DMSO-d$_6$) δ10.4 (s, 1H), 8.3 (bs, 1H), 8.02 (d, 1H, J=7.66 Hz), 7.9 (d, 1H, J=7.91 Hz), 7.72–7.65 (m, 3H), 7.03 (d, 1H, J=8.75 Hz), 1.70 (s, 6H); MS (ESI) m/z 320 ([M–H]$^-$, 100%); Anal. Calc. For C$_{17}$H$_{15}$N$_5$O$_2$: C, 63.54; H, 4.71; N, 21.79. Found: C, 62.16; H, 4.67; N, 21.31.

EXAMPLE 53

4-(4,4-Dicyclopropyl-2-oxo-1,4-dihydro-2H-benzo[d][1,3]oxazin-6-yl)-thiophene-2-carbonitrile (4,4-Dicyclopropyl-1,4-dihydro-2-oxo-2H-3,1-benzoxazin-6-yl)boronic acid was prepared from 2-amino-5-bromobenzoic acid according to Example 1, 2, and 4. A white solid: mp 240–242° C.; $^1$H-NMR (DMSO-d$_6$) δ10.13 (s, 1H), 8.01 (s, 2H), 7.85 (s, 1H), 7.64 (d, 1H, J=7.9 Hz), 6.77 (d, 1H, J=7.9 Hz), 1.38 (m, 2H), 0.52 (m, 2H), 0.39 (m, 4H), 0.22 (m, 2H).

The title compound was prepared according to Procedure B from (4,4-dicyclopropyl-1,4-dihydro-2-oxo-2H-3,1-benzoxazin-6-yl)boronic acid and 4-bromo-2-thiophene carbonitrile. A white solid: mp 244–245° C.; $^1$H-NMR (DMSO-d$_6$) δ10.25 (s, 1H), 8.49 (d, 1H, J=0.87 Hz), 8.33 (s, 1H), 7.74 (d, 1H, J=1.44 Hz), 7.67 (dd, 1H, J=8.28, 1.54 Hz), 6.90 (d, 1H, J=8.28 Hz), 1.53 (m, 2H), 0.59–0.41 (m, 6H), 0.31–0.24 (m, 2H); MS (ESI) m/z 335 ([M–H]$^-$, 100%); Anal. Calc. For C$_{19}$H$_{16}$N$_2$O$_2$S: C, 67.84; H, 4.79; N, 8.33. Found: C, 64.92; H, 4.66; N, 7.71.

EXAMPLE 54

6-(3-Bromo-5-fluoro-phenyl)-4,4-dicyclopropyl-1,4-dihydrobenzo-[d][1,3]oxazin-2-one Prepared according to Procedure B from (4,4-dicyclopropyl-1,4-dihydro-2-oxo-2H-3,1-benzoxazin-6-yl)boronic acid and 1,3-dibromo-5-fluorobenzene. A white solid: mp 228–229° C.; $^1$H-NMR (DMSO-d$_6$) δ10.3 (s, 1H), 7.76–7.72 (m, 2H), 7.65 (dd, 1H, J=8.32, 1.74 Hz), 7.60 (d, 1H, J=10.36 Hz), 7.51 (d, 1H, J=8.3 Hz), 6.93 (d, 1H, J=8.31 Hz), 1.63–1.54 (m, 2H), 0.58–0.41 (m, 6H), 0.30–0.28 (m, 2H); MS (APCI) m/z 402/404 ([M–H]$^-$, 100%); Anal. Calc. For C$_{20}$H$_{17}$BrFNO$_2$: C, 58.48; H, 4.17; N, 3.41. Found: C, 58.77; H, 4.23; N, 3.32.

EXAMPLE 55

3-(4,4-Dicyclopropyl-2-oxo-1,4-dihydro-2H-benzo[d][1,3]oxazin-6-yl)-5-fluoro-benzonitrile A mixture of 6-(3-bromo-5-fluoro-phenyl)-4,4-dicyclopropyl-1,4-dihydro-benzo-[d][1,3]oxazin-2-one (0.4 g, 1.0 mmol), Zn(CN)$_2$ (0.71 g, 0.61 mmol), and tetrakis (triphenylphosphine)-palladium (0) (0.07 g, 0.06 mmol) in DMF (20 mL) was subject to a blanket of nitrogen for 15 minutes at 50° C. and then was heated at 85° C. for 1 hour. After cooling to room temperature, the reaction mixture was poured into NH$_4$Cl (100 mL) and extracted with ethyl acetate (3×50 mL). The organic layers were washed with brine, dried over MgSO$_4$, and concentrated. The clear oil obtained was triturated with ether (30 ml) to give a white solid. Recrystallization of the solid from ethyl acetate gave 3-(4,4-dicyclopropyl-2-oxo-1,4-dihydro-2H-benzo[d][1,3]oxazin-6-yl)-5-fluoro-benzonitrile (0.016 g, 4.6%): mp 250–252° C.; $^1$H-NMR (DMSO-d$_6$) δ10.3 (s, 1H), 8.12 (s, 1H), 7.97 (d, 1H, J=10.54 Hz), 7.81–7.79 (m, 2H), 7.73 (dd, 1H, J=8.3, 1.59 Hz), 6.94 (d, 1H, J=8.34 Hz), 1.59 (m, 2H), 0.58–0.42 (m, 6H), 0.30–0.28 (m, 2H); MS (ESI) m/z 347 ([M–H]$^-$, 100%); Anal. Calc. For C$_{21}$H$_{17}$FN$_2$O$_2$: C, 72.4; H, 4.92; N, 8.04 Found: C, 72.4; H, 4.74; N, 7.61

EXAMPLE 56

6-(3-Bromo-5-methyl-phenyl)-4,4-dimethyl-1,4-dihydrobenzo-[d][1,3]oxazin-2-one Prepared from (4,4-dimethyl-1,4-dihydro-2-oxo-2H-3,1-benzoxazin-6-yl)boronic acid and 3,5-dibromotoluene according to Procedure B. White solid: mp 231–233° C.; $^1$H-NMR (DMSO-d$_6$) δ10.4 (s, 1H), 7.66 (s, 1H), 7.58–7.56 (m, 2H), 7.50 (s, 1H), 7.37 (s, 1H), 6.95 (d, 1H, J=8.67 Hz), 2.37 (s, 3H), 1.67 (s, 6H); MS (ESI) m/z 344/346 ([M−H]$^−$, 100%); Anal. Calc. For C$_{17}$H$_{16}$BrNO$_2$: C, 58.98; H, 4.66; N, 4.05. Found: C, 58.82; H, 4.62; N, 3.94.

EXAMPLE 57

6-(3-Bromo-5-trifluoromethoxy-phenyl)-4,4-dimethyl-1,4-dihydrobenzo[d][1,3]-oxazin-2-one Prepared from (4,4-dimethyl-1,4-dihydro-2-oxo-2H-3,1-benzoxazin-6-yl)boronic acid and 1,3-dibromo-5-trifluoromethoxybenzene according to Procedure B. White solid: mp 214–216° C.; 1H-NMR (DMSO-d$_6$) δ10.4 (s, 1H), 7.99 (s, 1H), 7.73 (s, 1H), 7.68–7.62 (m, 3H), 6.97 (d, 1H, J=8.0 Hz), 1.68 (s, 6H); MS (ESI) m/z 414 ([M−H]$^−$, 100%); Anal. Calc. For C$_{17}$H$_{13}$BrF$_3$NO$_3$: C, 49.06; H, 3.15; N, 3.37. Found: C, 49.16; H, 3.05; N, 3.30.

EXAMPLE 58

3-(4,4-Dimethyl-2-oxo-1,4-dihydro-2H-benzo[d][1,3]oxazin-6-yl)-5-methyl-benzonitrile Prepared from 6-(3-bromo-5-methyl-phenyl)-4,4-dimethyl-1,4-dihydrobenzo-[d][1,3]oxazin-2-one according to the procedure of example 55. White solid: mp 256–258° C.; $^1$H-NMR (DMSO-d$_6$) δ10.4 (s, 1H), 7.99 (s, 1H), 7.86 (s, 1H), 7.67–7.62 (m, 3H), 6.97 (d, 1H, J=8.11 Hz), 2.42 (s, 3H), 1.68 (s, 6H); MS (APCI) m/z 293 ([M+H]$^+$, 100%); Anal. Calc. For C$_{18}$H$_{16}$N$_2$O$_2$: C, 73.96; H, 5.52; N, 9.58. Found: C, 73.26; H, 5.46; N, 9.24.

EXAMPLE 59

3-(4,4-Dimethyl-2-oxo-1,4-dihydro-2H-benzo[d][1,3]oxazin-6-yl)-5-trifluoromethoxy-benzonitrile Prepared from 6-(3-bromo-5-trifluoromethoxy-phenyl)-4,4-dimethyl-1,4-dihydrobenzo[d][1,3]oxazin-2-one according to the procedure of example 55. White solid: mp 227–228° C.; $^1$H-NMR (DMSO-d$_6$) δ10.4 (s, 1H), 8.32 (s, 1H), 8.09 (s, 1H), 7.97 (s, 1H), 7.75–7.72 (m, 3H), 6.99(d, 1H, J=8.11 Hz), 1.7 (s, 6H); MS (APCI) m/z 363 ([M+H]$^+$, 80%); Anal. Calc. For C$_{18}$H$_{13}$F$_3$N$_2$O$_3$: C, 59.67; H, 3.62; N, 7.73. Found: C, 59.63; H, 3.55; N, 7.58.

EXAMPLE 60

6-(3,5-difluoro-phenyl)-4,4-dimethyl-1,4-dihydrobenzo-[d][1,3]oxazin-2-one

Prepared according to procedure B from (4,4-dimethyl-1,4-dihydro-2-oxo-2H-3,1-benzoxazin-6-yl)boronic acid and 1-bromo-3,5-difluorobenzene. A white solid: mp 218–219° C.; $^1$H-NMR (DMSO-d$_6$) δ10.4 (s, 1H), 7.67–7.65 (m, 2H), 7.49 (d, 2H, J=7.73 Hz), 7.19 (t, 1H, J=9.29 Hz), 6.96 (d, 1H, J=8.88 Hz), 1.7 (s, 6H); MS (APCI) m/z 290 ([M+H]$^+$, 100%); Anal. Calc. For C$_{16}$H$_{13}$F$_2$NO$_2$: C, 66.43; H, 4.53, N, 4.84. Found: C, 66.01; H, 4.46; N, 4.67.

EXAMPLE 61

6-(3,5-dichloro-phenyl)-4,4-dimethyl-1,4-dihydrobenzo-[d][1,3]oxazin-2-one

Prepared from 6-bromo-4,4-dimethyl-1,4-dihydro-benzo[d][1,3]oxazin-2-one and 3,5-dichlorophenyl boronic acid according to Procedure A. A white solid: mp 245–246° C.; $^1$H-NMR (DMSO-d$_6$) δ10.4 (s, 1H), 7.77 (m, 2H), 7.67–7.64 (m, 2H), 7.56 (bs, 1H), 6.96 (d, 1H, J=7.98 Hz), 1.7 (s, 6H); MS (EI) m/z 321 ([M+H]$^+$, 40%); Anal. Calc. For C$_{16}$H$_{13}$Cl$_2$NO$_2$: C, 59.32; H, 4.11; N, 4.32. Found: C, 59.13; H, 4.29; N, 4.17.

EXAMPLE 62

6-(3,5-Bis-trifluoromethyl-phenyl)-4,4-dimethyl-1,4-dihydro-benzo[d][1,3]oxazin-2-one Prepared from 6-bromo-4,4-dimethyl-1,4-dihydro-benzo[d][1,3]oxazin-2-one and bis-trifluoromethylphenyl boronic acid according to Procedure A. A white solid: mp 258–260° C.; 1H-NMR (DMSO-d$_6$) δ10.4 (s, 1H), 8.35 (s, 2H), 8.05 (s, 1H), 7.79–7.76 (m, 2H), 7.01 (d, 1H, J=8.01 Hz), 1.7 (s, 6H); MS (ESI) m/z 390 ([M+H]$^+$, 20%); Anal. Calc. For C$_{18}$H$_{13}$F$_6$NO$_2$: C, 55.54; H, 3.37; N, 3.6. Found: C, 55.5; H, 3.54; N, 3.47.

EXAMPLE 63

3-(4,4-Dimethyl-2-oxo-1,4-dihydro-2H-benzo[d][1,3]oxazin-6-yl)-5-methoxy-benzonitrile A mixture of (4,4-dimethyl-1,4-dihydro-2-oxo-2H-3,1-benzoxazin-6-yl)boronic acid (4.2 g, 19.0 mmol), 3-cyano-5-methoxyphenyltriflate (5.1 g, 19.0 mmol), tetrakis (triphenylphosphine)-palladium (0) (1.1 g, 0.95 mmol), sodium carbonate (4.0 g, 38.0 mmol), and lithium bromide (5 g, 57 mmol) in DME (50 mL) and water (25 mL) was subject to a blanket of nitrogen for 15 minutes at 50° C. and then was heated at 85° C. for 1 hour. The reaction was cooled to room temperature and ethyl acetate (100 mL) was added. The organic layers were washed twice with aqueous ammonium chloride (100 mL) and once with brine (100 mL), dried over magnesium sulfate and concentrated. Purification via chromatography (silica gel, 40% ethyl acetate/hexane) gave 3-(4,4-dimethyl-2-oxo-1,4-dihydro-2H-benzo[d][1,3] oxazin-6-yl)-5-methoxy-benzonitrile as a white solid (0.69 g, 53%): mp 254–255° C.; $^1$H-NMR (DMSO-d$_6$) δ10.4 (s, 1H), 7.84 (s, 1H), 7.67–7.61 (m, 2H), 7.55 (bs, 1H), 7.4 (bs 1H) 6.99 (d, 1H, J=7.94 Hz), 3.88 (s, 3H), 1.67 (s, 6H); MS (EI) m/z 308 ([M+H]$^+$, 30%); Anal. Calc. For C$_{18}$H$_{16}$N$_2$O$_3$: C, 68.13; H, 5.40; N, 8.83. Found: C, 68.03; H, 5.22; N, 8.46.

EXAMPLE 64

6-(3-Fluoro-phenyl)-4,4-dimethyl-1,4-dihydro-benzo[d][1,3]-oxazin-2-one

Prepared from 6-bromo-4,4-dimethyl-1,4-dihydro-benzo[d][1,3]oxazin-2-one 1-bromo-3-fluorobenzene according to Procedure A. A light yellow solid: mp 181–182° C.; $^1$H-NMR (DMSO-d$_6$) δ10.4 (s, 1H), 7.62–7.44 (m, 5H), 7.16 (t, 1H, J=2.22 Hz), 6.97 (d, 1H, J=8.83), 1.67 (s, 6H); MS (EI) m/z 271 ([M+H]$^+$, 40%); Anal. Calc. For C$_{16}$H$_{14}$FNO$_2$: C, 69.91; H, 5.3; N, 5.1. Found: C, 70.0; H, 5.32; N, 4.92.

EXAMPLE 65

6-(3-Chloro-4-fluoro-phenyl)-4,4-dimethyl-1,4-dihydro-benzo[d][1,3]oxazin-2-one Prepared from 6-bromo-4,4-dimethyl-1,4-dihydro-benzo[d][1,3]oxazin-2-one and 1-bromo-3-chloro-4-fluorobenzene according to Procedure A. White solid: mp 211–212° C.; $^1$H-NMR (DMSO-$d_6$) δ10.4 (s, 1H), 7.92 (dd, 1H, J=7.13, 2.19 Hz), 7.71–7.66 (m, 1H), 7.60–7.57 (m, 2H), 7.49 (t, 1H, J=8.95 Hz), 6.96 (d, 1H, J=8.01 Hz), 1.67 (s, 6H); MS (EI) m/z 305 ([M+H]$^+$, 20%); Anal. Calc. For $C_{16}H_{13}ClFNO_2$: C, 62.86; H, 4.29; N, 4.58. Found: C, 62.52; H, 4.45; N, 4.42.

EXAMPLE 66

3-(1-Diethoxymethyl-4,4-dimethyl-2-oxo-1,4-dihydro-2H-benzo[d][1,3]oxazin-6-yl)-5fluoro-benzonitrile A mixture of 3-(4,4-Dimethyl-2-oxo-1,4-dihydro-2H-benzo[d][1,3]oxazin-6yl)-5-fluoro-benzonitrile (0.25 g, 0.84 mmol) and triethylorthoformate (50 mL) was heated at 160° C. for 12 hours. The excess triethylorthoformate was removed in vacuo and purification via chromatography (silica gel, 20% ethyl acetate/hexane) gave 3-(1-diethoxymethyl-4,4-dimethyl-2-oxo-1,4-dihydro-2H-benzo[d][1,3]oxazin-6-yl)-5-fluoro-benzonitrile (0.116 g, 33%) as a white solid: mp 123–124° C.; $^1$H-NMR (DMSO-$d_6$) δ7.97 (d, 1H, J=8.68 Hz), 7.66 (bs, 1H), 7.53–7.44 (m, 2H), 7.35–7.32 (m, 2H), 6.65 (s, 1H), 3.88–3.78 (m, 2H), 3.73–3.61 (m, 2H), 1.77 (s, 6H), 1.27 (t, 6H, J=7.05 Hz); MS (ESI) m/z 295 ([M–H]$^+$, 100%, lower MW ion consistent with loss of diethyl acetal); Anal. Calc. For $C_{22}H_{23}FN_2O_4$: C, 66.32; H, 5.82; N, 7.03. Found: C, 65.89; H, 5.92; N, 6.66.

EXAMPLE 67

3-Fluoro-5-(1-methoxymethyl-4,4-dimethyl-2-oxo-1,4-dihydro-2H-benzol[d][1,3]oxazin-6-yl)-benzonitrile A solution of 3-(4,4-dimethyl-2-oxo-1,4-dihydro-2H-benzo [d][1,3]oxazin-6-yl)-5-fluorobenzonitrile (0.150 g, 0.51 mmol) in DMF (5 mL) was treated at rt with sodium hydride (0.061 g, 1.53 mmol). The mixture was stirred for 30 minutes and treated with chloromethyl methylether (0.062 g, 7.7 mmol). Upon completion of the reaction, the reaction mixture was quenched with water (25 mL) and extracted with ethyl acetate (3×30 mL), dried over MgSO$_4$, and concentrated. The residue was purified via chromatography (silica gel, 25% ethyl acetate/hexane) to give 3-fluoro-5-(1-methoxymethyl-4,4-dimethyl-2-oxo-1,4-dihydro-2H-benzo [d][1,3]oxazin-6-yl)-benzonitrile as a white solid (0.11 g, 65%): mp 169–171° C.; $^1$H-NMR (DMSO-$d_6$) δ8.17 (bs, 1H), 8.03 (dt, 1H, J=10.4, 2.13 Hz), 7.85–7.77 (m, 3H), 7.31 (d, 1H, J=8.49 Hz), 5.33 (s, 2H), 3.35 (s, 3H), 1.7 (s, 6H); MS (APCI) m/z 341 ([M+H]$^+$, 50%); Anal. Calc. For $C_{19}H_{17}FN_2O_3$: C, 65.32; H, 5.19; N, 8.02. Found: C, 64.92; H, 4.96; N, 7.73.

EXAMPLE 68

Phosphoric acid 6-(3-cyano-5fluoro-phenyl)-4,4-dimethyl-4H-benzo[d][1.3]oxazin-2-yl ester diethyl ether To a solution of 3-(4,4-dimethyl-2-oxo-1,4-dihydro-2H-benzo[d][1,3]oxazin-6-yl)-5-fluorobenzonitrile (0.25 g, 0.84 mmol) in DMF (5 mL) was added sodium hydride (60% in oil, 0.101 g, 2.53 mmol). After stirring for 30 minutes, the reaction mixture was treated with diethyl chlorophosphate (0.22 mL, 1.52 mmol). Upon completion of the reaction, the reaction solution was quenched with water (25 mL) and the product extracted with ethyl acetate (2×50 mL), dried over MgSO$_4$, and concentrated. The residue was purified via chromatography (silica gel, 25% ethyl acetate/hexane) to give phosphoric acid 6-(3-cyano-5-fluoro-phenyl)-4,4-dimethyl-4H-benzo[d][1,3]oxazin-2-yl ester diethyl ether as a white solid (0.064 g, 18%): mp 196–198° C.; $^1$H-NMR (DMSO-$d_6$) δ8.19 (bs, 1H), 8.05 (d, 1H, J=10.4 Hz), 7.9–7.8 (m, 3H), 7.51 (d, 1H, J=8.41 Hz), 4.33–4.41 (m, 4H), 1.76 (s, 6H), 1.27 (t, 6H, J=7.05 Hz); MS (APCI) m/z 433 ([M+H]$^+$, 80%); Anal. Calc. For $C_{21}H_{22}FN_2O_5P$: C, 58.33; H, 5.13; N, 6.48. Found: C, 58.1; H, 5.11; N, 6.25.

EXAMPLE 69

3-(4,4-Dimethyl-2-oxo-1,4-dihydro-2H-benzo[d][1,3]oxazin-6-yl)-4-fluoro-benzonitrile Prepared from (1,4-dihydro-4,4-dimethyl-2-oxo-2H-3,1-benzoxin-6-yl)boronic acid and 5-bromo-2-fluorobenzonitrile according to Procedure B. white solid: mp 229–230° C.; $^1$H-NMR (DMSO-$d_6$) δ10.4 (s, 1H), 8.15 (dd, 1H, J=7.39, 2.12 Hz), 7.95–7.89 (m, 1H), 7.59–7.48 (m, 3H), 6.99 (d, 1H, J=8.1 Hz), 1.7 (s, 6H); MS (APCI) m/z 297 ([M+H]$^+$, 100%); Anal. Calc. For $C_{17}H_{13}FN_2O_2$: C, 68.91; H, 4.42; N, 9.45. Found: C, 68.74; H, 4.83; N, 9.10.

EXAMPLE 70

8-Fluoro-4,4-dimethyldihydro-benzo[d][1,3]oxazin-2-one

N-(tert-Butoxycarbonylamino)-3-fluorobenzoic acid (Takagishi et al. Synlett 4, 360–2 (1992); mp 159–161° C.) was deprotected using trifluoroacetic acid to give o-amino benzoic acid which was treated with methylmagnesium bromide to afford o-amino dimethyl carbinol. The o-amino dimethyl carbinol (2.23 g, 13.2 mmol) was treated with 1,1-carbonyldiimidizole (2.8 g, 17.2 mmol) in THF (20 mL) at 50° C. for 12 hours. Upon completion of reaction, it was cooled to rt and ethyl acetate (100 mL) added. The organic layer was washed with 10% aqueous HCl solution (2×25 mL), dried over MgSO$_4$ and concentrated. The residue was purified via chromatography (silica gel, 10% ethyl acetate/hexane) to give 8-fluoro-4,4-dimethyl-dihydro-benzo[d][1,3]oxazin-2-one as a white solid (1.3 g, 50%): mp 127–128° C.; $^1$H-NMR (DMSO-$d_6$) δ10.4 (s, 1H), 7.22–7.12 (m, 2H), 7.07–7.00 (m, 2H), 1.6 (s, 6H); MS (APCI) m/z 196 ([M+H]$^+$, 100%); Anal. Calc. For $C_{10}H_{10}FNO_2$: C, 61.53; H, 5.16; N, 7.18. Found: C, 61.27; H, 5.37; N, 7.02.

EXAMPLE 71

6-(3-Chloro-4-fluoro-phenyl)-8-fluoro-4,4-dimethyl-1,4-dihydrobenzo[d][1,3]-oxazin-2-one To a solution of 8-fluoro-4,4-dimethyl-dihydro-benzo[d][1,3]oxazin-2-one (0.15 g, 0.77 mmol) in acetic acid (5 mL) was added dropwise a solution of bromine (0.37 g, 2.31 mmol) in acetic acid (5 mL) under nitrogen at rt. After stirring for 10 minutes, the mixture was concentrated and the residue obtained was purified by a silica gel column (hexane:ethyl acetate/4:1) to afford 6-bromo-8-fluoro-4,4-dimethyl-dihydro-benzo[d][1,3]oxazin-2-one as an off-white solid (0.176 g, 84%) which was used in next step without further purification.

A mixture of 6-bromo-8-fluoro-4,4-dimethyl-dihydro-benzo[d][1,3]oxazin-2-one (0.176 g, 0.64 mmol), 4-fluoro-3-chlorophenyl boronic acid (0.15 g, 0.84 mmol), tetrakis(triphenylphosphine)-palladium (0) (0.04 g, 0.032 mmol), and sodium carbonate (0.20 g, 1.92 mmol) in DME (10 mL) and water (5 mL) was subject to a blanket of nitrogen for 15 minutes at 50° C. and then was heated at 85° C. for 1 hour. The reaction mixture was cooled to room temperature and ethyl acetate (100 mL) was added. The organic layer was washed twice with aqueous ammonium chloride (100 mL) and once with brine (100 mL), dried over magnesium sulfate and concentrated. The residue was purified via chromatography (silica gel, 25% ethyl acetate/hexane) to give 6-(3-chloro-4-fluoro-phenyl)-8-fluoro-4,4-dimethyl-1,4-dihydrobenzo[d][1,3]-oxazin-2-one as a white solid (0.13 g, 66%): mp 246–248° C.; $^1$H-NMR (DMSO-d$_6$) δ10.5 (s, 1H), 8.00 (dd, 1H, J=7.09, 2.32 Hz), 7.78–7.73 (m, 1H), 7.62 (dd, 1H, J=11.86, 1.77 Hz), 7.7 (t, 2H, J=9 Hz), 1.7 (s, 6H); MS (APCI) m/z 324 ([M+H]$^+$, 100%); Anal. Calc. For C$_{16}$H$_{12}$F$_2$NO$_2$ 0.5 H$_2$O C, 57.76; H, 3.94; N, 4.21. Found: C, 57.49; H, 3.69; N, 4.03.

EXAMPLE 72

6-(3-Bromo-phenyl)-4,4-dimethyl-1,4-dihydro-benzo[d][1,3]-oxazin-2-one

Prepared from (1,4-dihydro-4,4-dimethyl-2-oxo-2H-3,1-benzoxin-6-yl)boronic acid and 1,3-dibromobenzene according to procedure B. A white solid: mp 174–175° C.; $^1$H-NMR (DMSO-d$_6$) δ10.35 (s, 1H), 7.88 (bs, 1H), 7.68 (d, 1H, J=7.5 Hz), 7.6–7.51 (m, 3H), 7.4 (t, 1H, J=7.5 Hz), 6.97 (d, 1H, J=8.57 Hz), 1.64 (s, 6H); MS (EI) m/z 331([M$^+$], 60%), 333([M$^+$], 60%); Anal. Calc. For C$_{16}$H$_{14}$BrNO$_2$: C, 57.85; H, 4.25; N, 4.22. Found: C, 57.7; H, 4.36; N, 4.09.

EXAMPLE 73

4,4-Dimethyl-6-(3-trimethylsilanylethynyl-phenyl)-1,4-dihydro-benzo[d][1,3]oxazin-2-one A mixture of 6-(3-bromo-phenyl)-4,4-dimethyl-1,4-dihydro-benzo[d][1,3]oxazin-2-one (0.8 g, 2.4 mmol), trimethylsilylacetylene (1 g, 10 mmol), tetrakis(triphenylphosphine) palladium (0) (0.17 g, 0.24 mmol), and cuprous (I) iodide (0.05 g, 0.28 mmol) in triethyl amine (20 mL) was heated under nitrogen at 80° C. for 3 hours. The reaction mixture was cooled to rt and the solvent was removed. The residue was taken up in ethyl acetate (50 mL) and washed with 1N aqueous HCl (3×20 mL) and brine (20 mL). The organic layer was separated and dried (MgSO$_4$). After removal of solvent, the residue was purified by a silica gel chromatography (hexane:ethyl acetate/3:1) to afford the title compound as a white solid (0.77 g, 92%): mp 240–242° C.; $^1$H-NMR (DMSO-d$_6$) δ10.3 (s, 1H), 7.74–7.69 (m, 2H), 7.61–7.58 (m, 2H), 7.48–7.40 (m, 2H), 6.96 (d, 1H, J=7.98 Hz), 1.67 (s, 6H), 0.25 (s, 9H); MS (EI) m/z 349([M$^+$], 50%); Anal. Calc. For C$_{21}$H$_{23}$NO$_2$Si 0.2 EtOAc: C, 71.32; H, 6.75; N, 3.82. Found: C, 71.08; H, 6.64; N, 3.82.

EXAMPLE 74

6-(3-Ethynyl-phenyl)-4,4-dimethyl-1,4-dihydro-benzo[d][1,3]-oxazin-2-one

A mixture of 4,4-dimethyl-6-(3-trimethylsilanylethynyl-phenyl)-1,4-dihydro-benzo[d][1,3]oxazin-2-one (0.7 g, 2 mmol) and potassium carbonate (2 g, excess) in anhydrous methanol was stirred at rt under nitrogen for 4 hours. The mixture was treated with ice-water (100 mL) and extracted with ethyl acetate (2×80 mL). The organic layers were washed with brine and dried with MgSO$_4$. The solvent was removed and the title compound was obtained as a off-white solid (0.4 g, 72%): mp 171–172° C.; $^1$H-NMR (DMSO-d$_6$) δ10.3, (s, 1H), 7.78 (bs, 1H), 7.72–7.69 (m, 1H), 7.6–7.57 (m, 2H), 7.49–7.43 (m, 2H), 6.97 (d, 1H, J=7.98 Hz), 4.25 (s, 1H), 1.67 (s, 6H); MS (EI) m/z 277([M$^+$], 100%); Anal. Calc. For C$_{18}$H$_{15}$NO$_2$.0.2 EtOAc: C, 76.56; H, 5.67; N, 4.75. Found: C, 76.34; H, 5.4; N, 4.7.

EXAMPLE 75

3-[3-(4,4-Dimethyl-2-oxo-1,4-dihydro-2H-benzo[d][1,3]oxazin-6-yl)-phenyl]-propynenitrile To a stirred mixture of DMSO, acetonitrile and water (9 mL/3 mL/0.5 mL) was added at rt under nitrogen cuprous cyanide (0.193 g, 2.2 mmol), sodium iodide (11 mg, 0.072 mmol), and 6-(3-ethynyl-phenyl)-4,4-dimethyl-1,4-dihydro-benzo[d][1,3]oxazin-2-one (0.2 g, 0.72 mmol). Chlorotrimethylsilane was then added to the above mixture in a dropwise manner. After addition, the mixture was heated at 50° C. for 72 hours. The reaction mixture was then cooled to rt and treated with 0.5 N aqueous HCl cold solution (50 mL). The precipitate obtained was collected on a filter and washed with water. The solid was purified on a silica gel column (hexane:ethyl acetate/2:1) to give the title compound as an off-white solid (10 mg, 4.6%): mp 212–213° C.; $^1$H-NMR (CHCl$_3$-d$_6$) δ7.96 (s, 1H), 7.77 (s, 1H), 7.65 (d, 1H, J=7.8 Hz), 7.60 (d, 1H, J=7.69 Hz), 7.51 (d, 1H, J=7.77 Hz), 7.45 (dd, 1H, J=8.67, 2.21 Hz), 7.31 (d, 1H, J=1.55 Hz), 6.91 (d, 1H, J=8.19 Hz), 1.8 (s, 6H); MS (EI) m/z 302 ([M$^+$], 30%).

EXAMPLE 76

6-(3-Fluoro-5-nitro-phenyl)-4,4-dimethyl-1,4-dihydro-benzo[d][1,3]oxazin-2-one Prepared from (1,4-dihydro-4,4-dimethyl-2-oxo-2H-3,1-benzoxin-6-yl)boronic acid and 1-bromo-3-fluoro-5-nitrobenzene according to procedure B. A yellow solid: mp 260–261° C.; $^1$H-NMR (DMSO-d$_6$) δ10.4 (s, 1H), 8.37 (bs, 1H), 8.14–8.05 (m, 2H), 7.77–7.74 (m, 2H), 7.01 (d, 1H, J=7.94 Hz), 1.7 (s, 6H); MS (ESI) m/z 315([M–H]$^+$, 100%); Anal. Calc. For C$_{16}$H$_{13}$FN$_2$O$_4$: C, 60.76; H, 4.14; N, 8.86. Found: C, 60.34; H, 4.2; N, 8.61.

EXAMPLE 77

6-(3-Chloro-5-fluoro-phenyl)-4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 1-bromo-3-chloro-5-fluorobenzene according to procedure B. A white solid: mp 193–194° C.; $^1$H-NMR (DMSO-d$_6$) δ10.4 (s, 1H), 7.67–7.64 (m, 3H), 7.61–7.57 (m, 1H), 7.41–7.37 (m, 1H), 6.96 (d, 1H, J=8.72 Hz), 1.7 (s, 6H); MS (APCI) m/z 306 ([M+H]$^+$, 100%); Anal. Calc. For C$_{16}$H$_{13}$ClFNO$_2$: C, 62.86; H, 4.29; N, 4.58. Found: C, 62.98; H, 4.1; N, 4.6.

EXAMPLE 78

3-Chloro-5(4,4-dimethyl-2-oxo-1,4-dihydro-2H-benzo[d][1,3]oxazin-6-yl)-benzonitrile Prepared from (1,4-dihydro-4,4-dimethyl-2-oxo-2H-3,1-benzoxin-6-yl)boronic acid and 1-bromo-3-chlorobenzonitrile according to procedure B. A white solid: mp 256–257° C.; $^1$H-NMR (DMSO-d$_6$) δ10.4 (s, H), 8.22 (bs, 1H), 8.15 (bs, 1H), 7.98 (bs, 1H), 7.74–7.71 (m, 2H), 6.97 (d, 1H, J=8.09 Hz), 1.7 (s, 6H); MS (ESI) m/z 311 ([M–H]$^-$, 100%); Anal. Calc. For C$_{17}$H$_{13}$ClN$_2$O$_2$: C, 65.29; H, 4.19; N, 8.96. Found: C, 65.25; H, 3.92; N, 8.71.

EXAMPLE 79

6-(3,5-Dinitro-phenyl)-4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 1-bromo-3,5-dinitrobenzene according to procedure B. A yellow solid: mp 297–298° C.; $^1$H-NMR (DMSO-d) δ10.4 (s, 1H), 8.88 (d, 2H, J=1.98 Hz), 8.78 (bs, 1H), 7.78–7.82 (m, 2H), 7.04 (d, 1H, J=8.23 Hz), 1.7 (s, 6H); MS (APCI) m/z 343 ([M–H]$^-$, 100%); Anal. Calc. For C$_{16}$H$_{13}$N$_3$O$_6$: C, 55.98; H, 3.82; N, 12.24. Found: C, 55.65; H, 3.7; N, 11.92.

EXAMPLE 80

5-(4,4-Dimethyl-2-oxo-1,4-dihydro-2H-benzo[d][1,3]oxazin-6-yl)-isophthalonitrile Prepared from (1,4-dihydro-4,4-dimethyl-2-oxo-2H-3,1-benzoxin-6-yl)boronic acid and 5-bromoisophthalonitrile according to procedure B. A white solid: mp 288–289° C.; $^1$H-NMR (DMSO-d$_6$) δ10.4 (s, 1H), 8.58 (s, 2H), 8.40 (d, 1H, J=0.77 Hz), 7.80–7.75 (m, 2H), 6.99 (d, 1H, J=8.2 Hz), 1.7 (s, 6H); MS (EI) m/z 303 ([M$^+$], 20%); Anal. Calc. For C$_{18}$H$_{13}$N$_3$O$_2$ 1.65 H$_2$O: C, 64.92; H, 4.93; N, 12.62 Found: C, 64.74; H, 4.69; N, 12.32.

EXAMPLE 81

4,4-Dimethyl-6-(3-thiazol-2-yl-phenyl)-1,4-dihydro-benzo[d][1,3]oxazin-2-one

A mixture of 6-(3-bromo-phenyl)-4,4-dimethyl-1,4-dihydro-benzo[d][1,3]oxazin-2-one (0.25 g, 0.75 mmol), tri-n-butyl-thiazol-2-yl tin (0.5 g, 1.3 mmol) in DMF (5 mL) was degassed to remove oxygen and then heated under nitrogen at 90° C. for 3 hours. The reaction mixture was cooled to room temperature (rt) and treated with ice-water (70 mL). Ethyl acetate (100 mL) was added and organic layer was separated, washed with brine, and dried (MgSO$_4$). After removal of solvent, the residue was purified by a silica gel column (hexane:ethyl acetate/1:1) to give the title compound as a white solid (60 mg, 23%): mp 223–224° C.; $^1$H-NMR (DMSO-d$_6$) δ10.4 (s, 1H), 9.13 (s, 1H), 8.45 (s, 1H), 7.94 (bs, 1H), 7.67–7.61 (m, 4H), 7.53 (t, 1H, J=7.68 Hz), 7.00 (d, 1H, J=8.81 Hz), 1.7 (s, 6H); MS (APCI) m/z 337 ([M+H]$^+$, 100%); Anal. Calc. For C$_{19}$H$_{16}$N$_2$O$_2$S 0.25 H$_2$O: C, 66.94; H, 4.88; N, 8.22. Found: C, 66.57; H, 4.65; N, 7.92.

EXAMPLE 82

6-(3-Fluoro-5-methoxy-phenyl)-4,4-dimethyl-1,4-dihydro-benzo[d][1,3]oxazin-2-one Prepared from (1,4-dihydro-4,4-dimethyl-2-oxo-2H-3,1-benzoxin-6-yl)boronic acid and 3-bromo-5-fluoroanisole according to procedure B. A white solid: mp 181–182° C.; $^1$H-NMR (DMSO-d$_6$) δ10.4 (s, 1H), 7.62–7.59 (m, 2H), 7.13–7.06 (m, 2H), 6.97–6.94 (d, 1H, J=8.89 Hz), 6.80 (dt, 1H, J=10.95, 2.12 Hz), 3.8 (s, 3H), 1.7 (s, 6H); MS (ESI) m/z 302 ([M+H]$^+$, 100%); Anal. Calc. For C$_{17}$H$_{16}$FNO$_3$ 0.1 H$_2$O: C, 67.36; H, 5.39; N, 4.62. Found: C, 67.11; H, 5.44; N, 4.48.

EXAMPLE 83

6-(3-Fluoro-5-trifluoromethyl-phenyl)-4,4-dimethyl-1,4-dihydro-benzo[d][1,3]oxazin-2-one Prepared from (1,4-dihydro-4,4-dimethyl-2-oxo-2H-3,1-benzoxin-6-yl)boronic acid and 1-bromo-3-fluoro-5-trifluoromethylbenzene according to procedure B. A white solid: mp 207–208° C.; $^1$H-NMR (DMSO-d$_6$) δ10.4 (s, 1H), 7.94–7.9 (m, 2H), 7.73–7.7 (m, 2H), 7.63 (d, 1H, J=8.58 Hz), 6.99 (d, 1H, J=8.68 Hz), 1.7 (s, 6H); MS (EI) m/z 339 ([M$^+$], 60%); Anal. Calc. For C$_{17}$H$_{13}$F$_4$NO$_2$: C, 60.18; H, 3.86; N, 4.13. Found: C, 59.9; H, 3.99; N, 4.06.

EXAMPLE 84

6-(5-Bromo-pyridin-3-yl)-4,4-dimethyl-1,4-dihydro-benzo[d][1,3]oxazin-2-one

Prepared from (1,4-dihydro-4,4-dimethyl-2-oxo-2H-3,1-benzoxin-6-yl)boronic acid and 3,5-dibromopyridine according to procedure B. A white solid: mp 211–212° C.; $^1$H-NMR (DMSO-d$_6$) δ10.4 (s, 1H), 8.92 (d, 1H, J=1.9 Hz), 8.66 (d, 1H, J=2.09 Hz), 8.40 (t, H, J=2.02 Hz), 7.72–7.68 (m, 2H), 6.99 (d, 1H, J=8.1 Hz), 1.7 (s, 6H); MS (APCI) m/z 333 ([M+H]$^+$, 100%), 335 ([M+H]$^+$, 100%); Anal. Calc. For C$_{15}$H$_{13}$BrN$_2$O$_2$: C, 54.07; H, 3.93; N, 8.41. Found: C, 54.15; H, 3.89; N, 8.31.

EXAMPLE 85

6-(5-Bromo-1-oxy-pyridin-3-yl)-4,4-dimethyl-1,4-dihydro-benzo[d][1,3]oxazin-2-one A mixture of 6-(5-bromo-pyridin-3-yl)-4,4-dimethyl-1,4-dihydro-benzo[d][1,3]oxazin-2-one (0.34 g, 1 mmol), hydrogen peroxide (30%, 5 mL) in acetic acid (5 mL) was heated at 60° C. for 3 hours. The reaction mixture was cooled to rt and neutralized by addition of a cold saturated sodium bicarbonate solution. The white precipitate obtained was collected on a filter, washed with distilled water and dried to afford the title compound as a white solid (0.35 g, 100%): mp 157–159° C.; $^1$H-NMR (DMSO-d$_6$) δ10.4 (s, 1H), 8.69 (s, 1H), 8.53 (s, 1H), 7.99 (s, 1H), 7.73–7.69 (m, 2H), 6.97 (d, 1H, J=8.18 Hz), 1.7 (s, 6H); MS (APCI) m/z 349 ([M+H]$^+$, 100%), 351 ([M+H]$^+$, 100%); Anal. Calc. For $C_{15}H_{13}BrN_2O_3 \cdot 2.5\ H_2O$: C, 45.70; H, 4.60; N, 7.11. Found: C, 45.34; H, 4.64; N, 7.

EXAMPLE 86

6-(3-Cyano-5-fluoro-phenyl)-4,4-dimethyl-2-oxo-4H-benzo[d][1,3]oxazine-1-carboxylic acid tert-butyl ester A mixture of 3-(4,4-dimethyl-2-oxo-1,4-dihydro-2H-benzo[d][1,3]oxazin-6-yl)-5-fluorobenzonitrile (0.3 g, ~1 mmol), di-tert-butyl dicarbonate (0.33 g, 1.5 mmol), and DMAP (50 mg) in anhydrous acetonitrile was stirred at rt under nitrogen for 4 minutes. The reaction mixture was washed with 1N aqueous HCl, brine, dried ($MgSO_4$). After removal of solvent, the title compound was obtained as a white solid (0.25 g, 63%): mp 139–140° C.; $^1$H-NMR ($CDCl_3$-$d_6$) δ7.66–7.63 (m, 2H), 7.53–7.48 (m, 2H), 7.38–7.35 (m, 2H), 1.79 (s, 6H), 1.62 (s, 9H); MS (APCI) m/z 289 ([M–H]$^-$ 100%); Anal. Calc. For $C_{22}H_{21}FN_2O_4$: C, 66.66; H, 5.34; N, 7.07. Found: C, 66.7; H, 5.41; N, 7.

EXAMPLE 87

5-(4,4-Dimethyl-2-oxo-1,4-dihydro-2H-benzo[d][1,3]oxazin-6-yl)-2-fluoro-benzonitrile Prepared from (1,4-dihydro-4,4-dimethyl-2-oxo-2H-3,1-benzoxin-6-yl)boronic acid and 1-bromo-2-fluorobenzonitrile according to procedure B. A white solid: mp 255–256° C.; $^1$H-NMR (DMSO-$d_6$) δ10.4 (s, 1H), 8.30 (dd, 1H, J=6.15, 2.41 Hz), 8.12–8.07 (m, 1H), 7.76–7.58 (m, 3H), 6.97 (d, 1H, J=8.22 Hz), 1.7 (s, 6H); MS (APCI) m/z 297 ([M+H]$^+$, 100%); Anal. Calc. For $C_{17}H_{13}FN_2O_2 \cdot 0.1\ H_2O$: C, 68.50; H, 4.46; N, 9.40. Found: C, 68.27; H, 4.81; N, 9.1.

EXAMPLE 88

4-(8-Fluoro-4,4-dimethyl-2-oxo-1,4-dihydro-2H-benzo[d][1,3]oxazin-6-yl)-thiophene-2-carbonitrile 8-Fluoro-(1,4-dihydro-4,4-dimethyl-2-oxo-2H-3,1-benzoxin-6-yl)boronic acid was prepared from 6-bromo-8-Fluoro-4,4-dimethyl-dihydro-benzo[d][1,3]oxazin-2-one using the procedure of example 4.

The title compound was prepared from 8-fluoro-(1,4-dihydro-4,4-dimethyl-2-oxo-2H-3,1-benzoxin-6-yl)boronic acid and 4-bromo-2-cyanothiophene according to procedure B. A white solid: mp 250–251° C.; $^1$H-NMR (DMSO-$d_6$) δ10.5 (s, 1H), 8.54 (d, 1H, J=1.42 Hz), 8.43 (d, 1H, J=1.35 Hz), 7.69 (dd, 1H, J=11.71, 1.54 Hz), 7.58 (bs, 1H), 1.7 (s, 6H); MS (EI) m/z 302 ([M$^+$], 50%); Anal. Calc. For $C_{15}H_{11}FN_2O_2S \cdot 0.45\ H_2O$: C, 58.04; H, 3.86; N, 9.02 Found: C, 58.4; H, 3.89; N, 8.63.

EXAMPLE 89

3-Fluoro-5-(8-fluoro-4,4-dimethyl-2-oxo-1,4-dihydro-2H-benzo[d][1,3]oxazin-6-yl)-benzonitrile Prepared from 8-fluoro-(1,4-dihydro-4,4-dimethyl-2-oxo-2H-3,1-benzoxin-6-yl)boronic acid and 5-bromo-3-fluorobenzonitrile according to procedure B. A white solid: mp 256–257° C.; $^1$H-NMR (DMSO-$d_6$) δ10.5 (s, 1H), 8.20 (bs, 1H), 8.06 (dt, 1H, J=10.48, 2.16 Hz), 7.85–7.82 (m, 1H), 7.77 (dd, 1H, J=11.89, 1.81 Hz), 7.63 (s, 1H), 1.7 (s, 6H); MS (EI) m/z 314 ([M$^+$], 60%).

EXAMPLE 90

5-(4,4-Dimethyl-2-oxo-1,4-dihydro-2H-benzo[d][1,3]oxazin-6-yl)-thiophene-3-carbonitrile Prepared according to procedure B from (1,4-dihydro-4,4-dimethyl-2-oxo-2H-3,1-benzoxin-6-yl)boronic acid and 2-bromo-4-thiophenecarbonitrile. An off-white solid: mp 255–260° C.; $^1$H-NMR (DMSO-$d_6$) δ10.36 (s, 1H), 8.48(d, 1H, J=1.1 Hz), 7.88–7.87 (d, 1H J=1.3 Hz), 7.63 (d, 1H J=1.9 Hz), 7.56–7.54 (dd, 1H, J=8.0, 2.0 Hz), 6.93 (d, 1H, J=8.1 Hz), 1.64 (s, 6H). MS(–ESI) m/z 283 (M–H)$^-$.

EXAMPLE 91

2-(4,4-Dimethyl-2-oxo-1,4-dihydro-2H-benzo[d][1,3]oxazin-6-yl)-thiophene-3-carbonitrile Prepared according to procedure B from (1,4-dihydro-4,4-dimethyl-2-oxo-2H-3,1-benzoxin-6-yl)boronic acid and 2-bromo-3-thiophenecarbonitrile. An off-white solid: mp 200–202° C.; $^1$H-NMR (DMSO-$d_6$) δ10.49 (s, 1H), 7.75 (m, 1H), 7.63 (d, 1H, J=2.2 Hz), 7.59 (m, 1H), 7.50 (m, 1H), 7.02 (d, 1H, J=8.1 Hz), 1.63 (s, 6H); MS(–ESI) m/z 283 (M–H)$^-$.

EXAMPLE 92

6-(1,2,4-thiadiazol-3-yl-phenyl)-4,4-dimethyl-1,4-dihydro-benzo[d][1,3]oxazin-2-one A mixture of 5-[3-bromo-phenyl]-[1,3,4]oxathiazole-2-one (21.25 g, 82.3 mmol), ethylcyano formate (32.5 mL, 329 mmol) in o-xylene (500 mL) was heated to 150° C. for 60 hours. After the solvent was removed from the reaction mixture, the product was recrystallized from ethanol to give 3-[3-bromo-phenyl]-[1,2,4]thiadiazole-5-carboxylic acid ethyl ester as white crystals (17.5 g, 68%): mp 87–90° C.; $^1$H-NMR ($CDCl_3$) δ8.53 (t, 1H, J=1.76 Hz), 8.28 (dt, 1H, J=5.4, 1.2 Hz), 7.62 (dq, 1H, J=5.1, 1.0 Hz), 7.36 (t, 1H, J=7.9 Hz), 4.55 (q, 2H, J=7.1 Hz), 1.48 (t, 3H, J=7.1 Hz); MS ((+)APCI) [M+H]$^+$ @ m/z 313/315. Anal. Calc. For $C_{11}H_9BrN_2O_2S$: C, 42.19; H, 2.90; N, 8.94. Found: C, 41.81; H, 3.08; N, 8.78.

A mixture of 3-[3-bromo-phenyl]-[1,2,4]thiadiazole-5-carboxylic acid ethyl ester (16.8 g, 53.5 mmol), sodium hydroxide (2.4 g, 58.8 mmol), distilled water (120 mL), and ethanol (20 mL) was heated to 100° C. for 2 hours. The reaction mixture was cooled to room temperature. Concentrated hydrochloric acid (5.1 mL) was added, and the reaction mixture re-heated to 100° C. for 3 hours. The solution was cooled to room temperature and extracted with diethyl ether (3×150 mL). The combined organic layers were washed with distilled water (3×100 mL), and dried over $MgSO_4$. After the solvent was removed, 3-[3-bromo-phenyl]-[1,2,4]thiadiazole was obtained as white needles (12.7 g, 99%): mp 69–71° C.; $^1$H-NMR ($CDCl_3$) δ9.89 (s, 1H), 8.52 (t, 1H, J=1.8 Hz), 8.28 (dt, 1H, J=5.2, 1.3 Hz), 7.61 (dq, 1H, J=4.9, 1.1 Hz), 7.35 (t, 1H, J=7.9 Hz); MS ((+) APCI) [M+H]$^+$ @ m/z 241/243. Anal. Calc. For $C_8H_5BrN_2S$: C, 39.85; H, 2.09; N, 11.62. Found: C, 39.82; H, 2.43; N, 11.33.

According to procedure B, (1,4-dihydro-4,4-dimethyl-2-oxo-2H-3,1-benzoxazin-6-yl)boronic acid was coupled with 3-[3-bromo-phenyl]-[1,2,4]thiadiazole to yield 6-(1,2,4-thiadiazol-3-yl-phenyl)-4,4-dimethyl-1,4-dihydro-benzo[d][1,3]-oxazin-2-one as an off-white solid (0.5 g, 35%): mp 214–216° C.; $^1$H-NMR (DMSO-$d_6$) δ10.40 (s, 1H), 10.36 (s, 1H), 8.49 (s, 1H), 8.23 (d, 1H, J=7.7 Hz), 7.83 (d, 1H, J=7.9

Hz), 7.66–7.61 (m, 3H), 7.02 (t, 1H, J=4.4 Hz), 1.70 (s, 6H); MS ((+)APCI) [M+H]$^+$ @ m/z 338.

EXAMPLE 93

6-(3-Fluoro-5-thiophen-3-yl-phenyl)-4,4-dimethyl-1,4-dihydro-benzo[d][1,3]oxazin-2-one Prepared from 6-(3-bromo-5-fluoro-phenyl)-4,4-dimethyl-1,4-dihydro-benzo[d][1,3]oxazin-2-one and 3-thiophene boronic acid according to procedure B. A brownish-orange solid: mp 200–203° C.; $^1$H-NMR (CDCl$_3$) δ8.62 (s, 1H), 7.53 (q, 1H, J=1.4 Hz), 7.50 (d, 1H, J=1.5 Hz), 7.49 (d, 1H, J=2.0 Hz), 7.45–7.40 (m, 1H), 7.35 (d, 1H, J=1.8 Hz), 7.27–7.24 (m, 2H), 7.15 (dt, 1H, J=5.8, 2.0 Hz), 694 (d, 1H, J=8.2 Hz), 1.80 (s, 6H); MS ((−)APCI) [M–H]$^-$ @ m/z 352. Anal. Calc. For C$_{20}$H$_{16}$FNO$_2$S 0.50 H$_2$O: C, 66.28; H, 4.73; N, 3.87. Found: C, 66.54; H, 5.03; N, 3.52.

EXAMPLE 94

2-(4,4-Dimethyl-2-oxo-1,4dihydro-2H-benzo[d][1,3]oxazin-6-yl)-pyrrole-1-carboxylic acid tert-butyl ester A solution of 6-bromo-4,4-dimethyl-1,4-dihydro-benzo[d][1,3]oxazin-2-one (0.87 g, 3.4 mmol) and tetrakis(triphenylphosphine)palladium(0) (96 mg, 0.08 mmol) in toluene (40 mL) was stirred under a flow of nitrogen for 25 min. To the solution was added sequentially 1-t-butoxycarbonylpyrrole-2-boronic acid (1.4 g, 7.0 mmol) in absolute ethanol (10 mL) and potassium carbonate (0.94 g, 7.0 mmol) in water (10 mL). The mixture was heated at 80° C. for 16 h and allowed to cool to rt. The reaction mixture was poured into aqueous saturated sodium bicarbonate solution (100 mL) and extracted with ethyl acetate (3×100 mL). The organic layers were combined, washed with water (100 mL) and brine (50 mL) and dried over magnesium sulfate. The solution was filtered, concentrated in vacuo, and the residue was purified by flash column chromatography on silica gel (30% ethyl acetate/hexane) to give the title compound as an off-white powder (0.7 g, 62%): mp 176° C. $^1$H NMR (CDCl$_3$) δ1.40 (s, 9H), 1.73 (s, 6H), 6.17 (dd, 1H, J=1.8, 3.3 Hz), 6.22 (dd, 1H, J=3.3, 3.3 Hz), 6.77 (d, 1H, J=8.1 Hz), 7.13 (d, 1H, J=1.8 Hz), 7.23 (dd, 1H, J=1.8, 8.1 Hz), 7.33 (dd, 1H, J=1.8, 3.3 Hz), 7.69 (bs, 1H). MS ((−) ESI) m/z 341 [M–H]$^-$. Anal. Calcd for C$_{19}$H$_{22}$N$_2$O$_4$: C, 66.65; H, 6.48; N, 8.18. Found: C, 65.46; H, 6.51; N, 7.74.

EXAMPLE 95

2-(4,4-Dimethyl-2-oxo-1,4-dihydro-2H-benzo[d][1,3]oxazin-6-yl)-5-nitro-pyrrole-1-carboxylic acid tert-butyl ester To a solution of 2-(4,4-dimethyl-2-oxo-1,4-dihydro-2H-benzo [d][1,3]oxazin-6-yl)-pyrrole-1-carboxylic acid tert-butyl ester (0.7 g, 2.0 mmol) in acetonitrile (25 mL) and dichloromethane (1 mL) at room temperature was added silver nitrate (0.37 g, 2.1 mmol). After 5 min, acetyl chloride (0.15 mL, 2.0 mmol) in acetonitrile (3 mL) was added and the solution was allowed to stir for 2 h. The reaction mixture was poured into water (50 mL) and extracted with ethyl ether (2×50 mL). The organic layers were combined, washed with brine (30 mL) and dried over magnesium sulfate. The solution was filtered, concentrated in vacuo and the residue was purified by flash column chromatography on silica gel (30% ethyl acetate/hexane) to give a yellow oil which crystallized from 5% ethyl acetate/hexane to give the title compound as a bright yellow powder (350 mg, 45%): mp 125° C. $^1$H NMR (CDCl$_3$) δ1.47 (s, 9H, 1.75 (s, 6H), 6.26 (d, 1H, J=4.2 Hz), 6.87 (d, 1H, J=8.1 Hz), 7.19 (d, 1H, J=4.2 Hz), 7.34 (d, 1H, J=2 Hz), 7.4 (dd, 1H, J=1.8, 8.1 Hz), 8.17 (bs, 1H). MS ((+) APCI) m/z 388 [M+H]$^+$. Anal. Calcd for C$_{19}$H$_{21}$N$_3$O$_6$: C, 58.91; H, 5.46; N, 10.85. Found: C, 58.4; H, 5.55; N, 10.18.

EXAMPLE 96

4,4-Dimethyl-6-(5-nitro-1H-pyrrol-2-yl)-1,4-dihydrobenzo[d][1,3]oxazin-2-one 2-(4,4-dimethyl-2-oxo-1,4-dihydro-2H-benzo[d][1,3]oxazin-6-yl)-5-nitro-pyrrole-1-carboxylic acid tert-butyl ester (0.7 g, 1.8 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 180° C. After 10 min at this temperature, the flask was removed from the oil bath and allowed to cool to rt. The brown residue was washed into a larger flask with dichloromethane/ethyl acetate and adsorbed onto a small amount of silica gel. Purification by flash column chromatography on silica gel (60% ethyl acetate/hexane) gave the title compound as a brown powder (200 mg, 40%): mp 265° C. (dec). $^1$H NMR (DMSO-d$_6$) δ1.65 (s, 6H), 6.81 (d, 1H, J=4.4 Hz), 6.90 (d, 1H, J=8.6 Hz), 7.25 (d, 1H, J=4.2 Hz), 7.79 (dd, 1H, J=2, 8.3 Hz), 7.91 (d, 1H, J=2 Hz), 10.37 (s, 1H), 13.17 (bs, 1H), MS ((−) ESI) m/z 286 [M–H]$^-$. Anal. Calcd for C$_{14}$H$_{13}$N$_3$O$_4$: C, 58.53; H, 4.56; N, 14.63. Found: C, 58.25; H, 5.10; N, 12.57.

EXAMPLE 97

4,4-Dimethyl-6-(1H-pyrrol-2-yl)-1,4-dihydro-benzo[d][1,3]-oxazin-2-one 2-(4,4-Dimethyl-2-oxo-1,4-dihydro-2H-benzo[d][1,3]oxazin-6-yl)-pyrrole 1-carboxylic acid tert-butyl ester (3.5 g, 10 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 180° C. After 10 min at this temperature, the flask was removed from the oil bath and allowed to cool. The brown residue was washed into a larger flask with dichloromethane/ethyl acetate and adsorbed onto a small amount of silica gel. Purification by flash column chromatography on silica gel (60% ethyl acetate/hexane) gave the title compound as a green solid (2 g, 80%): mp 202° C. (dec). $^1$H NMR (CDCl$_3$) δ1.75 (s, 6H), 6.30 (m, 1H), 6.45 (m, 1H), 6.85 (d, 1H, J=8.5 Hz), 6.86 (m, 1H), 7.24 (d, 1H, J=2 Hz), 7.33 (dd, 1H, J=2, 8.4 Hz), 8.44 (bs, 1H), 8.66 (s, 1H). MS ((+) APCI) m/z 243 [M+H]$^+$. Anal. Calcd for C$_{14}$H$_{14}$N$_2$O$_2$: C, 69.41; H, 5.82; N, 11.56. Found: C, 69.20; H, 5.96; N, 11.29.

EXAMPLE 98

4,4-Dimethyl-6-(1-methyl-1H-pyrrol-2-yl)-1,4-dihydro-benzo[d][1,3]oxazin-2-one

To a mixture of 4,4-dimethyl-6-(1H-pyrrol-2-yl)-1,4-dihydro-benzo[d][1,3]oxazin-2-one (1.5 g, 6.2 mmol) in dimethylformamide (20 mL) at room temperature was added sequentially potassium carbonate (4.28 g, 31 mmol) and a solution of methyl iodide (1.16 mL, 19 mmol) in dimethylformamide (5 mL). After 1 h, the reaction mixture was boiled. The reaction was cooled to room temperature, poured into water (50 mL) and extracted with ethyl ether (2×50 mL). The organic layers were combined, washed with brine (30 mL), dried over magnesium sulfate, filtered and concentrated in vacuo. Purification by flash column chromatography on silica gel (40% ethyl acetate/hexane) gave the title compound as an off-white powder (0.5 g, 31%) mp 230° C. $^1$H NMR (CDCl$_3$) δ1.71 (s, 6H), 3.42 (s, 3H), 6.31 (dd, 1H, J=2.9, 5.9 Hz), 6.47 (m, 1H), 6.88 (m, 1H), 6.94 (d, 1H, J=8.6 Hz), 7.26 (d, 1H, J=2.2 Hz), 7.41 (dd, 1H, J=2.2, 8.6 Hz), 8.43 (bs, 1H). MS ((−) ESI) m/z 255 [M−H]$^−$. Anal. Calcd for C$_{15}$H$_{16}$N$_2$O$_2$: C, 70.29; H, 6.29; N, 10.93. Found: C, 68.59; H, 6.16; N, 10.49.

EXAMPLE 99

4,4-Dimethyl-6-(1-methyl-5-nitro-1H-pyrrol-2-yl)-1, 4-dihydro-benzo[d][1,3]oxazin-2-one To a solution of 4,4-dimethyl-6-(1-methyl-1H-pyrrol-2-yl)-1,4-dihydro-benzo[d][1,3]oxazin-2-one (0.3 g, 1.2 mmol) in acetonitrile (20 mL) was added silver nitrate (0.21 g, 1.26 mmol). The solution was cooled to −78° C. and treated with a solution of acetyl chloride (0.08 mL, 1.2 mmol) in acetonitrile (1 mL). The reaction mixture was allowed to warm to room temperature. After 1 h, the reaction mixture was poured into water (50 mL) and extracted with ethyl ether (2×50 mL). The organic layers were combined, washed with brine (30 mL), dried over magnesium sulfate, filtered and concentrated in vacuo. Purification by flash column chromatography on silica gel (40% ethyl acetate/hexane) gave the title compound (5 mg, 1%) as a yellow solid, mp 180–185° C. $^1$H NMR (CDCl$_3$) δ1.75 (s, 6H), 3.45 (s, 3H), 6.57 (dd, 1H, J=2.9, 4.3 Hz), 7.04 (d, 1H, J=8.5 Hz), 7.22 (dd, 1H, J=2.5, 4.3 Hz), 7.36 (d, 1H, J=2.1 Hz), 7.56 (dd, 1H, J=2.1, 8.5 Hz), 9.67 (bs, 1H. MS ((+) APCI) m/z 302 [M+H]$^+$.

EXAMPLE 100

5-Bromo-4-ethylthiophene-2-carboxaldehyde

Prepared from 2-bromo-3-ethylthiophene in a similar manner to the example 19. $^1$H-NMR(DMSO-d$_6$) δ9.82 (s, 1H), 7.81 (s, 1H), 2.5 (q, 2H, J=7.4 Hz), 1.15 (t, 3H, J=7.5 Hz).

EXAMPLE 101

5-Bromo-4-ethylthiophene-2 carbonitrile

Prepared from 5-bromo-4-ethylthiophene-2-carboxaldehyde using the similar procedure of example 18. IR(KBr) 2221 cm$^{-1}$; $^1$H-NMR (DMSO-d$_6$) δ7.87 (s, 1H), 2.55 (q, 2H, J=7.3 Hz), 1.18 (t, 3H, J=7.6 Hz). MS (EI) m/z 215/217(M$^+$).

EXAMPLE 102

5Bromo-4-n-propylthiophene-2-carboxaldehyde

Prepared from 2-bromo-3-n-propylthiophene in a similar manner to the example 19. $^1$H-NMR(DMSO-d$_6$) δ9.82 (s, 1H), 2.6–2.5 (m, 2H), 1.65–1.51 (m, 2H), 1.0 (t, 3H, J=4.7 Hz).

EXAMPLE 103

5-Bromo-4-n-propylthiophenecarbonitrile

Prepared from 5-bromo-4-n-propylthiophene-2-carboxaldehyde using the similar procedure of example 18. $^1$H-NMR(DMSO-d$_6$) δ7.87 (s, 1H), 2.5 (t, 2H, J=5.2 Hz), 1.64–1.5 (m, 2H), 1.91 (t, 3H, J=5.1 Hz). MS(EI) m/z 229–231(M$^+$).

EXAMPLE 104

5-Bromo-4-n-butylthiophenecarboxaldehyde

Prepared from 2-bromo-3-n-butylthiophene in a similar manner to the example 19. IR(KBr) 1660 cm$^{-1}$. $^1$H-NMR (DMSO-d$_6$) δ9.78 (s, 1H), 7.85 (s, 1H), 2.57–2.53 (m, 2H), 1.57–1.53 (m, 2H), 1.32–1.25 (m, 2H), 0.88 (t, 3H, J=5.2 Hz). MS (EI) m/z 246(M$^+$).

EXAMPLE 105

5-Bromo-4-n-butylthiophenecarbonitrile

Prepared from 5-bromo-4-n-butylthiophenecarboxaldehyde using the similar procedure of example 18. $^1$H-NMR(DMSO-d$_6$) δ7.87 (s, 1H), 2.58–2.44 (m, 2H), 1.65–1.48 (m, 2H), 1.38–1.23 (m, 2H), 0.89 (t, 3H, J=5.3 Hz). MS (EI) m/z 243 (M$^+$).

EXAMPLE 106

3-(1,2-Dihydro-2-oxospiro[4H-3,1-benzoxazine-4,1-cyclohexan]-6-yl)-benzonitrile

Prepared according to Procedure B from spiro-(4,1'-cyclohexane-1,4-dihydro-2-oxo-2H-3,1-benzoxazin-6-yl) boronic acid and 3-bromobenzonitrile. Tan powder: mp 245–247° C. $^1$H-NMR(DMSO-d$_6$) δ10.31 (s, 1H), 8.21 (s, 1H), 8.02 (d, 1H, J=8.0 Hz), 7.78 (d, 1H, J=7.7 Hz), 7.68–7.61 (n, 3H), 6.97 (d, 1H, J=8.2 Hz), 1.98–1.96 (m, 4H), 1.75–1.64 (m, 5H), 1.40–1.32 (m, 1H). MS (EI) m/z 318 [M$^+$]. Anal. Calc. For C$_{20}$H$_{18}$N$_2$O$_2$.1/2 H$_2$O: C 73.38; H, 5.85; N, 8.56. Found: C, 73.86; H, 5.81; N, 8.22.

EXAMPLE 107

3-(1,2-Dihydro-2-oxospiro[4H-3,1-benzoxazine-4,1-cyclohexan]-6-yl)-5-fluorobenzonitrile Prepared according to Procedure B from spiro-(4,1'-cyclohexane-1,4-dihydro-2-oxo-2H-3,1-benzoxazin-6-yl) boronic acid and 3-bromo-5-fluorobenzonitrile. White powder: mp 250–253° C. IR (KBr) 2220 cm$^{-1}$. $^1$H-NMR (DMSO-d$_6$) δ10.34 (s, 1H), 8.13 (s, 1H), 8.0 (d, 1H, J=10.6 Hz), 7.80–7.7 (m, 3H), 6.98–6.95 (d, 1H, J=8.1 Hz), 1.99–1.97 (m, 4H), 1.76–1.65 (m, 6H), 1.37–1.33 (m, 1H). MS (EI) m/z 336 (M$^+$). A Calc. For C$_{20}$H$_{17}$FN$_2$O$_2$H$_2$O: C, 67.78; H, 5.40; N, 7.90. Found: C, 67.9; H, 4.93; N, 7.67.

EXAMPLE 108

4-(1,2-Dihydro-2-oxospiro[4H-3,1-benzoxazine-4,1-cyclohexan]-6-yl)-2-thiophenecarbonitrile Prepared according to Procedure B from spiro-(4,1'-cyclohexane-1,4-dihydro-2-oxo-2H-3,1-benzoxazin-6-yl) boronic acid and 3-bromo-5-cyanothiophene. White crystals: mp 230–232° C. IR (KBr) 2200 cm$^{-1}$. $^1$H-NMR (DMSO-d$_6$) δ10.29 (s, 1H), 8.49 (s, 1H), 8.33 (s, 1H), 7.69–7.63 (m, 2H), 6.93–6.91 (d, 1H, J=8.2 Hz), 199–187

(m, 4H), 1.73–1.64 (m, 5H), 1.38–1.31 (m, 1H). MS(+) APCI m/z 325 (M+H)+. Anal. Calc. For $C_{18}H_{16}N_2O_2S1/4H_2O$: C, 65.73; H, 5.06; N, 8.52. Found: C, 65.55; H, 506; N, 8.22.

EXAMPLE 109

5-(1,2-Dihydro-2-oxospiro[4H-3,1-benzoxazine-4,1′-cyclohexan]-6-yl)-2-thiophenecarbonitrile Prepared according to Procedure B from spiro-(4,1′-cyclohexane-1,4-dihydro-2-oxo-2H-3,1-benzoxazin-6-yl) boronic acid and 2-bromo-5-cyanothiophene Tan powder: mp 243–245° C. $^1$H-NMR(DMSO-$d_6$) δ10.41(s, 1H), 7.98–7.97 (d, 1H, J=3.9 Hz), 7.67–7.60 (m, 3H), 6.97–6.94 (d, 1H, J=8.3 Hz), 1.98–1.92 (m, 4H), 174–164 (m, 5H), 1.45–1.21 (m, 1H). MS (EI) m/z 324 (M+). Anal. Calc. For $C_{18}H_{16}N_2O_2S$ 1/2 $H_2O$: C, 65.08; H, 5.04; N, 8.18. Found: C, 64.84; H, 5.09; N, 8.40.

EXAMPLE 110

5-(1,2-Dihydro-2-oxospiro[4H-3,1-benzoxazine-4,1′-cyclohexan]-6-yl)-4-methyl-2-thiophenecarbonitrile Prepared according to Procedure B from spiro-(4,1′-cyclohexane-1,4-dihydro-2-oxo-2H-3,1-benzoxazin-6-yl) boronic acid and 2-bromo-3-methyl-5-cyanothiophene. White powder: mp 200–203° C. $^1$H-NMR (DMSO-$d_6$) δ10.4 (s, 1H), 7.85 (s, 1H), 7.43–7.40 (m, 2H), 7.0 (d, 1H, J=8.8 Hz), 2.27 (s,3H), 2.00–1.62 (m, 9H), 1.42–123 (m, 1H). MS(EI) m/z 338 (M+). Anal. Calc. For $C_{19}H_{18}N_2O_2S$: C, 67.43; H, 5.36; N, 8.28. Found: C, 67.12; H, 5.45; N, 8.05.

EXAMPLE 111

5-(4,4-Dimethyl-2-oxo-1,4-dihydro-2H-benzo[d][1,3]oxazin-6-yl)-4-ethyl-thiophene-2-carbonitrile Prepared according to Procedure B from spiro-(4,1′-cyclohexane-1,4-dihydro-2-oxo-2H-3,1-benzoxazin-6-yl) boronic acid and 2-bromo-3-ethyl-5-cyanothiophene. White crystals: mp 160–162° C. $^1$H-NMR(DMSO-$d_6$) δ10.46 (s, 1H), 7.96 (s, 1H), 7.40–7.38 (m, 2H), 7.02–6.99 (d, 1H, J=8.8 Hz), 2.61 (q, 2H, J=7.5 Hz), 164 (s, 6H), 1.16 (t, 3H, J=7.6 Hz). MS (+) APCI m/z [M+H+ 313. Anal. Calc. For $C_{17}H_{16}N_2O_2S.1/4 H_2O$: C, 64.43; H, 5.25; N, 8.84. Found: C, 64.77; H, 5.23; N, 8.68.

EXAMPLE 112

5-(4,4-Dimethyl-2-oxo-1,4-dihydro-2H-benzo[d][1,3]oxazin-6-yl)-4-n-proyl-thiophene-2-carbonitrile Prepared according to Procedure B from spiro-(4,1′-cyclohexane-1,4-dihydro-2-oxo-2H-3,1-benzoxazin-6-yl) boronic acid and 2-bromo-3-n-propyl-5-thiophenecarbonitrile. White crystals: mp 160–162° C. IR (KBr) 2220 cm$^{-1}$. $^1$H-NMR(DMSO-$d_6$) δ10.47 (s, 1H), 7.93 (s, 1H), 7.38–7.36 (m, 2H), 7.01 (d, 1H, J=8.7 Hz), 2.59–2.48 (m, 2H), 1.64–1.51 (m, 2H), 0.85 (t, 3H, J=7.3 Hz). MS(−-ESI) m/z [M–H]− 325. Anal. Calc. For $C_{18}H_{18}N_2O_2S.3/4 H_2O$: C, 63.60; H, 5.78; N, 8.24. C, 63.48; H, 5.59; N, 8.04.

EXAMPLE 113

5-(4,4-Dimethyl-2-oxo-1,4-dihydro-2H-benzo[d][1,3]oxazin-6-yl)-4-n-butyl-thiophene-2-carbonitrile Prepared according to Procedure B from spiro-(4,1′-cyclohexane-1,4-dihydro-2-oxo-2H-3,1-benzoxazin-6-yl) boronic acid and 2-bromo-3-n-butyl-5-thiophenecarbonitrile. White crystals: mp 167–168° C. $^1$H-NMR(DMSO-$d_6$) δ10.46 (s, 1H), 7.93 (s, 1H), 7.38–7.36 (m, 2H), 7.01 (d, 1H, J=8.7 Hz), 2.59 (t, 2H, J=8.1 Hz), 1.63 (s, 6H), 1.58–1.51 (m, 2H), 1.48–1.17 (m, 2H), 0.82 (t, 3H, J=7.4 Hz), MS(−ESI) m/z [M–H]− 339. Anal. Calc. For $C_{19}H_{20}N_2O_2S.1/4 H_2O$: C, 66.16; H, 5.99; N, 8.12. Found: C, 66.33; H, 5.92; N, 7.85.

EXAMPLE 114

6-(4-Cyano-3-fluorophenyl)-4,4-dimethyl-1,4-dihydrobenzo[d]1,3]-oxazin-2-one

A solution of 4-cyano-3-fluoro-bromobenzene (0.6 g, 3.0 mmol), and tetrakis(triphenylphosphine)palladium(0) (0.2 g) in ethylene glycol dimethyl ether (20 mL) was stirred under $N_2$ for 20 minutes. To this mixture was then added (1,4-dihydro-4,4-dimethyl-2-oxo-2H-3,1-benzoxazin-6-yl) boronic acid (1.0 g, 4.5 mmol) and sodium carbonate (1.1 g, 10.6 mmol) in water (5 mL). The solution was brought to reflux for 18 hours and then cooled to room temperature, poured into 2N NaOH and extracted with EtOAc (3×50 mL). The combined extracts were washed with water, brine, dried (MgSO$_4$), and evaporated. The residue was purified by column chromatography (SiO$_2$, EtOAc:hexane=1:2) to afford the title compound (0.05 g, 6%) as an off-white solid. mp: 272–275° C.; $^1$H-NMR (DMSO-$d_6$) δ10.4 (s, 1H), 8.0 (t, 1H, J=7.7 Hz), 7.9 (dd, 1H, J=10.3,1.3 Hz), 7.8 (dd, 1H, J=6.8, 1.4 Hz), 7.7 (m, 2H), 6.9 (d, 1H, J=8.9 Hz), 1.7 (s, 6H); MS (EI) M+ @ m/z 296.

EXAMPLE 115

6-(4-Fluoro-phenyl)-4,4-dimethyl-1,4-dihydro-benzo[d][1,3]-oxazin-2-one

Prepared according to Procedure B from (1,4-dihydro-4,4-dimethyl-2-oxo-2H-3,1-benzoxin-6-yl)boronic acid and 1-bromo-4-fluorobenzene. Off-white crystals: mp 232–233° C. $^1$H-NMR(DMSO-$d_6$) δ10.3 (s, 1H), 7.74 (m, 2H), 7.53 (m, 2H), 7.28 (m, 2H), 6.96 (d, 1H, J=8.9 Hz), 1.63 (s, 6H).

EXAMPLE 116

6-(3,4-Difluoro-phenyl)-4,4-dimethyl-1,4-dihydro-benzo[d][1,3]oxazin-2-one

Prepared according to Procedure B from (1,4-dihydro-4,4-dimethyl-2-oxo-2H-3,1-benzoxin-6-yl)boronic acid and 1-bromo-3, 4-difluorobenzene. Off-white crystals: mp 207–208° C. $^1$H-NMR(DMSO-$d_6$) δ10.35 (s, 1H), 7.79 (m, 1H), 7.40–7.63 (m, 4H), 6.95 (d, 1H, J=8.9 Hz), 1.62 (s, 6H).

EXAMPLE 117

6-(2-Fluoro-phenyl)-4,4-dimethyl-1,4-dihydro-benzo[d][1,3]-oxazin-2-one

Prepared according to Procedure B from (1,4-dihydro-4,4-dimethyl-2-oxo-2H-3,1-benzoxin-6-yl)boronic acid and 1-bromo-2-fluorobenzene. Off-white crystals: mp 164–165° C. $^1$H-NMR(DMSO-$d_6$) δ10.33 (s, 1H), 7.56 (n, 1H), 7.25–7.45 (m, 4H) 6.98 (d, 1H, J=8.7 Hz), 1.64 (s, 6H).

EXAMPLE 118

3-(4,4-Dimethyl-2-oxo-1,4-dihydro-2H-benzo[d][1,3]-oxazin-6-yl)phenylacetonitrile Prepared from 3-bromophenylacetonitrile and (1,4-dihydro-4,4-dimethyl-2-oxo-2H-3,1-oxazin-6-yl)boronic acid. White solid: mp 188–190° C.; $^1$H-NMR (DMSO-$d_6$) δ10.33 (s, 1H), 7.62 (m, 2H), 7.55 (m, 2H), 7.48 (d, 1H, J=8.00 Hz), 7.33 (d, 1H, J=7.57 Hz), 6.99 (d, 1H, J=8.81 Hz), 4.09 (s, 2H), 1.67 (s, 6H); MS m/z 291(M−H). Anal. Calc. For $C_{18}H_{16}N_2O_2$·0.3 $H_2O$: C, 72.61; H, 5.62; N, 9.41. Found: C, 73.00; H, 5.43; N, 8.81

EXAMPLE 119

5-(4,4-Dimethyl-2-oxo-1,4-dihydro-2H-benzo[d][1,3]oxazin-6-yl)-furan-2-carbonitrile The title compound was prepared according to the procedure B from 2-bromo-5-cyanofuran (1.0 g, 5.6 mmol) (J. Med. Chem. (1997), 40(23), 3804–3819) and (1,4-dihydro-4,4-dimethyl-2-oxo-2H-3,1-benzoxazin-6-yl)boronic acid (1.8 g, 8.18 mmol) as a white solid (0.39 g, 1.45 mmol, 17%): mp. 257–260° C.; $^1$H-NMR (DMSO-$d_6$) δ10.48 (s, 1H), 7.73–7.70 (m, 3H), 7.19 (d, 1H, J=3.8 Hz), 6.98 (d, 1H, J=8.9 Hz), 1.66 (s, 6H); MS ((+)-APCI) m/z=269 (M+H)$^+$.

EXAMPLE 120

3-(4,4-Dimethyl-2-oxo-1,4-dihydro-2H-benzo[d][1,3]oxazin-6-yl)-2-fluoro-benzonitrile A solution of 3-bromo-2-fluorobenzoic acid (0.219 g, 1 mmol) in dry methanol (5 mL) under nitrogen was treated with trimethylorthoformate (0.22 mL, 2 mmol) and p-toluenesulfonic acid (catalytic amount), and then heated under reflux. After 16 h, the mixture was evaporated and the residue partitioned between water and $Et_2O$. the organic layer was washed with sat. sodium hydrogen carbonate solution, water, brine, dried (MgSO$_4$) and evaporated to give methyl 3-bromo-2-fluorobenzoate (0.195 g, 0.84 mmol, 84%): $^1$H-NMR (CDCl$_3$) δ7.90–7.85 (m, 1H), 7.71–7.65 (m, 1H), 7.10 (dt, 1H, J=8.0, 1.0 Hz), 3.94 (s, 3H): MS (EI) 232 (M$^+$).

A solution of the last cited compound (3.077 g, 13.2 mmol) in dry toluene (80 mL) at −78° C. under nitrogen was treated with a di-iso-butylaluminum hydride in toluene (1M, 15.7 mL, 15.7 mmol). After 1 h at −78° C., the mixture was quenched with aqueous HCl (3M, 16 mL). The mixture was warmed to RT, partitioned between EtOAc/$H_2O$, the aqueous layer was re-extracted with EtOAc, and the combined organic layers were washed with water, dried (MgSO$_4$) and evaporated to afford 3-bromo-2-fluorobenzaldehyde (2.63 g, 12.9 mmol, 98%), which was used without further purification: $^1$H-NMR (CDCl$_3$) δ10.35 (s, 1H), 7.82 (r, 2H), 7.18 (t, 7.8 Hz).

A mixture of the last cited compound (2.63 g, 12.9 mmol), hydroxylamine hydrochloride (1.0 g, 14 mmol) and potassium acetate (1.37 g, 14 mmol) was placed in ethanol/$H_2O$ (60 mL, 8:2) and the mixture was heated under reflux. After 30 min. the mixture was cooled, evaporated and partitioned between EtOAc and water. The organic layer was washed with brine, dried (MgSO$_4$) and evaporated to give 3-bromo-2-fluorobenzaldoxime which was used without further characterization.

A solution of the last cited compound (0.75 g, 3.43 mmol) and tetrakis(triphenylphosphine) palladium(0) (0.2 g) were stirred in dimethoxy ethane (30 mL) at room temperature under nitrogen. After 15 min., (1,4-dihydro-4,4-dimethyl-2-oxo-2H-3,1-benzoxazin-6-yl)boronic acid (1.1 g, 5.0 mmol) and sodium carbonate (1.35 g) in water (10 mL) were added and the mixture heated under reflux. After 16 h., the mixture was cooled, partitioned between water and EtOAc, the organic layer was washed with sat. sodium carbonate solution, brine, dried (MgSO$_4$) and evaporated. The residue was then dissolved in acetonitrile (50 mL), treated with copper acetate (0.2 g) and heated under reflux. After 16 h, the mixture was cooled and evaporated. The residue was partitioned between water and EtOAc, the organic layer was then washed with dilute sulfuric acid (1N), water, brine, dried (MgSO$_4$) and evaporated. The residue was then subjected to column chromatography (SiO$_2$, EtOAc/hexane, gradient elution), and then crystallized from EtOAc-hexane to afford the title compound (0.176 g, 0.59 mmol, 17%) as a white solid: mp. 192–198° C.; $^1$H-NMR (CDCl$_3$) δ9.15 (s, 1H), 7.69–7.58 (m, 2H), 7.42–7.31 (m, 3H), 6.99 (d, 1H, J=8.2 Hz), 1.78 (s, 6H); MS ((+)ESI) 297 [M+H]$^+$.

EXAMPLE 121

Pharmacology

The compounds of this invention were tested in the relevant assay as described below and their potency are in the range of 0.01 nM to 5 μM in the in vitro assays and 0.001 to 300 mg/kg in the in vivo assays.

TABLE 1

Potency of the selected cyclocarbamate derivatives as PR antagonists in some in vitro and in vivo models:

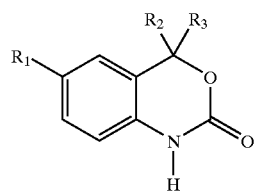

| Compound | $R_1$ | $R_2$ | $R_3$ | hPR Decidualization IC$_{50}$ (nM) | CV-1 IC$_{50}$ (mg/kg) |
|---|---|---|---|---|---|
| 1 | 3-cyano-4-fluorophenyl | Me | Me | 55 | 80% @ 1** |
| 2 | 3-fluoro-5-trifluormethyl-phenyl | Me | Me | 54 | 50% @ 1 |

TABLE 1-continued

Potency of the selected cyclocarbamate derivatives as PR antagonists in some in vitro and in vivo models:

| Compound | $R_1$ | $R_2$ | $R_3$ | hPR Decidualization $IC_{50}$ (nM) | CV-1 $IC_{50}$ (mg/kg) |
|---|---|---|---|---|---|
| 3 | 3-fluorophenyl | Me | Me | 6 | 80% @ 3 |
| 4 | 3,5-dichlorophenyl | Me | Me | 134 | 60% @ 1 |
| 5 | 5-cyano-2-fluorophenyl | Me | Me | 68 | 60% @ 1 |
| 6 | 3-fluoro-5-nitrophenyl | Me | Me | 11.5 | 50% @ 1 |
| 7 | 7-(2-cyanofuryl) | Me | Me | 30 | 75% @ 3 |
| 8 | 3-bromo-5-fluorophenyl | Me | Me | 11 | 50% @ 3 |
| 9 | 3-cyano-4-fluorophenyl | Me | Me | 13 | 6.96 ± 0.84 |
| 10 | 5-(2-cyano-4-methylthiophenyl | spirocyclohexyl | | 2.7 | 50% @ 10 |
| 11 | 5-(2-cyanothiophenyl) | spirocyclohexyl | | 12 | 50% @ 10 |
| 12 | 5-(2-cyanothiophenyl) | Me | Me | 19 | 3.34 ± 0.22 |
| 13 | 3-bromophenyl | Me | Me | 11.5 | 3 |
| 14 | 3-chloro-5-fluorophenyl | Me | Me | 22 | 50% @ 3 |
| 15 | 3-cyano-5-fluorophenyl | cyclopropyl | cyclopropyl | 22 | 3 |
| 16 | 5-(3-bromopyridyl) | Me | Me | 26 | 50% @ 3 |
| 17 | 4-(2-cyanothiophenyl) | Me | Me | 12.7 | 2.3 ± 0.46 |
| 18 | 5-(2-cyano-4-methylthiophenyl) | Me | Me | 5.23 | 1.5 |
| 19 | 3-cyano-5-fluorophenyl | Me | Me | 13.8 | 0.35 |
| 20 | 3-chloro-4-fluorophenyl | Me | Me | 37 | 1 |

ND, not determined;
**Percentage inhibition at the dose specified

A. In-vitro Biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4) T47D cell alkaline phosphatase assay, which is a further functional assay which also provides agonist and antagonist data.

1. hPR Binding Assay

This assay is carried out in accordance with: Pathirana, C.; Stein, R. B.; Berger, T. S.; Fenical, W.; Ianiro, T.; Mais, D. E.; Torres, A.; Glodman, M. E., Nonsteroidal human progesterone receptor modulators from the marine alga cymoplia barbata, J. Steroid Biochem. Mol. Biol., 1992, 41, 733–738.

2. PRE-luciferase assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium

The growth medium was as follows:

DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase assay

Stock CV-1 cells are maintained in growth medium Co-transfection is done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 µl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty µl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in full dose-response curves and the $EC_{50}$ or $IC_{50}$ values are calculated.

TABLE 2

Estimated $EC_{50}$, standard error (SE), and 95% confidence intervals (CI) for reference progestins from three individual studies

| Compound | Exp. | EC50 (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 3

Estimated $IC_{50}$, standard error (SE), and 95% confident interval (CI) for the antiprogestin, RU486 from three individual studies

| Compound | Exp. | IC 50 (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly ($p<0.05$) compared to vehicle control are considered active.

Antiprogestational activity: Compounds that decrease 3 nM progesterone induced PRE-luciferase activity significantly ($p<0.05$)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

3. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium

DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium

Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture

Stock T47 D cells are maintained in growth medium. For BrdU incorporation assay, cells are plated in 96-well plates (Falcon, Becton Dickinson Labware) at 10,000 cells/well in growth medium After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 µl of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 4

Estimated EC$_{50}$, standard error (SE), and 95% confidence intervals (CI) for individual studies

| Compound | Exp | EC$_{50}$ (nM) | SE | 95% CI lower | 95% CI upper |
|---|---|---|---|---|---|
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.001 | 0.011 | 0.024 |

TABLE 5

Estimated IC$_{50}$, standard error, and 95% confident interval for the antiprogestin, RU486

| Compound | Exp. | IC$_{50}$ (nM) | SE | 95% CI lower | 95% CI upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

EC$_{50}$: Concentration of a compound that gives half-maximal increase in BrdU incorporation with SE; IC$_{50}$: Concentration of a compound that gives half-maximal decrease in 0.1 trimegestone induced BrdU incorporation with SE 4. T47D Cell Alkaline Phosphatase Assay The purpose of this assay is to identify progestins or antiprogestins by determining a compound's effect on alkaline phosphatase activity in T47D cells. The materials and methods used in this assay are as follows.

a. Culture Medium

DMEM:F12 (1:1) (GIBCO, BRL) supplemented with 5% (v/v) charcoal stripped fetal bovine serum (not heat-inactivated), 100 U/ml penicillin, 100 µg/ml streptomycin, and 2 mM GlutaMax (GIBCO, BRL).

b. Alkaline Phosphatase Assay Buffer

I. 0.1 M Tris-HCl, pH 9.8, containing 0.2% Triton X-100
II. 0.1 M Tris-HCl, pH 9.8 containing 4 mM p-nitrophenyl phosphate (Sigma).

c. Cell Culture and Treatment

Frozen T47D cells were thawed in a 37° C. water bath and diluted to 280,000 cells/ml in culture medium To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% CO$_2$/humidified atmosphere for 24 hr.

d. Alkaline Phosphatase Enzyme Assay

At the end of treatment, the medium was removed from the plate and fifty µl of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results

Analysis of dose-response data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear dose response analyses in both single dose and dose response studies.

f. Reference Compounds

Progesterone and trimegestone are reference progestins and RU486 is the reference antiprogestin. All reference compounds are run in full dose response curves and the EC$_{50}$ or IC$_{50}$ values are calculated.

TABLE 6

Estimated EC$_{50}$, standard error (SE), and 95% confidence intervals (CI) for reference progestins from three independent experiments

| Compound | Exp | EC50 (nM) | SE | 95% CI lower | 95% CI upper |
|---|---|---|---|---|---|
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 7

Estimated IC$_{50}$, standard error, and 95% confident interval for the reference antiprogestin RU486 from three independent experiments

| Compound | Exp. | IC 50 (nM) | SE | 95% CI lower | 95% CI upper |
|---|---|---|---|---|---|
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

B. In-vivo Biology

The primary in-vivo assay is the rat decidualization model which may be used to determine progestational effects of both agonists and antagonists. The secondary in-vivo assay is the rat ovulation inhibition model which is under development and hence the protocol is un-available.

1. Rat Decidualization Assay

The objective of this procedure is used to evaluate the effect of progestins and antiprogestins on rat uterine decidualization and compare the relative potencies of various test compounds. The materials and methods used in this assay are as follows.

a. Methods

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC Protocol #5002)

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg . . . ).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds

All progestin reference compounds were run in full dose-response curves and the $EC_{50}$ for uterine wet weight were calculated.

TABLE 8

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
|  | 2 | 6.21 | 1.12 | 4.41 | 8.76 |
| 3-Ketodesogestrel | 1 | 0.11 | 0.02 | 0.07 | 0.16 |
|  | 2 | 0.10 | 0.05 | 0.11 | 0.25 |
|  | 3 | 0.06 | 0.03 | 0.03 | 0.14 |
| Levonorgestrel | 1 | 0.08 | 0.03 | 0.04 | 0.16 |
|  | 2 | 0.12 | 0.02 | 0.09 | 0.17 |
|  | 3 | 0.09 | 0.02 | 0.06 | 0.13 |
|  | 4 | 0.09 | 0.02 | 0.06 | 0.14 |
| MPA | 1 | 0.42 | 0.03 | 0.29 | 0.60 |
|  | 2 | 0.39 | 0.05 | 0.22 | 0.67 |
|  | 3 | 0.39 | 0.04 | 0.25 | 0.61 |

TABLE 9

Estimated average $EC_{50}$, standard error, and 95% confidence intervals for dose-response curves of 3 reference compounds

| Compound | EC50 (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 10

Estimated $IC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: [(D-C)/C]×100%

Progestational activity: Compounds that induce decidualization significantly (p<0.05) compared to vehicle control are considered active Antiprogestational activity: Compounds that decrease $EC_{50}$ progesterone induced decidualization significantly (p<0.05)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

EXAMPLE 122

6-(3-Methoxyphenyl)spiro[4H-3,1-benzoxazin-4,1-cyclobutan]-2(1H)-one

A solution of Boc protected 4-chloroaniline (1.15 g, 5 mmol) in anhydrous THF was treated at −78° C. under a blanket of nitrogen with t-butyllithium (7.4 mL, 12.5 mmol). The reaction solution was then slowly warmed to −20° C., kept stirring for 1.5 hours, and treated with cyclobutanone (1 mL, 13.4 mmol). The mixture was warmed to rt and quenched with brine (30 mL) and 1N aqueous hydrogen chloride solution (10 mL) was added Ethyl acetate was added and the organic layer was separated and dried ($MgSO_4$). After removal of the solvent, the residue was purified by flash column chromatography (hexane:ethyl acetate/3:1) to give the alcohol which was used in next step without further purification.

To a solution of above product in ethanol was added potassium hydroxide (2 g). The reaction mixture was stirred at rt for 18 hours, followed by the addition of brine (20 mL) and a cold 1N aqueous hydrogen chloride solution (20 mL). The precipitate was collected on a filter and washed with water to afford 6-chlorospiro[4H-3,1-benzoxazine-4,1-cyclobutan]-2(1H)-one as a white solid (0.13 g, 12% for two steps): mp 183–184° C.; MS (ESI) m/z 222 [M–H]⁻.

A mixture of 6-chlorospiro[4H-3,1-benzoxazine-4,1-cyclobutan]-2(1H)-one (0.1 g, 0.45 mmol), 3-methoxyphenyl boronic acid (0.1 g, 0.66 mmol), [1,1'-bis(diphenylphosphino)ferrocene]dichloronickel (II) (50 mg, 0.073 mmol), potassium phosphate (0.35 g, 1.7 mmol) in dioxane (5 mL) was degassed to remove oxygen and then heated at 85° C. under a blanket of nitrogen for 72 hours. The reaction mixture was allowed to cool to rt. Ethyl acetate (30 mL) and brine (20 mL) were added. The organic layer was separated and dried (MgSO₄). After removal of solvent, the residue was purified using column chromatography (hexane:ethyl acetate/3:1) to yield 6-(3-methoxy-phenyl)spiro[4H-3,1-benzoxazine-4,1-cyclobutan]-2(1H)-one as white solid (18 mg, 14%): mp 145–146° C.; ¹H-NMR (DMSO-d₆) δ8.04 (s, 1H), 7.69 (d, 1H, J=1.6 Hz), 7.59 (dd, 1H, J=8.2, 1.5 Hz), 7.36 (d, 1H, J=7.9 Hz), 7.27 (d, 1H, J=7.7 Hz), 7.22 (d, 1H, J=2.2 Hz), 6.99 (d, 1H, J=8.2 Hz), 6.92 (dd, 1H, J=8.0, 2.4 Hz), 3.83 (s, 3H), 2.45–2.62(m, 4H), 1.81–2.12 (m, 2H) ); MS ((+)APCI) m/z 296 [M+H]⁺.

EXAMPLE 123

8-Bromo-6-(3-chloro-4-fluorophenyl)-4,4-dimethyl-1,4-dihydro-2H-3,1-benzoxazin-2-one To a mixture of 6-(3-chloro-4-fluorophenyl)-4,4-dimethyl-1,4-dihydro-2H-3,1-benzoxazin-2-one (0.2 g, 0.65 mmol) and sodium acetate (0.1 g, 1.2 mmol) in acetic acid (5 mL) was added, at rt under nitrogen bromine (0.04 mL, 0.78 mmol). The reaction mixture was stirred for 20 hours and poured into ice water (30 mL). The precipitate was collected on a filter and washed with water (3×5 mL) to yield 8-bromo-6-(3-chloro-4-fluorophenyl)-4,4-dimethyl-1,4-dihydro-2H-3,1-benzoxazin-2-one as off-white solid (0.18, 72%): mp 194–195° C.; ¹H-NMR (DMSO-d₆) δ9.77 (s, 1H), 8.02 (dd, 1H, J=7.10, 1.81 Hz), 7.92 (s, 1H), 7.77 (m, 1H), 7.66 (s, 1H), 7.47–7.53 (m, 1H), 1.71 (s, 6H). MS (ESI) m/z 384, 386 [M–H]⁻.

EXAMPLE 124

3-(8-Bromo-4,4-dimethyl-2-oxo-1,4-dihydro-2H-3,1-benzoxazin-6-yl)-5-fluorobenzonitrile Prepared according to the above procedure from 3-(4,4-dimethyl-2-oxo-1,4-dihydro-2H-3,1-benzoxazin-6-yl)-5-fluorobenzonitrile (0.5 g, 1.7 mmol) as an off-white solid (0.48 g, 75%): mp 216–217° C.; ¹H-NMR (DMSO-d₆) δ9.78 (s, 1H), 8.18 (t, 1H, J=1.6 Hz), 8.02–8.08 (m, 2H), 7.81 (m, 1H), 7.75 (d, 1H, J=1.8 Hz), 1.66 (s, 6H). MS (ESI) m/z 373, 375 [M–H]⁻.

EXAMPLE 125

5-(8-Bromo-4,4-dimethyl-2-oxo-1,4-dihydro-2H-3,1-benzoxazin-6-yl)-2-fluorobenzonitrile Prepared according to the above procedure from 5-(4,4-dimethyl-2-oxo-1,4-dihydro-2H-3,1-benzoxazin-6-yl)-2-fluorobenzonitrile (0.2 g, 0.67 mmol) as an off-white solid (0.18 g, 72%): mp 235–236° C.; ¹H-NMR (DMSO-d₆) δ9.78 (s, 1H), 8.38 (dd, 1H, J=6.1, 2.4 Hz), 8.14–8.20 (m, 1H), 7.98 (d, 1H, J=1.9 Hz), 7.71 (d, 1H, J=1.8 Hz), 7.62 (t, 1H, J=9.1 Hz), 1.69 (s, 6H). MS (ESI) m/z 373, 375 [M–H]⁻.

EXAMPLE 126

6-(3-Bromophenyl)-1,4,4-trimethyl-1,4-dihydro-2H-3,1-benzoxazin-2-one

To a solution of 6-(3-bromophenyl)-4,4-dimethyl-1,4-dihydro-2H-3,1-benzoxazin-2-one (1 g, 3.0 mmol) in anhydrous DMF was added, at rt under a blanket of nitrogen, sodium hydride (60% in mineral oil, 0.24 g, 6.0 mmol). After stirring for 20 minutes, the reaction solution was treated with iodomethane and stirred for 1.5 hours. The mixture was poured into a saturated aqueous ammonium sulfate solution (40 mL) and ethyl acetate (40 mL) was added. The organic layer was separated, dried (MgSO₄), and evaporated to yield 6-(3-bromophenyl)-1,4,4-trimethyl-1,4-dihydro-2H-3,1-benzoxazin-2-one as off-white solid (0.75 g, 72%): mp 142–143° C.; ¹H-NMR (DMSO-d₆) δ7.93 (s, 1H), 7.71 (m, 1H), 7.65 (s, 1H), 7.55 (d, 1H, J=8.0 Hz), 7.42 (t 1H, J=7.7 Hz), 7.18 (d, 1H, J=8.4 Hz), 3.35 (s, 3H), 1.67 (s, 6H). MS (ESI) m/z 368, 370 [M+Na]⁺.

EXAMPLE 127

6-(3-Fluorophenyl)-4-methyl-1,4-dihydro-2H-3,1-benzoxazin-2-one

4-Amino-3'-fluoro[1,1'-biphenyl]-3-carbonitrile was prepared from 3-fluorophenyl boronic acid and 2-amino-5-bromobenzonitrile according to procedure A. A solution of 4-amino-3'-fluoro[1,1'-biphenyl]-3-carbonitrile (6.65 g, 31.3 mmol) in anhydrous THF (100 mL) was treated drop wise at rt under nitrogen with methylmagnesium bromide (3.0 M in ether, 21 mL, 63 mmol). After addition, the reaction mixture was heated at gentle reflux for 1.5 hours, cooled to rt, and treated with 3N aqueous hydrogen chloride solution (30 mL). The mixture was heated at reflux for 3 hours, cooled to ambient temperature, and adjusted to pH 5–6 by addition of a saturated aqueous sodium carbonate solution. Ethyl acetate (100 mL) was added, organic layer was separated and aqueous layer was extracted with ethyl acetate (3×50 mL). The combined organic layers were dried (MgSO₄) and evaporated. The residue was purified by a silica gel column chromatography (hexane:ethyl acetate/3:1) to afford 1-(4-amino-3'-fluoro[1,1'-biphenyl]-3-yl)ethanone (3.1 g, 43%): mp 156–157° C.

A solution of 1-(4-amino-3'-fluoro[1,1'-biphenyl]-3-yl)ethanone (3 g, 13 mmol) in anhydrous methanol (60 mL) was treated at rt under nitrogen with sodium borohydride in a portion wise manner. Alter addition, the reaction mixture was stirred for 4 hours, treated with a saturated aqueous ammonium sulfate solution (50 mL) and ethyl acetate (100 mL). The organic layer was separated, dried (MgSO₄) and evaporated. The residue was purified on a silica gel column chromatography (hexane:ethyl acetate/3:1) to yield 1-(4-amino-3'-fluoro[1,1'-biphenyl]-3-yl)ethanol as a white solid (2 g, 67%): mp 136–137° C.

A mixture of above alcohol (0.2 g, 0.87 mmol) and triphosgene in anhydrous THF (20 mL) was stirred at rt under nitrogen. After 15 minutes, the mixture was treated with a saturated aqueous sodium bicarbonate solution (30 mL) and ethyl acetate (40 mL). The organic layer was separated, dried (MgSO₄), and evaporated to give 6-(3-fluorophenyl)-4-methyl-1,4-dihydro-2H-3,1-benzoxazin-2-one as a white solid (0.18 g, 81%): mp 160–161° C.; ¹H-NMR (DMSO-d₆) δ10.31 (s, 1H), 7.62 (dd, 1H, J=8.2, 1.9 Hz), 7.57 (s, 1H), 7.44–7.53 (m, 3H), 7.13–7.20 (m 1H), 6.97 (d, 1H, J=8.2 Hz), 5.57 (q, 1H, J=6.6 Hz), 1.63 (d, 3H, J=6.6 Hz). MS (ESI) m/z 256 [M–H]⁻.

EXAMPLE 128

3-(4,4-Dimethyl-8-methoxy-2-oxo-1,4-dihydro-2H-3,1-benzoxazin-6-yl)-5-fluorobenzonitrile To a solution of 2-amino-3-methoxybenzoic acid (5 g, 30 mmol) in anhydrous THF (100 mL) was added at ambient temperature under a blanket of nitrogen methylmagnesium bromide (3.0 M in THF, 50 mL, 150 mmol). The reaction mixture was heated at 50° C. for 18 hours, cooled to rt, and treated with a saturated aqueous ammonium chloride solution (50 mL). Ethyl acetate (100 mL) was added and organic layer was separated, dried ($MgSO_4$), and evaporated. The residue was dissolved in anhydrous THF (100 mL) and treated at ambient temperature under nitrogen with 1,1'-carbonyldiimidazole (5.4 g, 33 mmol). After 24 hours, the mixture was quenched with 1N aqueous hydrogen chloride solution (30 mL). Ethyl acetate (100 mL) was added, organic layer was separated, dried ($MgSO_4$), and evaporated. The residue was purified by a silica gel column chromatography (hexane:ethyl acetate/3:1) to afford 8-methoxy-4,4-dimethyl-1,4-dihydro-2H-3,1-benzoxazin-2-one as white solid (3.5 g, 56%): MS (ESI) m/z 208 [M+H]$^+$.

To a mixture of 8-methoxy-4,4-dimethyl-1,4-dihydro-2H-3,1-benzoxazin-2-one (2.1 g, 10.1 mmol), sodium acetate (1.5 g, 18 mmol) in acetic acid (30 mL) was added bromine (0.62 mL, 12 mmol) at ambient temperature. After 30 minutes, the solution was treated with a concentrated ammonium hydroxide solution (50 mL). The precipitate was collected on a filter and washed with water (3×20 mL) to yield 6-bromo-8-methoxy-4,4-dimethyl-1,4-dihydro-2H-3,1-benzoxazin-2-one (2.7 g, 93%) as off-white solid: MS (ESI) m/z 286, 288 [M+H]$^+$.

A mixture of 6-bromo-8-methoxy-4,4-dimethyl-1,4-dihydro-2H-3,1-benzoxazin-2-one (1.6 g, 5.6 mmol), bis(pinacolato)diboron (1.6 g, 6.3 mmol), potassium acetate (1.5 g, 15.3 mmol), and [1,1'-bis(diphenylphosphino)ferrocene]palladium (II) chloride (1:1 complex with methylene chloride, 0.5 g, 0.6 mmol) in DMF (30 mL) was subject to a positive flow of nitrogen to remove oxygen and then heated at 85° C. under a blanket of nitrogen for 18 hours. The reaction mixture was allowed to cool to ambient temperature, treated with 3-bromo-5-fluoro-benzonitrile (1.2 g, 6 mmol), [1,1'-bis(diphenylphosphino)-ferrocene] palladium (II) chloride (1:1 complex with methylene chloride, 0.5 g, 0.6 mmol), and sodium carbonate (2 g, 19 mmol) in water (10 mL). The resulted solution was heated at 85° C. for 3 hours under a blanket of nitrogen, cooled to rt, and treated with brine (50 mL). Ethyl acetate (100 mL) was added, organic layer was separated, dried ($MgSO_4$), and evaporated. The residue was purified by a flash silica gel column chromatography (THF:hexane/2:3) to yield 3-(4,4-dimethyl-8-methoxy-2-oxo-1,4-dihydro-2H-3,1-benzoxazin-6-yl)-5-fluorobenzonitrile as a white solid (0.6 g, 33%): mp 252–253° C.; $^1$H-NMR (DMSO-$d_6$) δ9.76 (s, 1H), 8.21 (s, 1H), 8.07 (d, 1H, J=10.6 Hz), 7.82 (m, 1H), 7.39 (s 1H), 7.36 (s, 1H), 3.93 (s, 3H), 1.66 (s, 6H). MS (ESI) m/z 325 [M–H]$^-$.

EXAMPLE 129

3-(4,4-Dimethyl-8-hydroxy-2-oxo-1,4-dihydro-2H-3,1-benzoxazin-6-yl)-5-fluorobenzonitrile A mixture of 3-(4,4-dimethyl-8-methoxy-2-oxo-1,4-dihydro-2H-3,1-benzoxazin-6-yl)-5-fluorobenzonitrile (0.1 g, 0.31 mmol), Lithium iodide (0.3 g, 2.24 mmol) in 2,4,6-collidine was heated at reflux under nitrogen for 5 hours. The solvent was removed in vacuo and the residue was taken in a mixture of brine (10 mL) and ethyl acetate (30 mL). The organic layer was separated, dried ($MgSO_4$), and evaporated. The resultant residue was purified on a silica gel column chromatography (hexane:ethyl acetate/1:1) to give the title compound as white plates (0.03 mg, 31%): mp 197–198° C.; $^1$H-NMR (DMSO-$d_6$) δ10.16 (s, 1H), 9.55 (s, 1H), 8.01 (s, 1H), 7.79–7.87 (m, 2H), 7.20 (s, 1H), 7.08 (d, 1H, J=1.0 Hz), 1.65 (s, 6H). MS (ESI) m/z 311 [M–H]$^-$.

EXAMPLE 130

6-(2,3-Difluoro-phenyl)-4,4-dimethyl-1,4-dihydro-benzo[d][1,3]oxazin-2-one

Prepared according to procedure B from (1,4-dihydro-4,4-dimethyl-2-oxo-2H-3,1-benzoxazin-6-yl)boronic acid and 2,3-difluorobenzyltriflate. A yellow solid: mp 166–167° C.; $^1$H-NMR (DMSO-$d_6$) δ10.4 (s, 1H), 7.5–7.2 (m, 5H), 7.0 (m, 1H), 1.7 (s, 6H); MS (EI) m/z 289 ([M+H]$^+$); Anal. Calc. For $C_{16}H_{13}F_2NO_2$: C, 66.43; H, 4.53; N, 4.84. Found: C, 66.15; H, 4.37; N, 4.64.

EXAMPLE 131

3-(1-Ethyl-4,4-dimethyl-2-oxo-1,4-dihydro-2H-benzo[d][1,3oxazin-6-yl)-5-fluoro-benzonitrile Prepared according to the procedure for example 125 from 3-(4,4-dimethyl-2-oxo-1,4-dihydro-2H-benzo[d][1,3]oxazin-6-yl)-5-fluoro-benzonitrile. A white solid: mp 154–155° C.; $^1$H-NMR (DMSO-$d_6$) δ8.17 (s, 1H), 8.03 (d, 1H, J=10.5 Hz), 7.84–7.77 (m, 3H), 7.27 (d, 1H, J=8.54 Hz), 3.97 (q, 2H, J=6.89 Hz), 1.67 (s, 6H) 1.21 (t, 3H, J=6.95 Hz); MS (EI) m/z 324 ([M+H]$^+$); Anal. Calc. For $C_{19}H_{17}FN_2O_2$: C, 70.36; H, 5.28; N, 8.64. Found: C, 70.33; H, 5.51; N, 8.48.

EXAMPLE 132

[6-(4,4-dimethyl-2-oxo-1,4-dihydro-2H-3,1-benzoxazin-6-yl)pyridin-2yl]acetonitrile Prepared according to procedure B from (1,4-dihydro-4,4-dimethyl-2-oxo-2H-3,1-benzoxazin-6-yl)boronic acid and (6-bromo-2-pyridyl)acetonitrile (J. Org. Chem. 1988, 53, 786–790). An off-white solid, mp 210–212.5° C. $^1$H NMR (DMSO-$d_6$) δ1.68 (s, 6H), 4.27 (s, 2H), 7.00 (d, 1H, J=8.3 Hz), 7.34 (d, 1H, J=7.1 Hz), 7.89–7.96 (m, 2H), 8.00–8.05 (m, 2H), 10.42 (s, 1H). MS (ESI) [M–H]$^-$=292. Anal. calcd. for $C_{17}H_{15}N_3O_2$: C, 69.61; H, 5.15; N, 14.33. Found: C, 68.49; H, 5.19; N, 13.74.

EXAMPLE 133

3-(4,4-Dimethyl-2-oxo-1,4-dihydro-2H-benzo[d]1,3]-oxazin-6-yl)-5-fluoro-phenylacetonitrile To a solution of 3-bromo-5-fluorobenzaldehyde(22.25 g, 0.11 mole) in methanol at rt was added $NaBH_4$, (2.07 g, 0.055 mole) stirred at rt for 2 hr. The reaction was quenched with $H_2O$, and concentrated. The residue was diluted with diethyl ether, washed with 1 N HCl, brine, dried over $MgSO_4$, concentrated. 3-Bromo-5-fluorobenzyl alcohol as a colorless oil was collected (14.6 g, 65%). $^1$H NMR(DMSO-$d_6$) δ4.50 (m, 2H), 5.44 (t, 3H, J=5.93 Hz), 7.16 (dd, 1H, J=1.09, 8.79 Hz), 7.36 (s, 1H), 7.38 (dd, 1H, J=2.99, 6.15 Hz); Anal. Calc. For $C_7H_6Br_2FO$: C, 41.01; H, 2.95. Found: C, 41.30; H, 3.01.

To a solution of 3-Bromo-5-fluorobenzyl alcohol (2.3 g, 0.011 mole) in $CH_2Cl_2$ (15 mL) was added 12.4 mL of 1.0

M PBr₃ (3.33 g, 0.0123 mole) in CH₂Cl₂, stirred for 3 hr, diluted with ether (100 mL), washed with H₂O (50 mL, 3×), dried over MgSO₄, concentrated, and purified by column chromatography using 1:9 ethyl acetate/hexane as an eluant solvent system. 3-Bromo-5-fluorobenzyl bromide as a white crystalline material was obtained, mp 41–43° C. ¹H NMR (DMSO-d₆) δ4.69 (s, 2H), 7.52 (d, 1H, J=1.76 Hz) 7.54 (d, 1H, J=1.91 Hz), 7.56 (s, 1H); MS(EI): M+. m/z 266; Anal. Calc. For C₇H₅Br₂F: C, 31.38; H, 1.88. Found: C, 31.75; H, 1.78.

To a solution of 3-bromo-5-fluorobenzyl bromide (3.2 g, 0.0112 mole) in 1,4-dioxane (20 mL) was added a solution of KCN (0.82 g, 0.013 mole) in H₂O (5 mL) and EtOH (5 mL), refluxed for 2 hours, and extracted with ether, washed with brine, dried over MgSO₄, and concentrated. Column chromatography was performed using hexane/ethyl acetate (19:1). 3-Bromo-5-fluorophenylacetonitrile was obtained was a colorless oil: ¹H NMR (DMSO-d₆) δ4.15 (s, 2H), 7.29 (d, 1H, J=9.37 Hz), 7.47 (s, 1H), 7.55 (d, 1H, J=8.45 Hz); MS(EI) M+m/z 213; Anal. Calc. For C₈H₅BrFN: C, 44.89; H, 2.35; N, 6.54. Found: C, 44.88; H, 2.32; N, 6.46.

The title compound was prepared according to the procedure B from 3-bromo-5-fluorophenylacetonitrile and (1,4-dihydro-4,4-dimethyl-2-oxo-2H-3,1-benzoxazin-6-yl)boronic acid. A white solid was obtained and recrystallized from ethanol/ether: mp 218–220. ¹H NMR (DMSO-d₆) δ1.67 (s, 6H), 4.11(s, 2H), 6.98 (d, 1H, J=8.92 Hz), 7.18 (d, 1H, J=9.26 Hz), 7.52–7.62 (m, 3H), 10.37 (s, 1H); MS(EI) (M–H)⁻ m/z 309; Anal. Calcd. For C₁₈H₁₅FN₂O₂: C, 69.67; H, 4.87; N, 9.03. Found: C, 69.78; H, 4.97; N, 8.36.

EXAMPLE 134

3-(4,4-Dimethyl-2-oxo-1,4-dihydro-2H-benzo[d][1,3]-oxazin-6-yl)-4-fluoro-phenylacetonitrile To a solution of 5-bromo-2-fluorotoluene (15 g, 0.079 mole) in CCl₄ (150 mL) was added NBS (14.2 g, 0.080 mole). The resulting reaction solution was heated under reflux with the starting material being completely consumed within 2 hr. CCl₄ was removed under reduced pressure and the residue was diluted, dissolved in ether, washed with brine (3×), dried over MgSO₄, and concentrated. Chromatography using hexane yielded 5-bromo-2-fluorobenzyl bromide. The product was immediately used for the reaction below.

5-Bromo-2-fluorobenzyl bromide (8.0 g, 0.03 mole) was dissolved in 1,4-Dioxane (60 mL) and added to a solution of KCN (2.04 g, 0.031 mole) in H₂O (20 mL) and ethanol (20 mL). The resulting mixture was heated under reflux for 5 h. After cooling to rt, the product was extracted with ether (200 mL), washed with brine, dried over MgSO₄, concentrated. Crystallized from ether/hexane to give 5-bromo-2-fluorophenylacetonitrile as a white crystalline material (5.6 g, 88%): mp 55–58° C.; ¹H NMR (DMSO-d₆) δ4.07 (s, 2H), 7.29 (t, 1H, J=9.23 Hz), 7.60–7.69 (m, 2H); MS (EI) M+. m/z 213; Anal. Calc. For C₈H₅Br₂FN: C, 44.89; H, 2.35; N, 6.54. Found: C, 44.90; H, 2.24; N, 6.43.

The title compound was prepared from 5-Bromo-2-fluorophenylacetonitrile and (1,4-dihydro-4,4-dimethyl-2-oxo-2H-3,1-benzoxaxin-6-yl)boronic acid. White solid; mp 184–187° C.; ¹H NMR (DMSO-d₆) δ1.67 (s, 6H), 4.11 (s, 2H), 6.98 (d, 1H, J=8.92 Hz), 7.36 (t, 1H, J=9.13 Hz) 7.54 (d, 2H, J=7.91 Hz), 7.67–7.75 (m, 2H), 10.37 (s, 1H); MS(EI) (M–H)⁻ m/z 309; Anal. Calc. For C₁₈H₁₅FN₂O₂: C, 69.67; H, 4.87; N, 9.03. Found: C, 68.71; H, 4.80; N, 8.54.

EXAMPLE 135

4-(4,4-Dimethyl-2-oxo-1,4-dihydro-2H-benzo[d][1,3]oxazin-6-yl)-2-fluorophenylacetonitrile Prepared according to procedure B from 4-bromo-2-fluorophenylacetonitrile (T. Alessi A. H. P. U.S. Pat. No. 4,895,862) and (1,4-dihydro-4,4-dimethyl-2-oxo-2H-3,1-benzoxazin-6-yl)boronic acid. A grey solid; mp 253–256° C. ¹H-NMR(DMSO-d₆) δ10.35 (s, 1H) 7.67–7.49 (m, 5H), 6.97 (d, 1H; J=8.6 Hz) 4.09 (s, 2H) 1.67 (s, 6H); MS [M–H]⁻ m/z 309. Anal. Calc. For C₁₈H₁₅N₂FO₂.0.15H₂O: C, 69.07; H, 4.93; N, 8.95. Found C, 69.27; H, 5.05; N, 8.50

EXAMPLE 136

2-(4,4-Dimethyl 2-oxo-1,4-dihydro-2H-benzo[d][1,3]-oxazin-6-yl)phenylacetonitrile Prepared according to procedure B from 2-bromophenylacetonitrile and (1,4-dihydro-4,4-dimethyl-2-oxo-2H-3,1-benzoxazin-6-yl)boronic acid. White solid; mp 176–179° C.; ¹H-NMR(DMSO-d₆), δ10.31 (s, 1H), 7.53 (m, 1H), 7.48 (m, 2H), 7.22–7.32 (m, 3H), 6.98 (d, 1H, J=8.0 Hz), 3.90 (s, 2H), 1.64 (s, 6H). MS (+)APCI [M+H]⁺ m/z=293. Anal. Calc. For C₁₈H₁₆N₂O₂: C, 73.95; H, 5.52, N, 9.58. Found: C, 73.51; H, 5.70; N, 9.39.

EXAMPLE 137

N-[4-(4,4-Dimethyl-2-oxo-1,4-dihydro-2H-3,1-benzoxazin-6-yl)-2-fluoro-phenyl]-acetamide Prepared according to procedure B from 4'-bromo-2'-fluoroacetanilide and (1,4-dihydro-4,4-dimethyl-2-oxo-2H-3,1-benzoxazin-6-yl)boronic acid. Off white solid; mp 245–247° C. ¹H-NMR (DMSO-d₆), δ10.3 (s, 1H), 9.79 (s, 1H), 7.95 (t, 1H, J=8.4 Hz), 7.56–7.63 (m, 3H), 7.47 (dd, 1H, J=1.64, 8.47 Hz), 6.95 (d, 1H, J=8.9 Hz), 2.1(s, 3H), 1.67 (s, 6H); MS+APCI [M+H]⁺ m/z 329. Anal. Calc. For C₁₈H₁₇N₂FO₃: C, 65.85; H, 5.22; N, 8.53. Found: C, 65.46; H, 5.24; N, 8.12.

EXAMPLE 138

6-(3-Fluoro-4-methoxy-phenyl)4,4-dimethyl-1,4-dihydro-benzo[d][1,3]oxazin-2-one Prepared according to procedure B from 4-bromo-2-fluoroanisole and (1,4-dihydro-4,4-dimethyl-2-oxo-2H-3,1-benzoxazin-6-yl)boronic acid. White solid: mp 210–211° C. ¹H-NMR (DMSO-d₆), δ10.27 (s,1H), 7.52–7.60 (m, 3H), 7.45(d, 1H, J=8.6 Hz), 7.22 (t, 1H, J=8.9 Hz), 6.94 (d, 1H, J=8.8 Hz), 3.87 (s, 3H), 1.66 (s, 6H). MS [M–H]⁻ m/z=300. Anal. Calc. For C₁₇H16FNO₃: C, 67.76; H, 5.35; N, 4.65. Found: C, 67.88; H, 5.39; N, 4.70.

EXAMPLE 139

3-(4,4-Dimethyl-2-oxo-1,4-dihydro-2H-benzo[d][1,3]-oxazin-6-yl)phenylacetonitrile Prepared according to the procedure B from 3-bromophenylacetonitrile and (1,4-dihydro-4,4-dimethyl-2-oxo-2H-3,1-benzoxazin-6-yl)boronic acid. White solid: mp 188–190° C. ¹H-NMR (DMSO-d₆) δ10.33 (s, 1H), 7.62 (m, 2H), 7.55 (m, 2H), 7.48 (d, 1H, J=8.00 Hz), 7.33 (d, 1H, J=7.57 Hz), 6.99 (d, 1H, J=8.81 Hz) 4.09 (s, 2H), 1.67 (s, 6H); MS m/z 291(M–H). Anal. Calc. For (C₁₈H₁₆N₂O₂)₂.0.3 H₂O: C, 72.61; H, 5.62; N, 9.41. Found: C, 73.00; H, 5.43; N, 8.81

EXAMPLE 140

3-(4,4-Dimethyl-2-oxo-1,4-dihydro-2H-benzo[d][1,3]-oxazin-6-yl)benzenesulfonamide Prepared according to procedure B from 3-bromobenzenesulfonamide and (1,4-dihydro-4,4- dimethyl-2-oxo-2H-3,1-benzoxazin-6-yl)boronic acid. White solid: mp 242–244° C. (dec) ¹H-NMR (DMSO-d₆) δ10.28 (s, broad 1H), 8.07 (s, 1H), 7.9 (d, 1H, J=7.80 Hz), 7.78 (d, 1H, J=7.86 Hz), 7.64 (t, 1H, J=7.79 Hz), 7,59 (m, 2H), 7.42 s, broad 2H), 7.02 (d, 1H, J=8.86 Hz), 1.68 (s, 6H); MS m/z 331(M+H). Anal. Calc. For $C_{16}H_{16}N_2O_4S$: C, 57.82; H, 4.85; N, 8.43. Found: C, 57.49; H, 5.08; N, 8.05.

EXAMPLE 141

(4,4-Dimethyl-2-oxo-1,4-dihydro-2H-benzo[d][1,3]-oxazin-6-yl)-thiophene-2-sulfonamide Prepared according to procedure B from 5-bromothiophene-2-sulphonamide and (1,4-dihydro-4,4-dimethyl-2-oxo-2H-3,1-benzoxazin-6-yl)boronic acid. White solid: mp 258–260° C., ¹H-NMR (DMSO-d₆) δ10.41 (s, 1H), 7.71 (s, 2H), 7.58 (m, 2H), 7.52 (d, 1H, J=3.9 Hz), 7.48 (d, 1H J=8.16 Hz), 6.95(d, 1H J=8.16), 1.66 (s, 6H); MS m/z 337 (M–H). Anal. Calc. For $C_{14}H_{14}N_2O_4S_2$: C, 49.69; H, 4.17; N, 8.28. Found: C, 49.90; H, 4.28; N, 8.12.

EXAMPLE 142

6-(6-Amino-pyridin-3-yl)-4,4-dimethyl-1,4-dihydro-benzo[d][1,3]oxazine-2-one

Prepared according to procedure B from 2-amino-5-bromopyridine and (1,4-dihydro-4,4-dimethyl-2-oxo-2H-3,1-benzoxazin-6-yl)boronic acid. White crystals, mp 257–259° C. ¹H-NMR (DMSO-d₆) δ10.20 (s, 1H), 8.22 (d, 1H, J=2.38 Hz) 7.69, 7.66 (dd, 1H, J=2.5, 2.5 Hz), 7.42 (m, 2H), 6.89 (d, 1H, J=8.8 Hz), 6.49(d, 1H, J=8.64 Hz), 6.02 (s, 2H), 1.64 (s, 6H); MS m/z 269 M⁺. Anal. Calcd. For $C_{15}H_5N_3O_2.17H_2O$: C, 66.15; H, 5.68; N, 15.43. Found: C, 66.10; H, 5.81; N, 15.02.

EXAMPLE 143

6-(5-Diethoxymethyl-furan-3-yl)-4,4-dimethyl-1,4-dihydro-benzo[d][1,3]oxazin-2-one Prepared according to procedure B from 4,4-dimethyl 2 oxo -1,4-dihydro 2H-benzo [d][1,3]oxazine-6-boronic acid and 3-bromo-5-diethoxymeyhyl furan. A brown gum: ¹H NMR (DMSO-d₆) δ10.2 (s, 1H), 8.12(s, 1H), 7.54–7.49 (m, 2H), 6.93–6.88 (m, 2H), 5.56 (s, 1H), 3.60–3.38 (m, 4H), 1.67 (s, 6H), 1.2–1.14 (m, 6H). .MS (ESI) m/z 344 [M–H]⁻. Anal. Calcd. For $C_{19}H_{23}NO_5$ 1/2H₂O: C, 64.39; H, 6.77; N, 3.95. Found C, 64.90; H, 6.79; N, 3.78.

EXAMPLE 144

4-(4,4-Dimethyl-2-oxo-1,4-dihydro-2H-benzo[d][1,3]oxazin-6-yl)-furan-2-carbaldehyde A solution of 6-(5-diethoxymethyl-furan-3-yl)-4,4-dimethyl-1,4-dihydro-benzo[d][1,3]oxazin-2-one (1.1 g, 3 mmol) was stirred in THF (20 mL) and 2N HCl (2 mL) for 1 hour. The crystalline product was filtered and dried (0.52 g, 69%): mp 262–263° C.; ¹H NMR (DMSO-d₆) δ10.3 (s, 1H), 9.65 (s, 1H), 8.59 (s, 1H), 8.04 (s, 1H), 7.65–7.64 (d, 1H, J=1.5 Hz), 7.61–7.60 (d, 1H, J=1.8 Hz), 7.59–7.58 (d, 1H, J=1.8 Hz), 6.94–6.91 (d, 1H, J=8.2 Hz), 1.65 (s, 6H). MS (ESI) m/z 270 [M–H]⁻.

EXAMPLE 145

4-(1,4-Dihydro-4,4-dimethyl-2-oxo-2H-3,1-benzoxazin-6-yl)-2-furancarboxaldehyde oxime A mixture of 4-(4,4-dimethyl-2-oxo-1,4-dihydro-2H-benzo[d][1,3]oxazin-6-yl)-furan-2-carbaldehyde (2.7 g, 10 mmol), hydroxylamine hydrochloride (0.75 g, 10.6 mmol) and sodium acetate (0.87 g, 10.6 mmol) was heated at reflux in 80% ethanol (25 mL) for 2 hours. The title compound crystallized from the cooled reaction mixture as tan crystals (1.5 g, 52.4%): mp 236–238° C. ¹H NMR (DMSO-d₆) δ11.97 (s, 1H), 10.26 (s, 1H), 8.2 (s, 1H), 7.63 (s, 1H), 7.56–7.52 (m, 3H), 6.91–6.88 (d, 1H, J=8.1 Hz), 1.66 (s, 6H). MS ESI m/z 285 [M–H]⁻. Anal. Calcd. For $C_{15}H_{14}N_2$; $O_4$: C, 62.93; H, 4.93; N, 9.79. Found C, 62.77; H, 5.00; N, 9.79.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of contraception which comprises administering to a female of child bearing age over a period of 28 consecutive days:

a) a first phase of from 18 to 21 daily dosage units containing a progestational agent at a daily dose equal in progestational activity to from about 35 to about 150 µg levonorgestrel and ethinyl estradiol at a daily dose range of from about 10 to about 35 µg;

b) a second phase of from 1 to 7 daily dosage units, each daily dosage unit containing an antiprogestin of the formula:

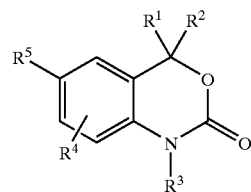

I wherein:

$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$;

or $R^1$ and $R^2$ are fused to form:

(i) a carbon-based 3 to 8 membered saturated spirocyclic ring;

(ii) a carbon-based 3 to 8 membered spirocyclic ring having in its backbone one or more carbon-carbon double bonds; or (iii) a 3 to 8 membered heterocyclic ring having in its backbone one to three heteroatoms selected from the group consisting of O, S and N;

the spirocyclic rings of (i), (ii) and (iii) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl)₂;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is H, halogen, CN, $NO_2$, $C_1$ to $C_6$ alkyl, substituted $C_1$ to $C_6$ alkyl, alkynyl, substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is (iv), (v), (vi), or (vii)

(iv) a substituted benzene ring having the substituents X, Y and Z:

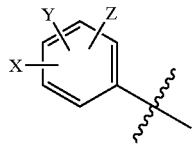

wherein:

X is selected from the group consisting of halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy;

(v) a five membered ring having in its backbone 1, 2, or 3 heteroatoms selected from the group consisting of O, S, SO, and $SO_2$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^G COR^F$;

(vi) a five membered ring having in its backbone 1, 2, or 3 $NR^6$ heteroatoms and having one or two independent substituents selected from the group consisting of H, halogen, $NO_2$, amino, $C_1$ to $C_3$ alkyl, $C_1$ to $C_3$ alkoxy, $C_1$ to $C_3$ aminoalkyl, $COR^F$, and $NR^G COR^F$; or (vii) a six membered ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^G COR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^6$ is H or $C_1$ to $C_3$ alkyl;

or pharmaceutically acceptable salt thereof;

at a concentration of from 2 to 50 mg and ethinyl estradiol at a concentration of from about 10 to about 35 μg; and c) optionally, a third phase of daily dosage units of an orally and pharmaceutically acceptable placebo, the total of the daily dosage units being 28.

2. The method according to claim 1, wherein the progestational agent is levonorgestrel and wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is (viii), (ix), (x) or (xi):

(viii) the substituted benzene ring (iv), wherein:

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring containing in its backbone 1 to 3 heteroatoms, $COR^D$, $OCOR^D$, and $NR^E COR^D$;

Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy;

(ix) the five membered ring (v) containing one or two independent substituents selected from the group consisting of H, halogen, CN, $NO_2$, amino, $C_1$ to $C_3$ alkyl, and $C_1$ to $C_3$ alkoxy;

(x) the five membered ring (vi) containing one or two independent substituents selected from the group consisting of H, halogen, $NO_2$, amino, $C_1$ to $C_3$ alkyl, and $C_1$ to $C_3$ alkoxy; or (xi) the six membered ring (vii) containing one or two independent substituents selected from the group consisting of H, halogen, CN, $NO_2$, amino, $C_1$ to $C_3$ alkyl, and $C_1$ to $C_3$ alkoxy.

3. The method according to claim 1, wherein the progestational agent is levonorgestrel and wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is (xii), (xiii), (xiv) or (xv):

(xii) the substituted benzene ring (iv), wherein:

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring having in its backbone 1 to 3 heteroatoms, $COR^D$, $OCOR^D$, and $NR^ECOR^D$;

Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy;

(xiii) the five membered ring (v) containing one or two independent substituents selected from the group consisting of H, halogen, CN, $NO_2$, amino, $C_1$ to $C_3$ alkyl, and $C_1$ to $C_3$ alkoxy;

(xiv) the five membered ring (vi) containing one or two independent substituents selected from the group consisting of H, halogen, $NO_2$, amino, $C_1$ to $C_3$ alkyl, and $C_1$ to $C_3$ alkoxy; or (xv) the six membered ring (vii) containing one or two independent substituents selected from the group consisting of H, halogen, CN, $NO_2$, amino, $C_1$ to $C_3$ alkyl, and $C_1$ to $C_3$ alkoxy.

4. The method according to claim 1, wherein the progestational agent is levonorgestrel and wherein:

$R^1 = R^2$ and are selected from the group consisting of $C_1$ to $C_3$ alkyl and substituted $C_1$ to $C_3$ alkyl;

or $R^1$ and $R^2$ are fused to form the carbon-based 3 to 6 membered saturated spirocyclic ring;

$R^3$ is H, OH, $NH_2$, $C_1$ to $C_6$ alkyl, substituted $C_1$ to $C_6$ alkyl, or $COR^C$;

$R^C$ is H, $C_1$ to $C_3$ alkyl, or $C_1$ to $C_3$ alkoxy;

$R^4$ is H, halogen, CN, $NO_2$, $C_1$ to $C_3$ alkyl, substituted $C_1$ to $C_3$ alkyl, $C_1$ to $C_3$ alkoxy, or substituted $C_1$ to $C_3$ alkoxy;

$R^5$ is (xvi), (xvii), (xviii), or (xix):

(xvi) the substituted benzene ring (iv) of the structure:

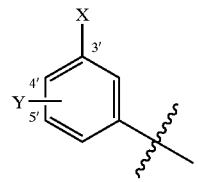

wherein:

X is halogen, CN, $C_1$ to $C_3$ alkoxy, $C_1$ to $C_3$ alkyl, $NO_2$, $C_1$ to $C_3$ perfluoroalkyl, 5 membered heterocyclic ring containing in its backbone 1 to 3 heteroatoms, or $C_1$ to $C_3$ thioalkoxy;

Y is H, halogen, CN, $NO_2$, $C_1$ to $C_3$ alkoxy, $C_1$ to $C_3$ alkyl, or $C_1$ to $C_3$ thioalkoxy;

(xvii) the five membered ring (v) of the structure:

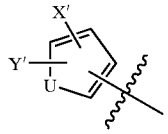

wherein:

U is O or S;

X' is selected from the group consisting of halogen, CN, $NO_2$, $C_1$ to $C_3$ alkyl and $C_1$ to $C_3$ alkoxy;

Y' is selected from the group consisting of H and $C_1$ to $C_3$ alkyl;

(xviii) the five membered ring (vi) of the structure:

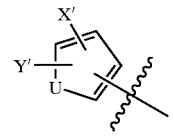

wherein:

U is $NR^6$;

X' is selected from the group consisting of halogen, $NO_2$, $C_1$ to $C_3$ alkyl and $C_1$ to $C_3$ alkoxy;

Y' is selected from the group consisting of H and $C_1$ to $C_3$ alkyl; or (xix) the six membered ring (vii) of the structure:

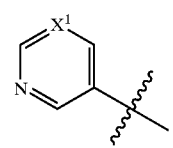

wherein:

$X^1$ is N or $CX^2$;

$X^2$ is halogen, CN, $C_1$ to $C_3$ alkoxy, or $NO_2$.

5. The method according to claim 1, wherein the progestational agent is levonorgestrel and wherein:

$R^1$ and $R^2$ are $CH_3$ or $R^1$ and $R^2$ are fused to form the carbon-based 6 membered saturated spirocyclic ring $R^3$ is H, OH, $NH_2$, $CH_3$, substituted $CH_3$, or $COR^A$;

$R^A$ is H, $C_1$ to $C_3$ alkyl, or $C_1$ to $C_3$ alkoxy;

$R^4$ is H, halogen, $NO_2$, CN, or $C_1$ to $C_3$ alkyl;

$R^5$ is the substituted benzene ring (iv) of the structure:

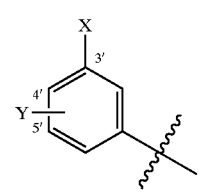

wherein:

X is selected from the group consisting of halogen, CN, methoxy, $NO_2$, or 5-membered heterocyclic ring;

wherein said 5-membered heterocyclic ring is 2-thiazole;

Y is H or halogen;

wherein said halogen is F.

6. The method according to claim 1, wherein the progestational agent is levonorgestrel and wherein:

$R^1$ and $R^2$ are $CH_3$ or $R^1$ and $R^2$ are fused to form the carbon-based 6 membered saturated spirocyclic ring;

$R^3$ is H, OH, $NH_2$, $CH_3$, substituted $CH_3$, or $COR^A$;

$R^A$ is H, $C_1$ to $C_3$ alkyl, or $C_1$ to $C_3$ alkoxy;

$R^4$ is H, halogen, $NO_2$, CN, or $C_1$ to $C_3$ alkyl;

$R^5$ is the five membered ring (v) or (vi) having the structure:

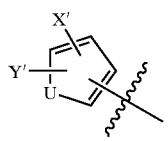

wherein:
U is O, S, or NH;
X' is halogen, CN, or NO$_2$, provided that when U is NH, X is not CN;
Y' is H or C$_1$ to C$_3$ alkyl.

7. The method according to claim 1, wherein the antiprogestin compound is selected from the group consisting of:

a) 6-(3-Chlorophenyl)-4,4-dimethyl-1,4-dihydrobenzo[d][1,3]oxazin-2-one;
b) 6-(3-Methoxy-phenyl)-4,4-dimethyl-1,4-dihydro-benzo[d][1,3]-oxazin-2-one;
c) 6-(2-Chloro-phenyl)-4,4-dimethyl-1,4-dihydro-benzo[d][1,3]oxazin-2-one;
d) 6-(4-Chloro-phenyl)-4,4-dimethyl-1,4-dihydro-benzo[d][1,3]-oxazin-2-one;
e) 6-(3-Chloro-phenyl)-4-methyl-1,4-dihydro-benzo[d][1,3]oxazin-2-one;
f) 6-(3-Chloro-phenyl)-4-ethyl-1,4-dihydro-benzo[d][1,3]oxazin-2-one; and
g) 6-(3-Chloro-phenyl)-4-phenyl-1,4-dihydro-benzo[d][1,3]oxazin-2-one;

or a pharmaceutically acceptable salt thereof.

8. The method according to claim 1, wherein the antiprogestin compound is selected from the group consisting of:

a) 3-(4,4-Dimethyl-2-oxo-1,4-dihydro-2H-benzo[d][1,3]oxazin-6-yl)-benzonitrile;
b) 4,4-Dimethyl-6-(3-nitrophenyl)-1,4-dihydrobenzo[d][1,3]oxazin-2-one;
c) 6-(3-Bromo-5-fluorophenyl)-4,4-dimethyl-1,4-dihydrobenzo[d][1,3]oxazin-2-one;
d) 3-(4,4-Dimethyl-2-oxo-1,4-dihydro-2H-benzo[d][1,3]oxazin-6-yl)-5-fluorobenzonitrile;
e) 5-(4,4-Dimethyl-2-oxo-1,4-dihydro-2H-benzo[d][1,3]oxazin-6-yl)-nicotinonitrile;
f) 4-(4,4-Dimethyl-2-oxo-1,4-dihydro-2H-benzo[d][1,3]oxazin-6-yl)-thiophene-2-carbonitrile;
g) 5-(4,4-Dimethyl-2-oxo-1,4-dihydro-2H-benzo[d][1,3]oxazin-6-yl)-thiophene-2-carbonitrile;
h) 5-(4,4-Dimethyl-2-oxo-1,4-dihydro-2H-benzo[d][1,3]oxazin-6-yl)-4-methyl-thiophene-2-carbonitrile;
i) 4-(4,4-Dimethyl-2-oxo-1,4-dihydro-2H-benzo[d][1,3]oxazin-6-yl)-furan-2-carbonitrile; and
j) 4,4-Diethyl-6-(3-nitrophenyl)-1,4-dihydrobenzo[d][1,3]oxazin-2-one;

or a pharmaceutically acceptable salt thereof.

9. The method according to claim 1, wherein the antiprogestin compound is selected from the group consisting of:

a) 6-(3-Chlorophenyl)-4,4-diethyl-1,4-dihydrobenzo[d][1,3]oxazin-2-one;
b) 6-(3-Chlorophenyl)-spiro[4H-3,1-benzoxazine-4,1'-cyclohexane]-2-(1H)-one;
c) 6-(3-Chlorophenyl)-spiro-[4H-3,1-benzoxazine-4,1'-cyclopentane]-2(1H)-one;
d) 6-(3-Nitrophenyl)-spiro[4H-3,1-benzoxazine-4,1'-cyclohexan]-2(1H)-one;
e) 4-Allyl-6-(3-chlorophenyl)-4-methyl-1,4-dihydro-benzo[d][1,3]oxazin-2-one;
f) 6-(3-Chlorophenyl)-4-methyl-4propyn-1-yl-1,4-dihydro-benzo[d][1,3]oxazin-2-one; and
g) 6-(3-Chlorophenyl)-4-ethynyl-4-methyl-1,4-dihydro-benzo[d][1,3]oxazin-2-one;

or a pharmaceutically acceptable salt thereof.

10. The method according to claim 1, wherein the antiprogestin compound is selected from the group consisting of:

a) 6-(3-Chlorophenyl)-4-methyl-4-phenyl-1,4-dihydrobenzo[d][1,3]oxazin-2-one;
b) 4-Benzyl-6-(3-chloro-phenyl)-4-methyl-1,4-dihydro-benzo[d][1,3]oxazin-2-one;
c) 6-(3-Chloro-phenyl)-4-cyclopropyl-4-methyl-1,4-dihydro-benzo[d][1,3]oxazin-2-one;
d) 6-(3-Chloro-phenyl)-4-cyclopropyl-4-propyn-1-yl-1,4-dihydro-benzo[d][1,3]oxazin-2-one;
e) 6-(3-Chloro-phenyl)-4,4-dicyclopropyl-1,4-dihydro-benzo[d][1,3]oxazin-2-one;
f) 6-(3-Chloro-phenyl)-4,4-dipropyn-1-yl-1,4-dihydrobenzo[d][1,3]oxazin-2-one;
g) 6-(3-Bromo-5-fluorophenyl)-1,4,4-trimethyl-1,4-dihydrobenzo[d][1,3]oxazin-2-one;
h) 6-Chloro-4-methyl-4-trifluoromethyl-1,4-dihydro-benzo[d][1,3]oxazin-2-one; and
i) 6-(3-Methoxyphenyl)-4-methyl-4-trifluoromethyl-1,4-dihydro-benzo[d][1,3]oxazin-2-one;

or a pharmaceutically acceptable salt thereof.

11. The method according to claim 1, wherein the antiprogestin compound is selected from the group consisting of:

a) 6-(3-Acetyl-phenyl)-4,4-dimethyl-1,4-dihydro-benzo[d][1,3]-oxazin-2-one;
b) 6-(3-Acetyl-phenyl)-4,4-dimethyl-1,4-dihydro-benzo[d][1,3]-oxazin-2-one;
c) 6-(3-Benzoyl-phenyl)-4,4-dimethyl-1,4-dihydro-benzo[d][1,3]-oxazin-2-one;
d) 4,4-Dimethyl-6-[3-(1H-tetrazol-5-yl)-phenyl]-1,4-dihydrobenzo[d][1,3]oxazin-2-one;
e) 4-(4,4-Dicyclopropyl-2-oxo-1,4-dihydro-2H-benzo[d][1,3]oxazin-6-yl)-thiophene-2-carbonitrile;
f) 6-(3-Bromo-5-fluoro-phenyl)-4,4-dicyclopropyl-1,4-dihydrobenzo-[d][1,3]oxazin-2-one;
g) 3-(4,4-Dicyclopropyl-2-oxo-1,4-dihydro-2H-benzo[d][1,3]oxazin-6-yl)-5-fluoro-benzonitrile;
h) 6-(3-Bromo-5-methyl-phenyl)-4,4-dimethyl-1,4-dihydrobenzo-[d][1,3]oxazin-2-one;
i) 6-(3-Bromo-5-trifluoromethoxy-phenyl)-4,4-dimethyl-1,4-dihydrobenzo[d][1,3]-oxazin-2-one; and
j) 3-(4,4-Dimethyl-2-oxo-1,4-dihydro-2H-benzo[d][1,3]oxazin-6-yl)-5-methyl-benzonitrile;

or a pharmaceutically acceptable salt thereof.

12. The method according to claim 1, wherein the antiprogestin compound is selected from the group consisting of:

a) 3-(4,4-Dimethyl-2-oxo-1,4-dihydro-2H-benzo[d][1,3]oxazin-6-yl)-5-trifluoromethoxy-benzonitrile;
b) 6-(3,5-difluoro-phenyl)-4,4-dimethyl-1,4-dihydrobenzo-[d][1,3]oxazin-2-one;
c) 6-(3,5-dichloro-phenyl)-4,4-dimethyl-1,4-dihydrobenzo-[d][1,3]oxazin-2-one;

d) 6-(3,5-Bis-trifluoromethyl-phenyl)-4,4-dimethyl-1,4-dihydrobenzo[d][1,3]oxazin-2-one;
e) 3-(4,4-Dimethyl-2-oxo-1,4-dihydro-2H-benzo[d][1,3]oxazin-6-yl)-5-methoxy-benzonitrile;
f) 6-(3-Fluoro-phenyl)-4,4-dimethyl-1,4-dihydro-benzo[d][1,3]-oxazin-2-one;
g) 6-(3-Chloro-4-fluoro-phenyl)-4,4-dimethyl-1,4-dihydro-benzo[d][1,3]oxazin-2-one;
h) 3-(1-Diethoxymethyl-4,4-dimethyl-2-oxo-1,4-dihydro-2H-benzo[d][1,3]oxazin-6-yl)-5-fluoro-benzonitrile; and
i) 3-Fluoro-5-(1-methoxymethyl-4,4-dimethyl-2-oxo-1,4-dihydro-2H-benzo[d][1,3]oxazin-6-yl)-benzonitrile;

or a pharmaceutically acceptable salt thereof.

13. The method according to claim 1, wherein the anti-progestin compound is selected from the group consisting of:
a) Phosphoric acid 6-(3-cyano-5-fluoro-phenyl)-4,4-dimethyl-4H-benzo[d][1,3]oxazin-2-yl ester diethyl ether;
b) 3-(4,4-Dimethyl-2-oxo-1,4-dihydro-2H-benzo[d][1,3]oxazin-6-yl)-4-fluoro-benzonitrile;
c) 6-(3-Chloro-4-fluoro-phenyl)-8-fluoro-4,4-dimethyl-1,4-dihydrobenzo[d][1,3]-oxazin-2-one;
d) 6-(3-Bromo-phenyl)-4,4-dimethyl-1,4-dihydro-benzo[d][1,3]-oxazin-2-one;
e) 4,4-Dimethyl-6-(3-trimethylsilanylethynyl-phenyl)-1,4-dihydro-benzo[d][1,3]oxazin-2-one;
f) 6-(3-Ethynyl-phenyl)-4,4-dimethyl-1,4-dihydro-benzo[d][1,3]-oxazin-2-one;
g) 3-[3-(4,4-Dimethyl-2-oxo-1,4-dihydro-2H-benzo[d][1,3]oxazin-6-yl)-phenyl]-propynenitrile;
h) 6-(3-Fluoro-5-nitro-phenyl)-4,4-dimethyl-1,4-dihydro-benzo[d][1,3]oxazin-2-one; and
i) 6-(3-Chloro-5-fluoro-phenyl)-4,4-dimethyl-1,4-dihydro-benzo[d][1,3]oxazin-2-one;

or a pharmaceutically acceptable salt thereof.

14. The method according to claim 1, wherein the anti-progestin compound is selected from the group consisting of:
a) 3-Chloro-5-(4,4-dimethyl-2-oxo-1,4-dihydro-2H-benzo[d][1,3]oxazin-6-yl)-benzonitrile;
b) 6-(3,5-Dinitro-phenyl)-4,4-dimethyl-1,4-dihydro-benzo[d][1,3]oxazin-2-one;
c) 5-(4,4-Dimethyl-2-oxo-1,4-dihydro-2H-benzo[d][1,3]oxazin-6-yl)-isophthalonitrile;
d) 4,4-Dimethyl-6-(3-thiazol-2-yl-phenyl)-1,4-dihydro-benzo[d][1,3]oxazin-2-one;
e) 6-(3-Fluoro-5-methoxy-phenyl)-4,4-dimethyl-1,4-dihydro-benzo[d][1,3]oxazin-2-one;
f) 6-(3-Fluoro-5-trifluoromethyl-phenyl)-4,4-dimethyl-1,4-dihydro-benzo[d][1,3]oxazin-2-one;
g) 6-(5-Bromo-pyridin-3-yl)-4,4-dimethyl-1,4-dihydro-benzo[d][1,3]oxazin-2-one;
h) 6-(5-Bromo-1-oxy-pyridin-3-yl)-4,4-dimethyl-1,4-dihydro-benzo[d][1,3]oxazin-2-one; and
i) 5-(4,4-Dimethyl-2-oxo-1,4-dihydro-2H-benzo[d][1,3]oxazin-6-yl)-2-fluoro-benzonitrile;

or a pharmaceutically acceptable salt thereof.

15. The method according to claim 1, wherein the anti-progestin compound is selected from the group consisting of:
a) 4-(8-Fluoro-4,4-dimethyl-2-oxo-1,4-dihydro-2H-benzo[d][1,3]oxazin-6-yl)-thiophene-2-carbonitrile;
b) 3-Fluoro-5-(8-fluoro-4,4-dimethyl-2-oxo-1,4-dihydro-2H-benzo[d][1,3]oxazin-6-yl)-benzonitrile;
c) 5-(4,4-Dimethyl-2-oxo-1,4-dihydro-2H-benzo[d][1,3]oxazin-6-yl)-thiophene-3-carbonitrile;
d) 2-(4,4-Dimethyl-2-oxo-1,4-dihydro-2H-benzo[d][1,3]oxazin-6-yl)-thiophene-3-carbonitrile;
e) 6-(1,2,4-thiadiazol-3-yl-phenyl)-4,4-dimethyl-1,4-dihydro-benzo[d][1,3]oxazin-2-one;
f) 6-(3-Fluoro-5-thiophen-3-yl-phenyl)-4,4-dimethyl-1,4-dihydro-benzo[d][1,3]oxazin-2-one;
g) 4,4-Dimethyl-6-(5-nitro-1H-pyrrol-2-yl)-1,4-dihydrobenzo[d][1,3]oxazin-2-one; and
h) 4,4-Dimethyl-6-(1H-pyrrol-2-yl)-1,4-dihydro-benzo[d][1,3]-oxazin-2-one;

or a pharmaceutically acceptable salt thereof.

16. The method according to claim 1, wherein the anti-progestin compound is selected from the group consisting of:
a) 4,4-Dimethyl-6-(1-methyl-1H-pyrrol-2-yl)-1,4-dihydro-benzo[d][1,3]oxazin-2-one;
b) 4,4-Dimethyl-6-(1-methyl-5-nitro-1H-pyrrol-2-yl)-1,4-dihydro-benzo[d][1,3]oxazin-2-one;
c) 3-(1,2-Dihydro-2-oxospiro[4H-3,1-benzoxazine-4,1-cyclohexan]-6-yl)-benzonitrile;
d) 3-(1,2-Dihydro-2-oxospiro[4H-3,1-benzoxazine-4,1-cyclohexan]-6-yl)-5-fluorobenzonitrile;
e) 4-(1,2-Dihydro-2-oxospiro[4H-3,1-benzoxazine-4,1-cyclohexan]-6-yl)-2-thiophenecarbonitrile;
f) 5-(1,2-Dihydro-2-oxospiro[4H-3,1-benzoxazine-4,1-cyclohexan]-6-yl)-2-thiophenecarbonitrile;
g) 5-(1,2-Dihydro-2-oxospiro[4H-3,1-benzoxazine-4,1-cyclohexan]-6-yl)-4-methyl-2-thiophenecarbonitrile;
h) 5-(4,4-Dimethyl-2-oxo-1,4-dihydro-2H-benzo[d][1,3]oxazin-6-yl)-4-ethyl-thiophene-2-carbonitrile; and
i) 5-(4,4-Dimethyl-2-oxo-1,4-dihydro-2H-benzo[d][1,3]oxazin-6-yl)-4-n-propyl-thiophene-2-carbonitrile;

or a pharmaceutically acceptable salt thereof.

17. The method according to claim 1, wherein the anti-progestin compound is selected from the group consisting of:
a) 6-(4-Cyano-3-fluorophenyl)-4,4-dimethyl-1,4-dihydrobenzo[d][1,3]-oxazin-2-one;
b) 6-(4-Fluoro-phenyl)-4,4-dimethyl-1,4-dihydro-benzo[d][1,3]-oxazin-2-one;
c) 6-(3,4-Difluoro-phenyl)-4,4-dimethyl-1,4-dihydro-benzo[d][1,3]oxazin-2-one;
d) 6-(2-Fluoro-phenyl)-4,4-dimethyl-1,4-dihydro-benzo[d][1,3]-oxazin-2-one;
e) 3-(4,4-Dimethyl-2-oxo-1,4-dihydro-2H-benzo[d][1,3]-oxazin-6-yl)phenylacetonitrile;
f) 5-(4,4-Dimethyl-2-oxo-1,4-dihydro-2H-benzo[d][1,3]oxazin-6-yl)-furan-2-carbonitrile;
g) 5-(4,4-Dimethyl-2-oxo-1,4-dihydro-2H-benzo[d][1,3]oxazin-6-yl)-furan-2-carbonitrile; and
h) 3-(4,4-Dimethyl-2-oxo-1,4-dihydro-2H-benzo[d][1,3]oxazin-6-yl)-2-fluoro-benzonitrile;

or a pharmaceutically acceptable salt thereof.

18. The method according to claim 1, wherein the progestational agent is selected from the group consisting of levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl) norgestimate.

19. The method of contraception according to claim 1, which comprises:
   a) a first phase of 21 daily dosage units, each daily dosage unit containing said progestational agent and ethinyl estradiol;
   b) a second phase of 3 daily dosage units, each daily dosage unit containing said antiprogestin and ethinyl estradiol; and
   c) optionally, a third phase of 4 daily dosage units of an orally and pharmaceutically acceptable placebo.

20. A pharmaceutically useful kit adapted for daily oral administration which comprises:
   a) a first phase of from 18 to 21 daily dosage units of a progestational agent equal in progestational activity to about 35 to about 150 µg levonorgestrel and ethinyl estradiol at a daily dose range of from about 10 to about 35 µg;
   b) a second phase of from 1 to 7 daily dosage units of an antiprogestin of the structure:

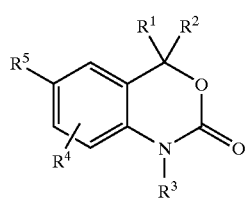

I wherein:
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$;
or $R^1$ and $R^2$ are fused to form:
   (i) a carbon-based 3 to 8 membered saturated spirocyclic ring;
   (ii) a carbon-based 3 to 8 membered spirocyclic ring having in its backbone one or more carbon-carbon double bonds; or
   (iii) a 3 to 8 membered heterocyclic ring having in its backbone one to three heteroatoms selected from the group consisting of O, S and N;
   the spirocyclic rings of (i), (ii) and (iii) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl$)_2$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^B$ is H, $C_1$ to $C_3$ alkyl, or substituted $C_1$ to $C_3$ alkyl;
$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;
$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^4$ is H, halogen, CN, $NO_2$, $C_1$ to $C_6$ alkyl, substituted $C_1$ to $C_6$ alkyl, alkynyl, substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;
$R^5$ is (iv), (v), (vi), or (vii)
   (iv) a substituted benzene ring having the substituents X, Y and Z:

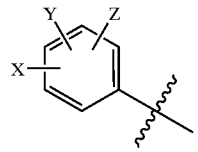

wherein:
X is selected from the group consisting of halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^ECOR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
Y and Z are independent substituents selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy;
   (v) a five membered ring having in its backbone 1, 2, or 3 heteroatoms selected from the group consisting of O, S, SO, and $SO_2$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^GCOR^F$;
   (vi) a five membered ring having in its backbone 1, 2, or 3 $NR^6$ heteroatoms and having one or two independent substituents selected from the group consisting of H, halogen, $NO_2$, amino, $C_1$ to $C_3$ alkyl, $C_1$ to $C_3$ alkoxy, $C_1$ to $C_3$ aminoalkyl, $COR^F$, and $NR^GCOR^F$; or
   (vii) a six membered ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^GCOR^F$;
      $R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
      $R^G$ is H, $C_1$ to $C_3$ alkyl, or substituted $C_1$ to $C_3$ alkyl;
$R^6$ is H or $C_1$ to $C_3$ alkyl;
or pharmaceutically acceptable salt thereof;
at a daily dose of from about 2 to 50 mg; and
   c) a third phase of from 0 to 9 daily dosage units of an orally and pharmaceutically acceptable placebo;

wherein the total number of the daily dosage units in the first phase, second phase and third phase equals 28.

21. The pharmaceutically useful kit adapted for daily oral administration according to claim 22 which comprises:
   a) a first phase of 21 daily dosage units of said progestational agent and ethinyl estradiol;
   b) a second phase of 3 daily dosage units of said antiprogestin of formula I; and
   c) a third phase of 4 daily dosage units of an orally and pharmaceutically acceptable placebo.

22. A pharmaceutically useful kit adapted for daily oral administration which comprises:
   a) a first phase of from 18 to 21 daily dosage units, each daily dosage unit comprising a progestational agent at a daily dose equal in progestational activity to from about 35 to about 150 μg levonorgestrel and ethinyl estradiol at a daily dose range of from about 10 to about 35 μg;
   b) a second phase of from 1 to 7 daily dosage units, each daily dosage unit containing an antiprogestin of the structure:

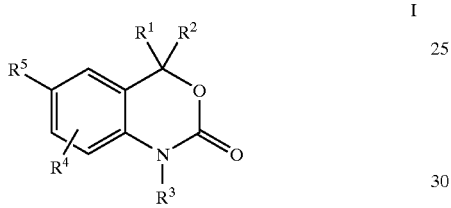

I wherein:
   $R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^B COR^A$;
   or $R^1$ and $R^2$ are fused to form:
      (i) a carbon-based 3 to 8 membered saturated spirocyclic ring;
      (ii) a carbon-based 3 to 8 membered spirocyclic ring having in its backbone one or more carbon-carbon double bonds; or
      (iii) a 3 to 8 membered heterocyclic ring having in its backbone one to three heteroatoms selected from the group consisting of O, S and N;
      the spirocyclic rings of (i), (ii) and (iii) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl$)_2$;
   $R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
   $R^B$ is H, $C_1$ to $C_3$ alkyl, or substituted $C_1$ to $C_3$ alkyl;
   $R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;
   $R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
   $R^4$ is H, halogen, CN, $NO_2$, $C_1$ to $C_6$ alkyl, substituted $C_1$ to $C_6$ alkyl, alkynyl, substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;
   $R^5$ is (iv), (v), (vi), or (vii)
      (iv) a substituted benzene ring having the substituents X, Y and Z:

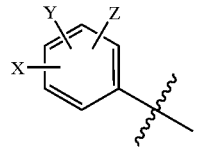

wherein:
   X is selected from the group consisting of halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^E COR^D$;
   $R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
   $R^E$ is H, $C_1$ to $C_3$ alkyl, or substituted $C_1$ to $C_3$ alkyl;
   Y and Z are independent substituents selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy;
   (v) a five membered ring having in its backbone 1, 2, or 3 heteroatoms selected from the group consisting of O, S, SO, and $SO_2$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^G COR^F$;
   (vi) a five membered ring having in its backbone 1, 2, or 3 $NR^6$ heteroatoms and having one or two independent substituents selected from the group consisting of H, halogen, $NO_2$, amino, $C_1$ to $C_3$ alkyl, $C_1$ to $C_3$ alkoxy, $C_1$ to $C_3$ aminoalkyl, $COR^F$, and $NR^G COR^F$; or
   (vii) a six membered ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^G COR^F$;
   $R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
   $R^G$ is H, $C_1$ to $C_3$ alkyl, or substituted $C_1$ to $C_3$ alkyl;
   $R^6$ is H or $C_1$ to $C_3$ alkyl;
or pharmaceutically acceptable salt thereof;
at a concentration of from 2 to 50 mg and ethinyl estradiol at a concentration of from about 10 to about 35 μg; and c) a third phase of from 0 to 9 daily dosage units of an orally and pharmaceutically acceptable placebo;

wherein the total number of the daily dosage units in the first phase, second phase and third phase equals 28.

23. The pharmaceutically useful kit adapted for daily oral administration according to claim 22, which comprises:
a) a first phase of 21 daily dosage units, each daily dosage unit containing said progestational agent and ethinyl estradiol;
b) a second phase of 3 daily dosage units, each daily dosage unit containing said antiprogestin of formula I and ethinyl estradiol; and
c) a third phase of 4 daily dosage units of an orally and pharmaceutically acceptable placebo.

24. A method of contraception which comprises administering to a female of child bearing age over a period of 28 consecutive days:
a) a first phase of from 18 to 21 daily dosage units containing a progestational agent at a daily dose equal in progestational activity to from about 35 to about 150 μg levonorgestrel and ethinyl estradiol at a daily dose range of from about 10 to about 35 μg;
b) a second phase of from 1 to 7 daily dosage units, each daily dosage unit containing an antiprogestin of the formula:

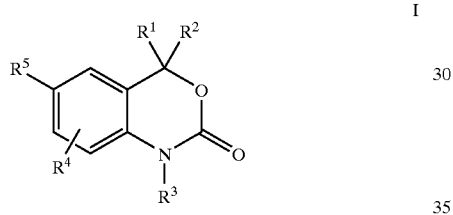

I wherein:
$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;
$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;
or $R^1$ and $R^2$ are fused to form:
(i) a carbon-based 3 to 8 membered saturated spirocyclic ring;
(ii) a carbon based 3 to 8 membered spirocyclic ring having in its backbone or more carbon-carbon double bonds; or
(iii) a carbon-based 3 to 8 membered heterocyclic ring having in its backbone one to three heteroatoms selected from the group consisting of O, S and N;
the spirocyclic rings of (i), (ii) and (iii) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl)$_2$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;
$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;
$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;
$R^5$ is (iv), (v), (vi), or (vii):
(iv) a substituted benzene ring of the structure:

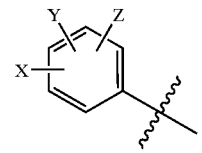

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring containing in its backbone 1 to 3 heteroatoms, $COR^D$, $OCOR^D$ and $NR^E COR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy;
(v) a five membered ring having in its backbone 1, 2, or 3 heteroatoms selected from the group consisting of O, S, SO, and $SO_2$ and containing one or two independent substituents selected from the group consisting of H, halogen, CN, $NO_2$, amino, $C_1$ to $C_3$ alkyl, and $C_1$ to $C_3$ alkoxy;
(vi) a five membered ring having in its backbone 1, 2, or 3 $NR^6$ heteroatoms and containing one or two independent substituents selected from the group consisting of H, halogen, $NO_2$, amino, $C_1$ to $C_3$ alkyl, and $C_1$ to $C_3$ alkoxy; or
(vii) a six membered ring having in its backbone 1, 2, or 3 heteroatoms selected from the group consisting of O, S, SO, $SO_2$ and $NR^6$ and containing one or two independent substituents selected from the group consisting of H, halogen, CN, $NO_2$, amino, $C_1$ to $C_3$ alkyl, and $C_1$ to $C_3$ alkoxy;
$R^6$ is H, or $C_1$ to $C_3$ alkyl;
or pharmaceutically acceptable salt thereof;
at a concentration of from 2 to 50 mg and ethinyl estradiol at a concentration of from about 10 to about 35 μg; and
c) optionally, a third phase of daily dosage units of an orally and pharmaceutically acceptable placebo, the total of the daily dosage units being 28.

25. A method of contraception which comprises administering to a female of child bearing age over a period of 28 consecutive days:

a) a first phase of from 18 to 21 daily dosage units containing a progestational agent at a daily dose equal in progestational activity to from about 35 to about 150 μg levonorgestrel and ethinyl estradiol at a daily dose range of from about 10 to about 35 μg;

b) a second phase of from 1 to 7 daily dosage units, each daily dosage unit containing an antiprogestin of the formula:

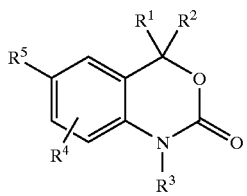

I wherein:
$R^1=R^2$ and are selected from the group consisting of $C_1$ to $C_3$ alkyl and substituted $C_1$ to $C_3$ alkyl;
or $R^1$ and $R^2$ are fused to form a carbon-based 3 to 6 membered saturated spirocyclic ring;
$R^3$ is H, OH, $NH_2$, $C_1$ to $C_6$ alkyl, substituted $C_1$ to $C_6$ alkyl, or $COR^C$;
$R^C$ is H, $C_1$ to $C_4$ alkyl, or $C_1$ to $C_4$ alkoxy;
$R^4$ is H, halogen, CN, $NO_2$, $C_1$ to $C_3$ alkyl, substituted $C_1$ to $C_3$ alkyl, $C_1$ to $C_3$ alkoxy, or substituted $C_1$ to $C_3$ alkoxy;
$R^5$ is (i), (ii), (iii), or iv):
(i) a substituted benzene ring of the structure:

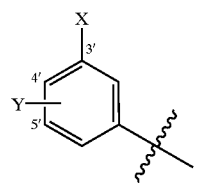

wherein:
X is halogen, CN, $C_1$ to $C_3$ alkoxy, $C_1$ to $C_3$ alkyl, $NO_2$, $C_1$ to $C_3$ perfluoroalkyl, 5 membered heterocyclic ring containing in its backbone 1 to 3 heteroatoms, or $C_1$ to $C_3$ thioalkoxy;
Y is H, halogen, CN, $NO_2$, $C_1$ to $C_3$ alkoxy, $C_1$ to $C_4$ alkyl, or $C_1$ to $C_3$ thioalkoxy;
(ii) a five membered ring of the structure:

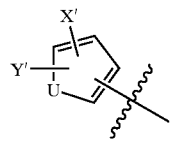

wherein:
U is O or S;
X' is selected from the group consisting of halogen, CN, $NO_2$, $C_1$ to $C_3$ alkyl and $C_1$ to $C_3$ alkoxy;
Y' is selected from the group consisting of H and $C_1$ to $C_4$ alkyl;

(iii) the five membered ring of the structure:

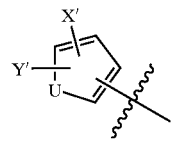

wherein:
U is $NR^6$;
X' is selected from the group consisting of halogen, $NO_2$, $C_1$ to $C_3$ alkyl and $C_1$ to $C_3$ alkoxy;
Y' is selected from the group consisting of H and $C_1$ to $C_3$ alkyl; or
(iv) a six membered ring of the structure:

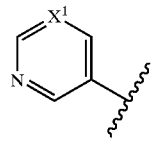

wherein:
$X^1$ is N or $CX^2$;
$X^2$ is halogen, CN, alkoxy, or $NO_2$;
$R^6$ is H, $C_1$ to $C_3$ alkyl, or $C_1$ to $C_4$ $CO_2$alkyl;

or pharmaceutically acceptable salt thereof;

at a concentration of from 2 to 50 mg and ethinyl estradiol at a concentration of from about 10 to about 35 μg; and c) optionally, a third phase of daily dosage units of an orally and pharmaceutically acceptable placebo, the total of the daily dosage units being 28.

26. The method according to claim 25, wherein the antiprogestin is 6-(3-Cyano-5-fluoro-phenyl)-4,4-dimethyl-2-oxo-4H-benzo[d][1,3]oxazine-1-carboxylic acid tert-butyl ester; 2-(4,4-Dimethyl-2-oxo-1,4-dihydro-2H-benzo[d][1,3] oxazin-6-yl)-pyrrole-1-carboxylic acid tert-butyl ester; 2-(4, 4-Dimethyl-2-oxo-1,4-dihydro-2H-benzo[d][1,3]oxazin-6-yl)-5-nitro-pyrrole-1-carboxylic acid tert-butyl ester; and 5-(4,4-Dimethyl-2-oxo-1,4-dihydro-2H-benzo[d][1,3] oxazin-6-yl)-4-n-butyl-thiophene-2-carbonitrile; 5-(4,4-Dimethyl-2-oxo-1,4-dihydro-2H-benzo[d][1,3]oxazin-6-yl)-4-n-butyl-thiophene-2-carbonitrile; or a pharmaceutically acceptable salt thereof.

27. A method of contraception which comprises administering to a female of child bearing age over a period of 28 consecutive days:

a) a first phase of from 18 to 21 daily dosage units containing a progestational agent at a daily dose equal in progestational activity to from about 35 to about 150 μg levonorgestrel and ethinyl estradiol at a daily dose range of from about 10 to about 35 μg;

b) a second phase of from 1 to 7 daily dosage units, each daily dosage unit containing an antiprogestin of the formula:

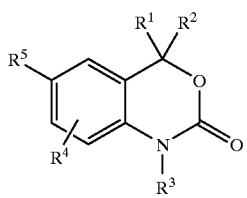

wherein:
R¹ and R² are CH₃ or R¹ and R² are fused to form a carbon-based 6 membered spirocyclic saturated ring
R³ is H, OH, NH₂, CH₃, substituted CH₃, or COR^A;
R^A is H, C₁ to C₃ alkyl, or C₁ to C₄ alkoxy;
R⁴ is H, halogen, NO₂, CN, or C₁ to C₃ alkyl;
R⁵ is (i) or (ii):
(i) a substituted benzene ring of the formula:

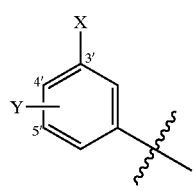

wherein:

X is selected from the group consisting of halogen, CN, methoxy, NO₂, 5-membered heterocyclic ring;
  wherein said 5-membered heterocyclic ring is 2-thiazole;
  Y is H or halogen;
  wherein said halogen is F; or
(ii) a five membered ring of the structure:

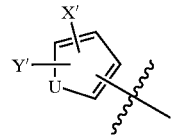

wherein:
  U is O, S, or NH;
  X' is halogen, CN, or NO₂, provided that when U is NH, X is not CN;
  Y' is H or C₁ to C₄ alkyl
or pharmaceutically acceptable salt thereof;
at a concentration of from 2 to 50 mg and ethinyl estradiol at a concentration of from about 10 to about 35 μg; and c) optionally, a third phase of daily dosage units of an orally and pharmaceutically acceptable placebo, the total of the daily dosage units being 28.

* * * * *

UNITED STATES PATENT AND TRADEMARK OFFICE
CERTIFICATE OF CORRECTION

PATENT NO. : 6,759,408 B2
DATED : July 6, 2004
INVENTOR(S) : Grubb et al.

It is certified that error appears in the above-identified patent and that said Letters Patent is hereby corrected as shown below:

Column 7,
Line 13, replace "also kits" with -- also has kits --;
Line 20, replace "each the days" with -- each of the days --.

Column 11,
Line 15, replace "-NH(C2 to C6" with -- -NH(C1 to C6 --.

Column 34,
Line 8, replace "1-(4-amino-3-chloro-" with -- 1-(4-amino-3'-chloro- --.
Line 33, replace "1-(4-amino-3-chloro-biphenyl-3-yl)-1-" with -- 1-(4-amino-3'-chloro-biphenyl-3-yl)-1- --.

Column 35,
Line 40, replace "-2,2,2,-tifluoro-" with -- -2,2,2,-trifluoro --.

Column 40,
Line 17, replace "dihydro-benzo" with -- dihydrobenzo --.

Column 41,
Line 20, replace "-5fluoro" with -- -5-fluoro- -- .
Line 37, replace "([M-H]+" with -- ([M-H]- --.

Column 42,
Line 1, replace "-5fluoro-phenyl)" with -- -5-fluoro-phenyl) --.
Line 46, replace "dimethyldihydrobenzo" with -- dimethyldihydro-benzo --.

Column 44,
Line 20, replace "a off-white" with -- an off-white --.

Column 54,
Line 59, replace "(n, 1H)," with -- (m, 1 H), --.

Column 56,
Line 3, replace "(r, 2H)," with -- (m, 2H) --.

Column 57,
Line 28, Table 1, replace "7-(2-cyano-" with -- 4-(2- -- .

UNITED STATES PATENT AND TRADEMARK OFFICE
CERTIFICATE OF CORRECTION

PATENT NO. : 6,759,408 B2
DATED : July 6, 2004
INVENTOR(S) : Grubb et al.

It is certified that error appears in the above-identified patent and that said Letters Patent is hereby corrected as shown below:

Column 58,
Line 60, replace "streptonycin," with -- streptomycin --.

Column 68,
Line 26, replace "[1,3oxazin-6-yl)" with -- [1,3] oxazin --.
Line 39, replace "-2y1]acetonitrile" with - -2-yl]acetonitrile --.

Column 69,
Line 17, replace "was a colorless oil:" with -- as a colorless oil: --.

Column 70,
Line 45, replace "C17H16FNO3" with -- C17H16FNO3: --.

Column 71,
Line 4, replace "7,59" with -- 7.59 --.
Line 32, replace "C15H5N3O2" with -- C15H15N3O2 --.
Line 41, replace "diethoxymeyhyl" with -- diethoxymethyl --.

Signed and Sealed this

Twenty-fifth Day of January, 2005

JON W. DUDAS
*Director of the United States Patent and Trademark Office*